US007919078B2

(12) United States Patent
Schreiber et al.

(10) Patent No.: US 7,919,078 B2
(45) Date of Patent: Apr. 5, 2011

(54) RECOMBINANT INTERFERON α2 (IFNα2) MUTANTS AND METHODS OF USE THEREOF

(75) Inventors: Gideon E Schreiber, Rehovot (IL); Laila C. Roisman, Tel Aviv (IL); Diego Jaitin, Rehovot (IL); Eyal Kalie, Hod Hasharon (IL)

(73) Assignee: Yeda Research and Development Co. Ltd. at the Weizmann Institute of Science, Rehovot (IL)

( * ) Notice: Subject to any disclaimer, the term of this patent is extended or adjusted under 35 U.S.C. 154(b) by 139 days.

(21) Appl. No.: 11/969,319

(22) Filed: Jan. 4, 2008

(65) Prior Publication Data

US 2008/0166319 A1    Jul. 10, 2008

Related U.S. Application Data

(63) Continuation-in-part of application No. 11/994,159, filed as application No. PCT/IL2006/000754 on Jun. 28, 2006, now Pat. No. 7,767,799.

(60) Provisional application No. 60/694,810, filed on Jun. 29, 2005.

(51) Int. Cl.
*A61K 38/21* (2006.01)
*C07K 14/56* (2006.01)

(52) U.S. Cl. .................................. 424/85.7; 530/351

(58) Field of Classification Search .................. None
See application file for complete search history.

(56) References Cited

U.S. PATENT DOCUMENTS

| 4,588,585 | A |   | 5/1986  | Mark et al. ............... 424/85 |
|-----------|---|---|---------|-----------------------------------|
| 4,766,106 | A |   | 8/1988  | Katre et al. .............. 514/12 |
| 4,917,888 | A |   | 4/1990  | Katre et al. ............ 424/85.91 |
| 5,382,657 | A | * | 1/1995  | Karasiewicz et al. ....... 530/351 |
| 5,609,868 | A | * | 3/1997  | Lowther et al. ........... 424/85.7 |
| 6,214,966 | B1|   | 4/2001  | Harris ...................... 528/322 |
| 7,141,547 | B2|   | 11/2006 | Rosen et al. .............. 514/12 |
| 2004/0002474 | A1 | | 1/2004 | Heinrichs et al. ............ 514/44 |
| 2004/0132977 | A1 | | 7/2004 | Gantier et al. ............. 530/351 |
| 2004/0230040 | A1 | | 11/2004 | Cox, III .................... 530/351 |
| 2007/0148739 | A1 | * | 6/2007 | Jones et al. ............... 435/69.51 |

FOREIGN PATENT DOCUMENTS

| WO | WO 93/04699   | A1 | 3/1993  |
|----|---------------|----|---------|
| WO | WO 97/12630   | A1 | 4/1997  |
| WO | WO 01/54678   | A2 | 8/2001  |
| WO | WO 02/066649  | A2 | 8/2002  |
| WO | WO 2004/022747|    | 3/2004  |
| WO | WO 2004/089280| A2 | 10/2004 |
| WO | WO 2005/016371|    | 2/2005  |
| WO | WO 2006/020580|    | 2/2006  |

OTHER PUBLICATIONS

Argos, "A possible homology between immunodeficiency virus p24 core protein and picornaviral VP2 coat protein: prediction of HIV p24 antigenic sites," The EMBO Journal, 8(3): 779-785 (1989).

Chawla-Sarkar et al., "Preferential Induction of Apoptosis by Interferon (IFN)-β Compared with IFN-α2: Correlation with TRAIL/Apo2L Induction in Melanoma Cell Lines," Clinical Cancer Research, 7: 1821-1831 (2001).
Gilli et al., "Neutralizing antibodies against IFN-β in multiple sclerosis: antagonization of IFN-β mediated suppression of MMPs," Brain, 127: 259-268 (2004).
Hu et al., "Human IFN-α Protein Engineering: The Amino Acid Residues at Positions 86 and 90 are Important for Antiproliferative Activity," The Journal of Immunology, 167: 1482-1489 (2001).
Jaitin et al., "Inquiring into the Differential Action of Interferons (IFNs): an IFN-α2 Mutant with Enhanced Affinity to IFNAR1 is Functionally Similar to IFN-β," Molecular and Cellular Biology, 26(5): 1888-1897 (2006).
Kalie et al., "An Interferon α2 Mutant Optimized by Phage Display for IFNAR1 Binding Confers Specifically Enhanced Antitumor Activities," The Journal of Biological Chemistry, 282(15): 11602-11611 (2007).
Lamken et al., "Ligand-induced Assembling of the Type 1 Interferon Receptor on Supported Lipid Bilayers," J. Mol. Biol., 341: 303-318 (2004).
Piehler et al., "Biophysical Analysis of the Interaction of Human Ifnar2 Expressed in *E. coli* with IFNα2," J. Mol. Biol., 289: 57-67 (1999).
Piehler et al., "Mutational and Structural Analysis of the Binding Interface between Type 1 Interferons and their Receptor Ifnar2," J. Mol. Biol., 294: 223-237 (1999).
Riss et al., "Use of Multiple Assay Endpoints to Investigate the Effects of Incubation Time, Dose of Toxin, and Plating Density in Cell-Based Cytotoxicity Assays," Assay and Drug Development Technologies, 2(1): 51-62 (2004).
Tsutsumi et al., "Site-specific chemical modification with polyethylene glycol of recombinant immunotoxin anti-Tac(Fv)-PE38 (LMB-2) improves antitumor activity and reduces animal toxicity and immunogenicity," PNAS, 97(15): 8548-8553 (2000).
Zafranskaya et al., "Interferon-β therapy reduces CD4+ and CD8+ T-cell reactivity in multiple sclerosis," Immunology, 121: 29-39 (2006).
Arduini, Robert M. et al., "Characterization of a Soluble Ternary Complex Formed Between Human Interferon-β-1a and its Receptor Chains", Protein Science, vol. 8, pp. 1867-1877 (1999).
Brierley, Melissa M. et al., "IFN-α/β Receptor Interactions to Biologic Outcomes: Understanding the Circuitry", Journal of Interferon and Cytokine Research, vol. 22, pp. 835-845 (2002).
Campbell, Iain L. et al., "Essential Role for Interferon-γ and Interleukin-6 in Autoimmune Insulin-dependent Diabetes in NOD/Wehi Mice", Journal of Clin. Invest., vol. 87, pp. 739-742 (1991).
Chill, Jordan H., et al., "The Human Type I Interferon Receptor: NMR Structure Reveals the Moleculor Basis of Ligand Binding", Structure, vol. 11, pp. 791-802 (2003).

(Continued)

*Primary Examiner* — Robert Landsman
*Assistant Examiner* — Bruce D Hissong
(74) *Attorney, Agent, or Firm* — Winston & Strawn LLP

(57) ABSTRACT

The present invention provides IFNα2 mutants and active fragments, analogs, derivatives, and variants thereof, nucleotide molecules encoding same, pharmaceutical compositions containing the same, and methods utilizing the same for treating cancer, infectious diseases, and autoimmune diseases.

61 Claims, 24 Drawing Sheets

OTHER PUBLICATIONS

Cutrone, Elizabeth C. et al., "Identification of Critical Residues in Bovine IFNAR-1 Responsible for Interferon Binding", Journal of Biological Chemistry, vol. 276, pp. 17140-17148 (2001).

de Veer, Michael J. et al., "Functional Classification of Interferon-Stimulated Genes Identified Using Microarrays", Journal of Leukocyte Biology, vol. 69, pp. 912-920 (2001).

Der, Sandy D. et al., "Identification of Genes Differentially Regulated by Interferon α, β, or γ Using Oligonucleotide Arrays", Proc. National Academy Sci. USA, vol. 95, pp. 15623-15628 (1998).

Evinger, Marian et al., Antiproliferative and Antiviral Activities of Human Leukocyte Interferons, Archives of Biochemistry and Biophysics, vol. 210, pp. 319-329 (1981).

Fernandez-Martin, A. et al, "VIP Prevents Experimental Multiple Sclerosis by Downregulating Both Inflammatory and Autoimmune Components of the Disease", Ann. N.Y. Academy of Science, vol. 1070, pp. 276-281 (2006).

Gavutis M. et al., "Lateral Ligand-Receptor Interactions on Membranes Probed by Simultaneous Fluorescence-Interference Detection", Biophysical Journal, vol. 88, No. 6, pp. 4289-4302 (2005).

Goldman, Lisa A. et al., "Mapping Human Interferon-alpha (IFN-α2) Binding Determinants of the Type I Interferon Receptor Subunit IFNAR-1 with Human/Bovine IFNAR-1 Chimeras", Biochemistry Journal, vol. 37, pp. 13003-13010 (1998).

Hu, Renqiu et al., "Divergence of Binding, Signaling, and Biological Responses to Recombinant Human Hybrid IFN", Journal of Immunology, vol. 163, pp. 854-860 (1999).

Klaus, Werner et al., "The Three-Dimensional High Resolution Structure of Human Interferon α -2a Determined by Heteronuclear NMR Spectroscopy in Solution", Journal of Molecular Biology, vol. 274, pp. 661-675 (1997).

Kotenko, Sergei V. et al., "Full House: 12 Receptors for 27 Cytokines", International Immunopharmacology, vol. 4, pp. 593-608 (2004).

Piehler, Jacob et al., "Fast Transient Cytokine-Receptor Interactions Monitored in Real Time by Reflectometric Interference Spectroscopy", Analytical Biochemistry, vol. 289, pp. 173-186 (2001).

Piehler, Jacob et al., "New Structural and Functional Aspects of the Type I Interferon-Receptor Interaction Revealed by Comprehensive Mutational Analysis of the Binding Interface", Journal of Biological Chemistry, vol. 275, No. 51, pp. 40425-40433 (2000).

Platanias, Leonidas C. et al., "Signaling Pathways Activated by Interferons", Experimental Hematology, vol. 27, pp. 1583-1592 (1999).

Roisman, Laila C. et al., "Mutational Analysis of the IFNAR1 Binding Site on IFNα2 Reveals the Architecture of a Weak Ligand-Receptor Binding-Site", Journal of Molecular Biology, vol. 353, pp. 271-281 (2005).

Runkel, Laura et al., "Systematic Mutational Mapping of Sites on Human Interferon-B-1a that are Important for Receptor Binding and Functional Activity", Biochemistry, vol. 39, pp. 2538-2551 (2000).

Schmeisser, Hana et al., "Amino Acid Substitutions in Loop BC and Helix C Affect Antigenic Properties of Helix D in Hybrid IFN-α21a/α2c Molecules", Journal of Interferon and Cytokine Research, vol. 22, pp. 463-472 (2002).

Schmitt, Hans-Martin, et al., "An Integrated System for Optical Biomolecular Interaction Analysis", Biosensors & Bioelectronics, vol. 12, No. 8, pp. 809-816 (1997).

Uzé, Gilles et al., Genetic Transfer of a Functional Human Interferon Alpha Receptor into Mouse Cells: Cloning and Expression of its cDNA. Cell., vol. 60, pp. 225-234 (1990).

Villa Erica et al., 1996, "Alpha but not Beta Interferon is Useful in Chronic Active Hepatitis due to Hepatitis C Virus. A Prospective, Double-Blind, Randomized Study", Digestive Diseases and Sciences, vol. 41, No. 6, pp. 1241-1247 (1996).

Ytterberg Steven R. et al., "Serum Interferon Levels in Patients with Systemic Lupus Erythematosus", Arthritis and Rheumatism, vol. 25, pp. 401-406 (1982).

U.S. Appl. No. 11/994,159 Requirement for Restriction/Election dated May 6, 2009.

U.S. Appl. No. 11/994,159 Non-Final Rejection dated Jul. 13, 2009.

U.S. Appl. No. 11/994,159 Final Rejection dated Jan. 11, 2010.

* cited by examiner

```
Receptor                             2        22 22222
                                     -           -----
IFNα2    1 --CDLPQTHSLGSRRTLMLLAQMR-KISLFSCLKDRHDFGFPQEEF-GNQFQKAETIPVL
IFNα5    1 --..........H...M........-R..............R.....D........A.S..
IFNα13   1 --.....E....DN...........S-R..PS...M..........D.......PA.S..
IFNα1    1 --..........N..A.I.....G-R.PP..............D.......QA.S..
IFNα21   1 --..........N..A.I.....G-R..P..............D.......QA.S..
IFNα4    1 --..........N..A.I.....G-R..H...........E...D.H....TQA.S..
IFNα7    1 --......RN..A.I.....G-R..P.........E.R..E...D.H....TQA.S..
IFNα10   1 --..........N..A.I..G.-G-R..P.........RI....D.......QA.S..
IFNα14   1 --.N.S.....NN......M....-R..P.........E.....D.......QA.S..
IFNα16   1 --..........N..A.I.....G-R..H.........Y.....V.D.......QA.SAF
IFNα8    1 --..........N..A.I.....-R..P.........E......DDK.....QA.S..
IFNω     1 --.......N.G.L...N..V..H...-R..P.L.....R..R....MVK.S.L...HVMS..
IFNβ     1 SYNL.GFLQRSSNFQCQK..W.LNGRLEY--......MN.DI.E.IKQLQ....EDAALTI Receptor    11 1 11      1           1      1   1
            ++ +  --      -           -      -   -
IFNα2    57 HEMIQQIFNLFSTKDSSAAWDETLLDKFYTELYQQLNDLEACVIQGVGVTETPLMKEDSI
IFNα5    58 ..V....T...........V....R.....L...............M.E.W.GG....N....
IFNα13   58 ..L........T..........D.......C...............M.EER.G.....NA...
IFNα1    58 .........T........T.EQS..E..S....N.............E...E.....NV...
IFNα21   58 .........T........T.EQS..E..S....N......M......E...E.....NV...
IFNα4    58 .........T.......E....EQS..E..S.................E...E.....NV...
IFNα7    58 .........T.......E....EQS..E..S.................E...E.....NV...
IFNα10   58 .........T.......E....EQS..E..S.................E...E.....N..F.
IFNα14   58 ...M....T..........N........E...I..F..M........E...E.....N....
IFNα16   58 .........T.................I..F.........T.E...E.IA..N....
IFNα8    58 .........T..........L......E...I..D......S..M.E...I.S...Y....
IFNω     58 ...L.....S..H.ER.....NM.....QIH.G.H....QH..T.LL.V..EG.SAGAISSPA
IFNβ     59 Y.L.N..AI.RQDS..TG.N..IVENLLANV.H.I.H.KTVLEEKLEKEDFTRG.LM.S Receptor         2              2 222  22
                 -              -  --
117 LAVRKYFQRITLYLKEKKYSPCAWEVVRAEIMRSFSLSTNLQESLRSKE------  (SEQ ID NO:2)
118 ............T.......................S.R....R..R..------  (SEQ ID NO:53)
118 ...K...R....T...............L........R..R..------  (SEQ ID NO:54)
118 ...K........T.................KIF..R..R..------  (SEQ ID NO:1)
118 ...K........T.................KIF..R..R..Z-----  (SEQ ID NO:55)
118 ............T.................L.F.....KR..R.D------  (SEQ ID NO:56)
118 ...........M........................F....------------  (SEQ ID NO:57)
118 .........I.R..................L.F.....KR..R.------  (SEQ ID NO:58)
118 ...K........M..................F.....KR..R.------  (SEQ ID NO:59)
118 ............MG.................F.....KG..R.------  (SEQ ID NO:60)
118 ............T.....S...............I..KR.K...------  (SEQ ID NO:61)
118 .TL.R...G.RV........D.......M...K.LF....M..R....DRDLGSS  (SEQ ID NO:62)
119 .HLKR.YG..LH...A.E..H...TI..V..L.N.YFINR.TGY..N--------  (SEQ ID NO:3)
```

Fig. 2A

SEQUENCE LISTING

```
<160> NUMBER OF SEQ ID NOS: 62

<210> SEQ ID NO 1
<211> LENGTH: 166
<212> TYPE: PRT
<213> ORGANISM: Homo sapiens

<400> SEQUENCE: 1

Cys Asp Leu Pro Gln Thr His Ser Leu Gly Asn Arg Arg Ala Leu Ile
1               5                   10                  15
```

```
Leu Leu Ala Gln Met Gly Arg Ile Pro Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Gln Leu Asn Asp Leu
                85                  90                  95

Glu Ala Cys Val Ile Gln Glu Val Gly Val Glu Thr Pro Leu Met
            100                 105                 110

Asn Val Asp Ser Ile Leu Ala Val Lys Lys Tyr Phe Gln Arg Ile Thr
            115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 2
<211> LENGTH: 165
<212> TYPE: PRT
<213> ORGANISM: Homo sapiens

<400> SEQUENCE: 2

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 3
<211> LENGTH: 165
<212> TYPE: PRT
<213> ORGANISM: Homo sapiens

<400> SEQUENCE: 3

Ser Tyr Asn Leu Leu Gly Phe Leu Gln Arg Ser Ser Asn Phe Gln Cys
```

```
                1               5                   10                  15
Gln Lys Leu Leu Trp Gln Leu Asn Gly Arg Leu Glu Tyr Cys Leu Lys
                    20                  25                  30

Asp Arg Met Asn Phe Asp Ile Pro Glu Glu Ile Lys Gln Leu Gln Gln
                    35                  40                  45

Phe Gln Lys Glu Asp Ala Ala Leu Thr Ile Tyr Glu Met Leu Gln Asn
 50                     55                  60

Ile Phe Ala Ile Phe Arg Gln Asp Ser Ser Thr Gly Trp Asn Glu
 65                 70                  75                      80

Thr Ile Val Glu Asn Leu Leu Ala Asn Val Tyr His Gln Ile Asn His
                    85                  90                  95

Leu Lys Thr Val Leu Glu Glu Lys Leu Glu Lys Glu Asp Phe Thr Arg
                    100                 105                 110

Gly Lys Leu Met Ser Ser Leu His Leu Lys Arg Tyr Tyr Gly Arg Ile
                    115                 120                 125

Leu His Tyr Leu Lys Ala Lys Glu Tyr Ser His Cys Ala Trp Thr Ile
                    130                 135                 140

Val Arg Val Glu Ile Leu Arg Asn Phe Tyr Phe Ile Asn Arg Leu Thr
145                     150                 155                 160

Gly Tyr Leu Arg Asn
                165

<210> SEQ ID NO 4
<211> LENGTH: 165
<212> TYPE: PRT
<213> ORGANISM: Homo sapiens

<400> SEQUENCE: 4

Met Lys Tyr Thr Ser Tyr Ile Leu Ala Phe Gln Leu Cys Ile Val Leu
 1               5                  10                  15

Gly Ser Leu Gly Cys Tyr Cys Gln Asp Pro Tyr Val Lys Glu Ala Glu
                    20                  25                  30

Asn Leu Lys Lys Tyr Phe Asn Ala Gly His Ser Asp Val Ala Asp Asn
                    35                  40                  45

Gly Thr Leu Phe Leu Gly Ile Leu Lys Asn Trp Glu Glu Ser Asp Arg
 50                     55                  60

Lys Ile Met Gln Ser Gln Ile Val Ser Phe Tyr Phe Lys Leu Phe Lys
 65                 70                  75                      80

Asn Phe Lys Asp Asp Gln Ser Ile Gln Lys Ser Val Glu Thr Ile Lys
                    85                  90                  95

Glu Asp Met Asn Val Lys Phe Phe Asn Ser Asn Lys Lys Lys Arg Asp
                    100                 105                 110

Asp Phe Glu Lys Leu Thr Asn Tyr Ser Val Thr Asp Leu Asn Val Gln
                    115                 120                 125

Arg Lys Ala Ile His Glu Leu Ile Gln Val Met Ala Glu Leu Ser Pro
                    130                 135                 140

Ala Ala Lys Thr Gly Lys Arg Lys Arg Ser Gln Met Leu Phe Arg Gly
145                     150                 155                 160

Arg Arg Ala Ser Gln
                165

<210> SEQ ID NO 5
<211> LENGTH: 165
<212> TYPE: PRT
<213> ORGANISM: Homo sapiens

<400> SEQUENCE: 5
```

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Ala Ala Met Ile Ala Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 6
<211> LENGTH: 165
<212> TYPE: PRT
<213> ORGANISM: Homo sapiens

<400> SEQUENCE: 6

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Ala Leu Phe Ser Thr Lys Asp Ser Ser Ala Ala Trp Asp Glu Thr Ala
65                  70                  75                  80

Leu Asp Lys Phe Ala Thr Glu Leu Ala Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 7
<211> LENGTH: 165
<212> TYPE: PRT
<213> ORGANISM: Homo sapiens
```

<400> SEQUENCE: 7

```
Cys Asp Leu Pro Gln Thr His Ser Leu Gly Ser Arg Arg Thr Leu Met
1               5                   10                  15
Leu Leu Ala Gln Met Arg Arg Ile Ser Leu Phe Ser Cys Leu Lys Asp
            20                  25                  30
Arg His Asp Phe Gly Phe Pro Gln Glu Glu Phe Gly Asn Gln Phe Gln
        35                  40                  45
Lys Ala Glu Thr Ile Pro Val Leu His Glu Met Ile Gln Gln Ile Phe
    50                  55                  60
Asn Leu Phe Ser Thr Lys Asp Ser Ser Ala Ala Trp Asp Glu Thr Leu
65                  70                  75                  80
Leu Asp Lys Phe Tyr Thr Glu Leu Tyr Gln Gln Leu Asn Asp Leu Glu
                85                  90                  95
Ala Cys Val Ile Gln Gly Val Gly Val Thr Glu Thr Pro Leu Met Lys
            100                 105                 110
Glu Asp Ser Ile Leu Ala Val Arg Lys Tyr Phe Gln Arg Ile Thr Leu
        115                 120                 125
Tyr Leu Lys Glu Lys Lys Tyr Ser Pro Cys Ala Trp Glu Val Val Arg
    130                 135                 140
Ala Glu Ile Met Arg Ser Phe Ser Leu Ser Thr Asn Leu Gln Lys Arg
145                 150                 155                 160
Leu Lys Ser Lys Glu
                165
```

<210> SEQ ID NO 8
<211> LENGTH: 165
<212> TYPE: PRT
<213> ORGANISM: Homo sapiens

<400> SEQUENCE: 8

```
Cys Asp Leu Pro Gln Thr His Ser Leu Gly Ser Arg Arg Thr Leu Met
1               5                   10                  15
Leu Leu Ala Gln Met Arg Arg Ile Ser Leu Phe Ser Cys Leu Lys Asp
            20                  25                  30
Arg His Asp Phe Gly Phe Pro Gln Glu Glu Phe Gly Asn Gln Phe Gln
        35                  40                  45
Lys Ala Glu Thr Ile Pro Val Leu Ala Ala Met Ile Ala Gln Ile Phe
    50                  55                  60
Asn Leu Phe Ser Thr Lys Asp Ser Ser Ala Ala Trp Asp Glu Thr Leu
65                  70                  75                  80
Leu Asp Lys Phe Tyr Thr Glu Leu Tyr Gln Gln Leu Asn Asp Leu Glu
                85                  90                  95
Ala Cys Val Ile Gln Gly Val Gly Val Thr Glu Thr Pro Leu Met Lys
            100                 105                 110
Glu Asp Ser Ile Leu Ala Val Arg Lys Tyr Phe Gln Arg Ile Thr Leu
        115                 120                 125
Tyr Leu Lys Glu Lys Lys Tyr Ser Pro Cys Ala Trp Glu Val Val Arg
    130                 135                 140
Ala Glu Ile Met Arg Ser Phe Ser Leu Ser Thr Asn Leu Gln Lys Arg
145                 150                 155                 160
Leu Lys Ser Lys Glu
                165
```

<210> SEQ ID NO 9
<211> LENGTH: 165

```
<212> TYPE: PRT
<213> ORGANISM: Homo sapiens

<400> SEQUENCE: 9

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Ala Leu Phe Ser Thr Lys Asp Ser Ser Ala Ala Trp Asp Glu Thr Ala
65                  70                  75                  80

Leu Asp Lys Phe Ala Thr Glu Leu Ala Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Lys Arg
145                 150                 155                 160

Leu Lys Ser Lys Glu
                165

<210> SEQ ID NO 10
<211> LENGTH: 165
<212> TYPE: PRT
<213> ORGANISM: Homo sapiens

<400> SEQUENCE: 10

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Met Asp Met Ile Leu Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165
```

```
<210> SEQ ID NO 11
<211> LENGTH: 165
<212> TYPE: PRT
<213> ORGANISM: Homo sapiens

<400> SEQUENCE: 11

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Asn Met Ile Ser Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 12
<211> LENGTH: 165
<212> TYPE: PRT
<213> ORGANISM: Homo sapiens

<400> SEQUENCE: 12

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Met Asp Met Ile Leu Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Lys Arg
145                 150                 155                 160

Leu Lys Ser Lys Glu
                165
```

<210> SEQ ID NO 13
<211> LENGTH: 165
<212> TYPE: PRT
<213> ORGANISM: Homo sapiens

<400> SEQUENCE: 13

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Asn Met Ile Ser Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Lys Arg
145                 150                 155                 160

Leu Lys Ser Lys Glu
                165
```

<210> SEQ ID NO 14
<211> LENGTH: 69
<212> TYPE: DNA
<213> ORGANISM: Artificial
<220> FEATURE:
<223> OTHER INFORMATION: chemically synthesized

<400> SEQUENCE: 14
tgtgatctgc cgcagactca ctctctgggt tctcgtcgta ctctgatgct gctggctcag    60
atgcgtcgt                                                            69

<210> SEQ ID NO 15
<211> LENGTH: 501
<212> TYPE: DNA
<213> ORGANISM: Homo sapiens

<400> SEQUENCE: 15
atgtgtgatc tgccgcagac tcactctctg ggttctcgtc gtactctgat gctgctggct    60
cagatgcgtc gtatctctct tttctcctgc ttgaaggaca gacatgactt tggatttccc   120
caggaggagt ttggcaacca gttccaaaag gctgaaacca tccctgtcct cgctgcgatg   180
atcgcgcaga tcttcaatct cttcagcaca aaggactcat ctgctgcttg ggatgagacc   240
ctcctagaca aattctacac tgaactctac cagcagctga tgacctgga agccgtgtg    300 atacaggggg tggggtgac agagactccc ctgatgaagg aggactccat tctggctgtg   360
aggaaatact tccaaagaat cactctctat ctgaaagaga gaaaatacag cccttgtgcc   420
tgggaggttg tcagagcaga aatcatgaga tcttttttctt tgtcaacaaa cttgcaagaa   480
```
agtttaagaa gtaaggaatg a                                             501

<210> SEQ ID NO 16
<211> LENGTH: 501
<212> TYPE: DNA
<213> ORGANISM: Homo sapiens

<400> SEQUENCE: 16
atgtgtgatc tgccgcagac tcactctctg ggttctcgtc gtactctgat gctgctggct   60
cagatgcgtc gtatctctct tttctcctgc ttgaaggaca gacatgactt tggatttccc   120
caggaggagt ttggcaacca gttccaaaag gctgaaacca tccctgtcct ccatgagatg   180
atccagcaga tcttcgctct cttcagcaca aaggactcat ctgctgcttg ggatgagacc   240
gccctagaca aattcgccac tgaactcgcc cagcagctga tgacctgga agcctgtgtg   300 atacaggggg tggggggtgac agagactccc ctgatgaagg aggactccat tctggctgtg   360
aggaaatact tccaaagaat cactctctat ctgaaagaga agaaatacag cccttgtgcc   420
tgggaggttg tcagagcaga aatcatgaga tcttttttctt tgtcaacaaa cttgcaagaa   480
agtttaagaa gtaaggaatg a                                             501

<210> SEQ ID NO 17
<211> LENGTH: 501
<212> TYPE: DNA
<213> ORGANISM: Homo sapiens

<400> SEQUENCE: 17
atgtgtgatc tgccgcagac tcactctctg ggttctcgtc gtactctgat gctgctggct   60
cagatgcgtc gtatctctct tttctcctgc ttgaaggaca gacatgactt tggatttccc   120
caggaggagt ttggcaacca gttccaaaag gctgaaacca tccctgtcct ccatgagatg   180
atccagcaga tcttcaatct cttcagcaca aaggactcat ctgctgcttg ggatgagacc   240
ctcctagaca aattctacac tgaactctac cagcagctga tgacctgga agcctgtgtg    300 atacaggggg tggggggtgac agagactccc ctgatgaagg aggactccat tctggctgtg   360
aggaaatact tccaaagaat cactctctat ctgaaagaga agaaatacag cccttgtgcc   420
tgggaggttg tcagagcaga aatcatgaga tcttttttctt tgtcaacaaa cttgcaaaaa   480
aggttaaaaa gtaaggaatg a                                             501

<210> SEQ ID NO 18
<211> LENGTH: 501
<212> TYPE: DNA
<213> ORGANISM: Homo sapiens

<400> SEQUENCE: 18
atgtgtgatc tgccgcagac tcactctctg ggttctcgtc gtactctgat gctgctggct   60
cagatgcgtc gtatctctct tttctcctgc ttgaaggaca gacatgactt tggatttccc   120
caggaggagt ttggcaacca gttccaaaag gctgaaacca tccctgtcct cgctgcgatg   180
atcgcgcaga tcttcaatct cttcagcaca aaggactcat ctgctgcttg ggatgagacc   240
ctcctagaca aattctacac tgaactctac cagcagctga tgacctgga agcctgtgtg    300 atacaggggg tggggggtgac agagactccc ctgatgaagg aggactccat tctggctgtg   360
aggaaatact tccaaagaat cactctctat ctgaaagaga agaaatacag cccttgtgcc   420
tgggaggttg tcagagcaga aatcatgaga tcttttttctt tgtcaacaaa cttgcaaaaa   480
aggttaaaaa gtaaggaatg a                                             501

<210> SEQ ID NO 19
<211> LENGTH: 501
<212> TYPE: DNA
<213> ORGANISM: Homo sapiens

<400> SEQUENCE: 19

| | | | | | |
|---|---|---|---|---|---|
| atgtgtgatc | tgccgcagac | tcactctctg | ggttctcgtc | gtactctgat | gctgctggct | 60 |
| cagatgcgtc | gtatctctct | tttctcctgc | ttgaaggaca | gacatgactt | tggatttccc | 120 |
| caggaggagt | ttggcaacca | gttccaaaag | gctgaaacca | tccctgtcct | ccatgagatg | 180 |
| atccagcaga | tcttcgctct | cttcagcaca | aaggactcat | ctgctgcttg | ggatgagacc | 240 |
| gccctagaca | aattcgccac | tgaactcgcc | cagcagctga | atgacctgga | agcctgtgtg | 300 |
| atacaggggg | tgggggtgac | agagactccc | ctgatgaagg | aggactccat | tctggctgtg | 360 |
| aggaaatact | tccaaagaat | cactctctat | ctgaaagaga | agaaatacag | cccttgtgcc | 420 |
| tgggaggttg | tcagagcaga | aatcatgaga | tcttttttctt | tgtcaacaaa | cttgcaaaaa | 480 |
| aggttaaaaa | gtaaggaatg | a | | | | 501 |

<210> SEQ ID NO 20
<211> LENGTH: 501
<212> TYPE: DNA
<213> ORGANISM: Homo sapiens

<400> SEQUENCE: 20

| | | | | | |
|---|---|---|---|---|---|
| atgtgtgatc | tgccgcagac | tcactctctg | ggttctcgtc | gtactctgat | gctgctggct | 60 |
| cagatgcgtc | gtatctctct | tttctcctgc | ttgaaggaca | gacatgactt | tggatttccc | 120 |
| caggaggagt | ttggcaacca | gttccaaaag | gctgaaacca | tccctgtcct | catggatatg | 180 |
| atcctacaga | tcttcaatct | cttcagcaca | aaggactcat | ctgctgcttg | ggatgagacc | 240 |
| ctcctagaca | aattctacac | tgaactctac | cagcagctga | atgacctgga | agcctgtgtg | 300 |
| atacaggggg | tgggggtgac | agagactccc | ctgatgaagg | aggactccat | tctggctgtg | 360 |
| aggaaatact | tccaaagaat | cactctctat | ctgaaagaga | agaaatacag | cccttgtgcc | 420 |
| tgggaggttg | tcagagcaga | aatcatgaga | tcttttttctt | tgtcaacaaa | cttgcaagaa | 480 |
| agtttaagaa | gtaaggaatg | a | | | | 501 |

<210> SEQ ID NO 21
<211> LENGTH: 501
<212> TYPE: DNA
<213> ORGANISM: Homo sapiens

<400> SEQUENCE: 21

| | | | | | |
|---|---|---|---|---|---|
| atgtgtgatc | tgccgcagac | tcactctctg | ggttctcgtc | gtactctgat | gctgctggct | 60 |
| cagatgcgtc | gtatctctct | tttctcctgc | ttgaaggaca | gacatgactt | tggatttccc | 120 |
| caggaggagt | ttggcaacca | gttccaaaag | gctgaaacca | tccctgtcct | ctataacatg | 180 |
| atctctcaga | tcttcaatct | cttcagcaca | aaggactcat | ctgctgcttg | ggatgagacc | 240 |
| ctcctagaca | aattctacac | tgaactctac | cagcagctga | atgacctgga | agcctgtgtg | 300 |
| atacaggggg | tgggggtgac | agagactccc | ctgatgaagg | aggactccat | tctggctgtg | 360 |
| aggaaatact | tccaaagaat | cactctctat | ctgaaagaga | agaaatacag | cccttgtgcc | 420 |
| tgggaggttg | tcagagcaga | aatcatgaga | tcttttttctt | tgtcaacaaa | cttgcaagaa | 480 |
| agtttaagaa | gtaaggaatg | a | | | | 501 |

<210> SEQ ID NO 22

```
<211> LENGTH: 501
<212> TYPE: DNA
<213> ORGANISM: Homo sapiens

<400> SEQUENCE: 22
atgtgtgatc tgccgcagac tcactctctg ggttctcgtc gtactctgat gctgctggct      60
cagatgcgtc gtatctctct tttctcctgc ttgaaggaca gacatgactt tggatttccc     120
caggaggagt ttggcaacca gttccaaaag gctgaaacca tccctgtcct catggatatg     180
atcctacaga tcttcaatct cttcagcaca aaggactcat ctgctgcttg ggatgagacc     240
ctcctagaca aattctacac tgaactctac cagcagctga atgacctgga agcctgtgtg     300
atacagggggg tggggtgac agagactccc ctgatgaagg aggactccat tctggctgtg     360
aggaaatact tccaaagaat cactctctat ctgaaagaga agaaatacag cccttgtgcc     420
tgggaggttg tcagagcaga aatcatgaga tcttttcctt tgtcaacaaa cttgcaaaaa     480
aggttaaaaa gtaaggaatg a                                               501

<210> SEQ ID NO 23
<211> LENGTH: 501
<212> TYPE: DNA
<213> ORGANISM: Homo sapiens

<400> SEQUENCE: 23
atgtgtgatc tgccgcagac tcactctctg ggttctcgtc gtactctgat gctgctggct      60
cagatgcgtc gtatctctct tttctcctgc ttgaaggaca gacatgactt tggatttccc     120
caggaggagt ttggcaacca gttccaaaag gctgaaacca tccctgtcct ctataacatg     180
atctctcaga tcttcaatct cttcagcaca aaggactcat ctgctgcttg ggatgagacc     240
ctcctagaca aattctacac tgaactctac cagcagctga atgacctgga agcctgtgtg     300
atacagggggg tggggtgac agagactccc ctgatgaagg aggactccat tctggctgtg     360
aggaaatact tccaaagaat cactctctat ctgaaagaga agaaatacag cccttgtgcc     420
tgggaggttg tcagagcaga aatcatgaga tcttttcctt tgtcaacaaa cttgcaaaaa     480
aggttaaaaa gtaaggaatg a                                               501

<210> SEQ ID NO 24
<211> LENGTH: 165
<212> TYPE: PRT
<213> ORGANISM: Homo sapiens

<400> SEQUENCE: 24

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Ala Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
```

```
                    115                 120                 125
Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 25
<211> LENGTH: 165
<212> TYPE: PRT
<213> ORGANISM: Homo sapiens

<400> SEQUENCE: 25

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Ala Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 26
<211> LENGTH: 165
<212> TYPE: PRT
<213> ORGANISM: Homo sapiens

<400> SEQUENCE: 26

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Ala Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110
```

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 27
<211> LENGTH: 165
<212> TYPE: PRT
<213> ORGANISM: Homo sapiens

<400> SEQUENCE: 27

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 28
<211> LENGTH: 165
<212> TYPE: PRT
<213> ORGANISM: Homo sapiens

<400> SEQUENCE: 28

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Asn Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

```
Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 29
<211> LENGTH: 165
<212> TYPE: PRT
<213> ORGANISM: Homo sapiens

<400> SEQUENCE: 29

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Ser Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 30
<211> LENGTH: 501
<212> TYPE: DNA
<213> ORGANISM: Homo sapiens

<400> SEQUENCE: 30
atgtgtgatc tgccgcagac tcactctctg ggttctcgtc gtactctgat gctgctggct      60
cagatgcgtc gtatctctct tttctcctgc ttgaaggaca acatgacttt ggatttccc     120 caggaggagt ttggcaacca gttccaaaag gctgaaacca tccctgtcct cgctgagatg     180
atccagcaga tcttcaatct cttcagcaca aaggactcat ctgctgcttg ggatgagacc     240
ctcctagaca aattctacac tgaactctac cagcagctga atgacctgga agcctgtgtg     300
atacaggggg tgggggtgac agagactccc ctgatgaagg aggactccat tctggctgtg     360
aggaaatact ccaaagaat cactctctat ctgaaagaga gaaatacag cccttgtgcc      420 tgggaggttg tcagagcaga aatcatgaga tcttttttctt tgtcaacaaa cttgcaagaa     480
```

```
agtttaagaa gtaaggaatg a                                              501
```

<210> SEQ ID NO 31
<211> LENGTH: 501
<212> TYPE: DNA
<213> ORGANISM: Homo sapiens

<400> SEQUENCE: 31

```
atgtgtgatc tgccgcagac tcactctctg ggttctcgtc gtactctgat gctgctggct    60
cagatgcgtc gtatctctct tttctcctgc ttgaaggaca gacatgactt tggatttccc   120
caggaggagt ttggcaacca gttccaaaag gctgaaacca tccctgtcct ccatgcgatg   180
atccagcaga tcttcaatct cttcagcaca aaggactcat ctgctgcttg ggatgagacc   240
ctcctagaca aattctacac tgaactctac cagcagctga atgacctgga agcctgtgtg   300
atacagggggtggggtgac agagactccc ctgatgaagg aggactccat tctggctgtg   360
aggaaatact tccaaagaat cactctctat ctgaaagaga agaaatacag cccttgtgcc   420
tgggaggttg tcagagcaga aatcatgaga tcttttttctt tgtcaacaaa cttgcaagaa   480
agtttaagaa gtaaggaatg a                                              501
```

<210> SEQ ID NO 32
<211> LENGTH: 501
<212> TYPE: DNA
<213> ORGANISM: Homo sapiens

<400> SEQUENCE: 32

```
atgtgtgatc tgccgcagac tcactctctg ggttctcgtc gtactctgat gctgctggct    60
cagatgcgtc gtatctctct tttctcctgc ttgaaggaca gacatgactt tggatttccc   120
caggaggagt ttggcaacca gttccaaaag gctgaaacca tccctgtcct ccatgagatg   180
atcgcgcaga tcttcaatct cttcagcaca aaggactcat ctgctgcttg ggatgagacc   240
ctcctagaca aattctacac tgaactctac cagcagctga atgacctgga agcctgtgtg   300
atacagggggtggggtgac agagactccc ctgatgaagg aggactccat tctggctgtg   360
aggaaatact tccaaagaat cactctctat ctgaaagaga agaaatacag cccttgtgcc   420
tgggaggttg tcagagcaga aatcatgaga tcttttttctt tgtcaacaaa cttgcaagaa   480
agtttaagaa gtaaggaatg a                                              501
```

<210> SEQ ID NO 33
<211> LENGTH: 501
<212> TYPE: DNA
<213> ORGANISM: Homo sapiens

<400> SEQUENCE: 33

```
atgtgtgatc tgccgcagac tcactctctg ggttctcgtc gtactctgat gctgctggct    60
cagatgcgtc gtatctctct tttctcctgc ttgaaggaca gacatgactt tggatttccc   120
caggaggagt ttggcaacca gttccaaaag gctgaaacca tccctgtcct ctatgagatg   180
atccagcaga tcttcaatct cttcagcaca aaggactcat ctgctgcttg ggatgagacc   240
ctcctagaca aattctacac tgaactctac cagcagctga atgacctgga agcctgtgtg   300
atacagggggtggggtgac agagactccc ctgatgaagg aggactccat tctggctgtg   360
aggaaatact tccaaagaat cactctctat ctgaaagaga agaaatacag cccttgtgcc   420
tgggaggttg tcagagcaga aatcatgaga tcttttttctt tgtcaacaaa cttgcaagaa   480
agtttaagaa gtaaggaatg a                                              501
```

<210> SEQ ID NO 34
<211> LENGTH: 501
<212> TYPE: DNA
<213> ORGANISM: Homo sapiens

<400> SEQUENCE: 34

```
atgtgtgatc tgccgcagac tcactctctg ggttctcgtc gtactctgat gctgctggct    60
cagatgcgtc gtatctctct tttctcctgc ttgaaggaca gacatgactt tggatttccc   120
caggaggagt ttggcaacca gttccaaaag gctgaaacca tccctgtcct ccataacatg   180
atccagcaga tcttcaatct cttcagcaca aaggactcat ctgctgcttg ggatgagacc   240
ctcctagaca aattctacac tgaactctac cagcagctga atgacctgga agcctgtgtg   300
atacagggggg tgggggtgac agagactccc ctgatgaagg aggactccat tctggctgtg   360
aggaaatact tccaaagaat cactctctat ctgaaagaga gaaatacag cccttgtgcc    420
tgggaggttg tcagagcaga aatcatgaga tcttttttctt tgtcaacaaa cttgcaagaa   480
agtttaagaa gtaaggaatg a                                              501
```

<210> SEQ ID NO 35
<211> LENGTH: 501
<212> TYPE: DNA
<213> ORGANISM: Homo sapiens

<400> SEQUENCE: 35

```
atgtgtgatc tgccgcagac tcactctctg ggttctcgtc gtactctgat gctgctggct    60
cagatgcgtc gtatctctct tttctcctgc ttgaaggaca gacatgactt tggatttccc   120
caggaggagt ttggcaacca gttccaaaag gctgaaacca tccctgtcct ccatgagatg   180
atctctcaga tcttcaatct cttcagcaca aaggactcat ctgctgcttg ggatgagacc   240
ctcctagaca aattctacac tgaactctac cagcagctga atgacctgga agcctgtgtg   300
atacagggggg tgggggtgac agagactccc ctgatgaagg aggactccat tctggctgtg   360
aggaaatact tccaaagaat cactctctat ctgaaagaga gaaatacag cccttgtgcc    420
tgggaggttg tcagagcaga aatcatgaga tcttttttctt tgtcaacaaa cttgcaagaa   480
agtttaagaa gtaaggaatg a                                              501
```

<210> SEQ ID NO 36
<211> LENGTH: 5
<212> TYPE: PRT
<213> ORGANISM: Homo sapiens

<400> SEQUENCE: 36

Gly Tyr Leu Arg Asn
1               5

<210> SEQ ID NO 37
<211> LENGTH: 7
<212> TYPE: PRT
<213> ORGANISM: Homo sapiens

<400> SEQUENCE: 37

Lys Arg Leu Lys Ser Lys Glu
1               5

<210> SEQ ID NO 38
<211> LENGTH: 6
<212> TYPE: PRT
<213> ORGANISM: Homo sapiens

<400> SEQUENCE: 38

Lys Arg Leu Lys Ser Lys
1               5

<210> SEQ ID NO 39
<211> LENGTH: 6
<212> TYPE: PRT
<213> ORGANISM: Homo sapiens

<400> SEQUENCE: 39

Thr Asn Leu Gln Glu Ser
1               5

<210> SEQ ID NO 40
<211> LENGTH: 165
<212> TYPE: PRT
<213> ORGANISM: Homo sapiens

<400> SEQUENCE: 40

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Leu Met Ile Asp Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 41
<211> LENGTH: 165
<212> TYPE: PRT
<213> ORGANISM: Homo sapiens

<400> SEQUENCE: 41

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Ala Met Ile Ser Gln Ile Phe
    50                  55                  60

Asn Leu Phe Ser Thr Lys Asp Ser Ser Ala Ala Trp Asp Glu Thr Leu
65                  70                  75                  80

```
Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 42
<211> LENGTH: 7
<212> TYPE: PRT
<213> ORGANISM: Homo sapiens

<400> SEQUENCE: 42

Glu Ser Leu Arg Ser Lys Glu
1               5

<210> SEQ ID NO 43
<211> LENGTH: 7
<212> TYPE: PRT
<213> ORGANISM: Homo sapiens

<400> SEQUENCE: 43

Lys Arg Leu Lys Ser Lys Glu
1               5

<210> SEQ ID NO 44
<211> LENGTH: 6
<212> TYPE: PRT
<213> ORGANISM: Homo sapiens

<400> SEQUENCE: 44

Lys Arg Leu Lys Ser Lys
1               5

<210> SEQ ID NO 45
<211> LENGTH: 165
<212> TYPE: PRT
<213> ORGANISM: Homo sapiens

<400> SEQUENCE: 45

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Ala
65                  70                  75                  80

Leu Asp Lys Phe Ala Thr Glu Leu Ala Gln Gln Leu Asn Asp Leu Glu
                85                  90                  95

Ala Cys Val Ile Gln Gly Val Gly Val Thr Glu Thr Pro Leu Met Lys
            100                 105                 110
```

```
Glu Asp Ser Ile Leu Ala Val Arg Lys Tyr Phe Gln Arg Ile Thr Leu
            115                 120                 125

Tyr Leu Lys Glu Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 46
<211> LENGTH: 165
<212> TYPE: PRT
<213> ORGANISM: Homo sapiens

<400> SEQUENCE: 46

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Leu Met Ile Asp Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Lys Arg
145                 150                 155                 160

Leu Lys Ser Lys Glu
                165

<210> SEQ ID NO 47
<211> LENGTH: 165
<212> TYPE: PRT
<213> ORGANISM: Homo sapiens

<400> SEQUENCE: 47

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Ala Met Ile Ser Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
```

```
                         100                 105                 110
Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Lys Arg
145                 150                 155                 160

Leu Lys Ser Lys Glu
            165

<210> SEQ ID NO 48
<211> LENGTH: 165
<212> TYPE: PRT
<213> ORGANISM: Homo sapiens

<400> SEQUENCE: 48

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Ala
65                  70                  75                  80

Leu Asp Lys Phe Ala Thr Glu Leu Ala Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Lys Arg
145                 150                 155                 160

Leu Lys Ser Lys Glu
            165

<210> SEQ ID NO 49
<211> LENGTH: 876
<212> TYPE: DNA
<213> ORGANISM: Homo sapiens

<400> SEQUENCE: 49
agaacctaga gcccaaggtt cagagtcacc catctcagca agcccagaag tatctgcaat      60
atctacgatg gcctcgccct tgctttact gatggtcctg gtggtgctca gctgcaagtc     120
aagctgctct ctgggctgtg atctccctga gacccacagc tggataaca ggaggacctt     180 gatgctcctg gcacaaatga gcagaatctc tccttcctcc tgtctgatgg acagacatga     240
ctttggattt ccccaggagg agtttgatgg caaccagttc cagaaggctc agccatctc     300 tgtcctccat gagctgatcc agcagatctt caacctcttt accacaaaag attcatctgc     360
tgcttgggat gaggacctcc tagacaaatt ctgcaccgaa ctctaccagc agctgaatga     420
cttggaagcc tgtgtgatgc aggaggagag ggtgggagaa actccctga tgaatgcgga     480 ctccatcttg gctgtgaaga atacttccg aagaatcact ctctatctga cagagaagaa     540
```

-continued

```
atacagccct tgtgcctggg aggttgtcag agcagaaatc atgagatccc tctctttatc    600
aacaaacttg caagaaagat taaggaggaa ggaataacat ctggtccaac atgaaaacaa    660
ttcttattga ctcatacacc aggtcacgct tcatgaattc tgtcatttca aaagactctc    720 accctgcta taactatgac catgctgata aactgattta tctatttaaa tatttattta    780
actattcata agatttaaat tattttttgtt catataacgt catgtgcacc tttacactgt    840
ggttagtgta ataaaacatg ttccttatat ttactc                              876
```

<210> SEQ ID NO 50
<211> LENGTH: 23
<212> TYPE: PRT
<213> ORGANISM: Homo sapiens

<400> SEQUENCE: 50

Met Ala Leu Thr Phe Ala Leu Leu Val Ala Leu Leu Val Leu Ser Cys
1               5                   10                  15

Lys Ser Ser Cys Ser Val Gly
            20

<210> SEQ ID NO 51
<211> LENGTH: 165
<212> TYPE: PRT
<213> ORGANISM: Homo sapiens

<400> SEQUENCE: 51

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 52
<211> LENGTH: 165
<212> TYPE: PRT
<213> ORGANISM: Homo sapiens

<400> SEQUENCE: 52

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp

```
            20                  25                  30
Arg Arg Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 53
<211> LENGTH: 166
<212> TYPE: PRT
<213> ORGANISM: Homo sapiens

<400> SEQUENCE: 53

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Ala Glu Ala Ile Ser Val Leu His Glu Val Ile Gln Gln Thr
    50                  55                  60

Phe Asn Leu Phe Ser Thr Lys Asp Ser Ser Val Ala Trp Asp Glu Arg
65                  70                  75                  80

Leu Leu Asp Lys Leu Tyr Thr Glu Leu Tyr Gln Gln Leu Asn Asp Leu
                85                  90                  95

Glu Ala Cys Val Met Gln Glu Val Trp Val Gly Gly Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Ser Ser Arg Asn Leu Gln Glu
145                 150                 155                 160

Arg Leu Arg Arg Lys Glu
                165

<210> SEQ ID NO 54
<211> LENGTH: 166
<212> TYPE: PRT
<213> ORGANISM: Homo sapiens

<400> SEQUENCE: 54

Cys Asp Leu Pro Glu Thr His Ser Leu Asp Asn Arg Arg Thr Met Met
1               5                   10                  15
```

```
Leu Leu Ala Gln Met Ser Arg Ile Ser Pro Ser Ser Cys Leu Met Asp
            20                  25                  30
Arg His Asp Phe Arg Phe Pro Gln Glu Glu Phe Asp Gly Asn Gln Phe
        35                  40                  45
Gln Lys Ala Pro Ala Ile Ser Val Leu His Glu Leu Ile Gln Gln Ile
50                  55                  60
Phe Asn Leu Phe Thr Thr Lys Asp Ser Ser Ala Ala Trp Asp Glu Asp
65                  70                  75                  80
Leu Leu Asp Lys Phe Cys Thr Glu Leu Tyr Gln Gln Leu Asn Asp Leu
                85                  90                  95
Glu Ala Cys Val Met Gln Glu Arg Val Gly Glu Thr Pro Leu Met
            100                 105                 110
Asn Ala Asp Ser Ile Leu Ala Val Lys Lys Tyr Phe Arg Arg Ile Thr
            115                 120                 125
Leu Tyr Leu Thr Glu Lys Lys Tyr Ser Pro Cys Ala Trp Glu Val Val
            130                 135                 140
Arg Ala Glu Ile Met Arg Ser Leu Ser Leu Ser Thr Asn Leu Gln Glu
145                 150                 155                 160
Arg Leu Arg Arg Lys Glu
                165

<210> SEQ ID NO 55
<211> LENGTH: 167
<212> TYPE: PRT
<213> ORGANISM: Homo sapiens

<400> SEQUENCE: 55

Cys Asp Leu Pro Gln Thr His Ser Leu Gly Asn Arg Arg Ala Leu Ile
1               5                   10                  15
Leu Leu Ala Gln Met Gly Arg Ile Ser Pro Phe Ser Cys Leu Lys Asp
            20                  25                  30
Arg His Asp Phe Gly Phe Pro Gln Glu Glu Phe Asp Gly Asn Gln Phe
        35                  40                  45
Gln Lys Ala Gln Ala Ile Ser Val Leu His Glu Met Ile Gln Gln Thr
50                  55                  60
Phe Asn Leu Phe Ser Thr Lys Asp Ser Ser Ala Thr Trp Glu Gln Ser
65                  70                  75                  80
Leu Leu Glu Lys Phe Ser Thr Glu Leu Asn Gln Gln Leu Asn Asp Met
                85                  90                  95
Glu Ala Cys Val Ile Gln Glu Val Gly Val Glu Thr Pro Leu Met
            100                 105                 110
Asn Val Asp Ser Ile Leu Ala Val Lys Lys Tyr Phe Gln Arg Ile Thr
            115                 120                 125
Leu Tyr Leu Thr Glu Lys Lys Tyr Ser Pro Cys Ala Trp Glu Val Val
            130                 135                 140
Arg Ala Glu Ile Met Arg Ser Phe Ser Leu Ser Lys Ile Phe Gln Glu
145                 150                 155                 160
Arg Leu Arg Arg Lys Glu Glx
                165

<210> SEQ ID NO 56
<211> LENGTH: 166
<212> TYPE: PRT
<213> ORGANISM: Homo sapiens

<400> SEQUENCE: 56
```

```
Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
            20                  25                  30

Arg His Asp Phe Gly Phe Pro Glu Glu Glu Phe Asp Gly His Gln Phe
            35                  40                  45

Gln Lys Thr Gln Ala Ile Ser Val Leu His Glu Met Ile Gln Gln Thr
50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
            85                  90                  95

Glu Ala Cys Val Ile Gln Glu Val Gly Val Glu Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 57
<211> LENGTH: 166
<212> TYPE: PRT
<213> ORGANISM: Homo sapiens

<400> SEQUENCE: 57

Cys Asp Leu Pro Gln Thr His Ser Leu Arg Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Glu Phe Arg Phe Pro Glu Glu Glu Phe Asp Gly His Gln Phe
            35                  40                  45

Gln Lys Thr Gln Ala Ile Ser Val Leu His Glu Met Ile Gln Gln Thr
50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
            85                  90                  95

Glu Ala Cys Val Ile Gln Glu Val Gly Val Glu Glu Thr Pro Leu Met
            100                 105                 110

Asn Glu Asp Phe Ile Leu Ala Val Arg Lys Tyr Phe Gln Arg Ile Thr
            115                 120                 125

Leu Tyr Leu Met Glu Lys Lys Tyr Ser Pro Cys Ala Trp Glu Val Val
130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 58
<211> LENGTH: 166
<212> TYPE: PRT
<213> ORGANISM: Homo sapiens
```

<400> SEQUENCE: 58

```
Cys Asp Leu Pro Gln Thr His Ser Leu Gly Asn Arg Arg Ala Leu Ile
1               5                   10                  15

Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Ile Glu Arg Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Glu
                165
```

<210> SEQ ID NO 59
<211> LENGTH: 166
<212> TYPE: PRT
<213> ORGANISM: Homo sapiens

<400> SEQUENCE: 59

```
Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Glu Phe Pro Gln Glu Glu Phe Asp Gly Asn Gln Phe
        35                  40                  45

Gln Lys Ala Gln Ala Ile Ser Val Leu His Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Lys Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
                165
```

<210> SEQ ID NO 60
<211> LENGTH: 166
<212> TYPE: PRT

<213> ORGANISM: Homo sapiens

<400> SEQUENCE: 60

```
Cys Asp Leu Pro Gln Thr His Ser Leu Gly Asn Arg Arg Ala Leu Ile
1               5                   10                  15
Leu Leu Ala Gln Met Gly Arg Ile Ser His Phe Ser Cys Leu Lys Asp
            20                  25                  30
Arg Tyr Asp Phe Gly Phe Pro Gln Glu Val Phe Asp Gly Asn Gln Phe
        35                  40                  45
Gln Lys Ala Gln Ala Ile Ser Ala Phe His Glu Met Ile Gln Gln Thr
    50                  55                  60
Phe Asn Leu Phe Ser Thr Lys Asp Ser Ser Ala Ala Trp Asp Glu Thr
65                  70                  75                  80
Leu Leu Asp Lys Phe Tyr Ile Glu Leu Phe Gln Gln Leu Asn Asp Leu
                85                  90                  95
Glu Ala Cys Val Thr Gln Glu Val Gly Val Glu Glu Ile Ala Leu Met
            100                 105                 110
Asn Glu Asp Ser Ile Leu Ala Val Arg Lys Tyr Phe Gln Arg Ile Thr
        115                 120                 125
Leu Tyr Leu Met Gly Lys Lys Tyr Ser Pro Cys Ala Trp Glu Val Val
    130                 135                 140
Arg Ala Glu Ile Met Arg Ser Phe Ser Phe Ser Thr Asn Leu Gln Lys
145                 150                 155                 160
Gly Leu Arg Arg Lys Glu
                165
```

<210> SEQ ID NO 61
<211> LENGTH: 166
<212> TYPE: PRT
<213> ORGANISM: Homo sapiens

<400> SEQUENCE: 61

```
Cys Asp Leu Pro Gln Thr His Ser Leu Gly Asn Arg Arg Ala Leu Ile
1               5                   10                  15
Leu Leu Ala Gln Met Arg Arg Ile Ser Pro Phe Ser Cys Leu Lys Asp
            20                  25                  30
Arg His Asp Phe Glu Phe Pro Gln Glu Glu Phe Asp Asp Lys Gln Phe
        35                  40                  45
Gln Lys Ala Gln Ala Ile Ser Val Leu His Glu Met Ile Gln Gln Thr
    50                  55                  60
Phe Asn Leu Phe Ser Thr Lys Asp Ser Ser Ala Ala Leu Asp Glu Thr
65                  70                  75                  80
Leu Leu Asp Glu Phe Tyr Ile Glu Leu Asp Gln Gln Leu Asn Asp Leu
                85                  90                  95
Glu Ser Cys Val Met Gln Glu Val Gly Val Ile Glu Ser Pro Leu Met
            100                 105                 110
Tyr Glu Asp Ser Ile Leu Ala Val Arg Lys Tyr Phe Gln Arg Ile Thr
        115                 120                 125
Leu Tyr Leu Thr Glu Lys Lys Tyr Ser Ser Cys Ala Trp Glu Val Val
    130                 135                 140
Arg Ala Glu Ile Met Arg Ser Phe Ser Leu Ser Ile Asn Leu Gln Lys
145                 150                 155                 160
Arg Leu Lys Ser Lys Glu
                165
```

<210> SEQ ID NO 62

-continued

```
<211> LENGTH: 172
<212> TYPE: PRT
<213> ORGANISM: Homo sapiens

<400> SEQUENCE: 62

Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
            20                  25                  30

Arg Arg Asp Phe Arg Phe Pro Gln Glu Met Val Lys Gly Ser Gln Leu
        35                  40                  45

Gln Lys Ala His Val Met Ser Val Leu His Glu Met Leu Gln Gln Ile
    50                  55                  60

Phe Ser Leu Phe His Thr Glu Arg Ser Ser Ala Ala Trp Asn Met Thr
65                  70                  75                  80

Leu Leu Asp Gln Leu His Thr Gly Leu His Gln Gln Leu Gln His Leu
                85                  90                  95

Glu Thr Cys Leu Leu Gln Val Val Gly Glu Gly Glu Ser Ala Gly Ala
            100                 105                 110

Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val
    130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser Ser
                165                 170
```

RECOMBINANT INTERFERON α2 (IFNα2) MUTANTS AND METHODS OF USE THEREOF

CROSS-REFERENCE TO RELATED APPLICATIONS

This application is a continuation-in-part of U.S. application Ser. No. 11/994,159 filed Apr. 30, 2008 now U.S. Pat. No. 7,767,799 which is the US National Phase 371 filing of International Patent Application PCT/IL2006/000754 filed Jun. 28, 2006, which in turn claims the benefit of application No. 60/694,810 filed Jun. 29, 2005, the entire contents of each of which are expressly incorporated herein by reference thereto.

FIELD OF THE INVENTION

The present invention provides IFNα2 mutants and active fragments, analogs, derivatives, and variants thereof, nucleotide molecules encoding same, pharmaceutical compositions comprising same, and methods utilizing same for treating cancer, infectious diseases, and autoimmune diseases.

BACKGROUND OF THE INVENTION

Interferons (IFNs) were discovered in 1957 by Isaacs and Lindenmann (Proc R Soc Lond B Biol Sci 147(927):258-67) and were named for their ability to interfere with viral proliferation. Interferons can also combat bacterial and parasitic infections and promote a wide range of activities, including inhibition of cell growth, differentiation, and spontaneous apoptosis, and modulation of the immune system, including promotion of antigen presentation, induction of cytokine production, and promotion of T cell maturation and clonal propagation. IFNs were originally classified by their sources: leukocytes IFN-α-1 (SEQ ID NO: 1), and IFN-α-2 (SEQ ID NO: 2), fibroblasts IFN-β (SEQ ID NO: 3), and immune cells IFN-γ (SEQ ID NO: 4).

Type I and Type II Interferons are defined based on their receptor specificity. Type I interferons are a family of monomeric proteins including IFNα, IFNω, IFNβ, and IFNτ that has been described only in ungulate species. The only known type II interferon is the dimeric IFNγ.

Human type I interferons number 13 distinct non-allelic alpha proteins, one beta, and one omega. Each member is a mature protein of 165 or 166 amino acid residues, all sharing the same structure, having 2 conserved disulfide bonds, Cys1-Cys98 and Cys29-Cys138, and binding the same cell surface receptor, IFNAR.

A high level of sequence homology (80%) is displayed among the various interferon alpha sub-types, and about 35% homology exists between these sub-types and IFNβ. In spite of the high homology of the different sub-types, their biological activities differ notably. For example, IFNβ has a much higher anti-proliferative activity then IFNα proteins, due to the tighter binding of IFNβ to the IFNAR1 receptor subunit.

All type I interferons signal through a common receptor complex known as "interferon receptor 1" ("IFNAR"), in the context of a "ternary complex" containing IFN and the subunits IFNAR1 and IFNAR2. Binding of IFNα2 to IFNAR1 alone is relatively weak, namely, 1.5-5 µM, in contrast to the ~10 nM binding affinity for IFNAR2. The formation of the ternary complex occurs in a sequential mode, with an intermediate complex first forming between interferon and IFNAR2, followed by the recruitment of IFNAR1 in a 1:1:1 stoichiometry. Because of cooperative binding to the 2 surface-bound receptor subunits, the apparent ligand binding affinity is higher than binding to IFNAR2 alone, and depends on the relative and absolute receptor surface concentrations (Lamken, P. et al., 2004, *J Mol Biol* 341, 303-318). Association of IFNAR1 and IFNAR2 stimulates the activation of the constitutively-associated intracellular kinases Jak1 and Tyk2, leading to a tyrosine phosphorylation cascade that results in the dimerization and transport into the nucleus of the signal transducers and activators of transcription (STATs), where they bind to specific DNA sequences and stimulate transcription of hundreds of responsive genes.

The structures of several type I interferons are known, including murine IFNβ (1IFA, 1RMI), human IFNβ (1AU1), human IFNα2 (1RH2, 1ITF), and ovine IFNτ (1B5L). Structurally, interferons are members of the α-helical cytokine family. The extracellular part of IFNAR2 consists of 2 immunoglobulin-like domains, with the IFNα2 binding site located at the N-terminal domain and the connecting loop. Mature IFNAR1 is a 530 amino acid protein, with a 21-residue transmembrane segment and a 100-residue cytoplasmic domain. The sequence suggests that its extracellular portion is composed of 4 immunoglobulin-like domains. The IFNAR1 binding site of IFNβ is located on the B, C, and D helices and the DE loop, in the case of IFNα2, it is located on helices B and C (Hu R et al, Human IFN-alpha protein engineering: the amino acid residues at positions 86 and 90 are important for antiproliferative activity. J Immunol 167(3):1482-9, 2001).

In general, IFNβ exhibits an additional repertoire of activities over IFNα. IFNβ has generally higher activity in transcriptionally activating IFN responsive genes, and is active at lower concentrations than IFNα. Affinity for IFNAR1 is likely to be the key difference between IFNα2 and IFNβ (Jaitin, 2006. *Mol Cell Biol*. 26, 1888-1897).

Recombinant IFNα2 protein exhibits anti-cancer effects. However, IFNα2 treatment is not always effective and can result in intolerable side effects. WO 97/12630 and WO 01/54678 disclose treatment of cancer patients with a temozolomide/IFN combination.

Hepatitis C virus (HCV) is the most common chronic blood-borne infection in the United States. Chronic liver disease is the tenth leading cause of death among adults in the United States, and an estimated 40% of chronic liver disease is HCV-related. HCV-associated end-stage liver disease is the most frequent indication for liver transplantation among adults. Antiviral therapy of chronic hepatitis C with recombinant IFN has improved rapidly over the last decade. Nevertheless, even with the latest regimens, combination therapy with pegylated IFN-α plus ribavirin, 40% to 50% of patients fail therapy, i.e. do not respond or relapse. These patients have no effective therapeutic alternative.

There remains an unmet medical need for IFNAR agonists of enhanced potency for treating cancer and infectious disease, e.g. HCV.

Type I diabetes, also known as autoimmune diabetes or insulin-dependent diabetes mellitus (IDDM), is an autoimmune disease characterized by the selective destruction of pancreatic cells by autoreactive T lymphocytes. IFN-α has also been implicated in the pathogenesis of systemic lupus erythematosus (SLE) (Ytterberg and Schnitzer, Arthritis Rheum 25: 401-406, 1982). IFN-α has been implicated in IDDM pathogenesis; thus, antagonists of IFN-α and -β signaling are useful in treating IDDM and SLE, as disclosed in WO 93/04699 and WO 02/066649, respectively.

There remains an unmet medical need for potent IFNAR antagonists for treating autoimmune diseases, e.g. IDDM.

Multiple sclerosis (MS) is a chronic, neurological, autoimmune disease that can cause impaired vision and muscular degeneration. IFN-β-1a and β-1b are both approved for treating MS. Therapeutic effect of IFN-β is likely to be due to skewing of the T-cell response towards a type 2 phenotype (Zafranskaya M et al, Interferon-beta therapy reduces CD4+ and CD8+ T-cell reactivity in multiple sclerosis. Immunology 121(1):29-39, 2007).

LE is an autoimmune disease that causes inflammation and damage to various body tissues and parts, including joints, kidneys, heart, lungs, brain, blood vessels, and skin. The most common symptoms of LE include achy or swollen joints (arthritis), fever, prolonged or extreme fatigue, skin rashes and kidney problems. The goals of effective treatment of LE are to prevent flares, minimize organ damage and complications, and maintain normal bodily functions. Because of the limited success of currently available medications and their potentially serious side effects, it is important to provide an alternative effective treatment for LE.

There remains an unmet medical need for IFN-β analogues of enhanced potency for treating MS and other auto-immune diseases with similar pathology.

US Patent Application Publication No. 2004/0230040 discloses IFN-α2 variants with added cysteine residues. US Patent Application Publication No. 2004/0002474 discloses α interferon homologues with anti-proliferative activity. These IFN-α2 variants are unrelated to the IFN-α2 variants of the present invention.

SUMMARY OF THE INVENTION

The present invention provides IFNα2 mutants and active fragments, analogs, derivatives, and variants thereof, nucleotide molecules encoding same, pharmaceutical compositions comprising same, and methods utilizing same for treating cancer, infectious diseases, and autoimmune diseases.

In one embodiment, the present invention provides a mutated interferon α2 (IFNα2) polypeptide, comprising a mutation selected from the group consisting of (a) mutation of the histidine at position 57 (H57) to a residue selected from the group consisting of tyrosine and methionine; (b) mutation of the glutamate at position 58 (E58) to a residue selected from the group consisting of asparagine, aspartate, leucine, and alanine; and (c) mutation of the glutamine at position 61 (Q61) to a residue selected from the group consisting of serine, leucine, and aspartate; and combinations thereof. Preferably, the mutated IFNα2 polypeptide is a recombinant polypeptide. More preferably, the mutation increases affinity of the mutated IFNα2 polypeptide for the IFNAR1 subunit of the interferon receptor 1 ("IFNAR") (e.g. a human IFNAR), relative to wt IFNα2. Each possibility represents a separate embodiment of the present invention.

In another embodiment, the present invention provides a mutated IFNα2 polypeptide comprising a mutation selected from the group consisting of (a) mutation of H57; (b) mutation of E58; and (c) mutation of Q61; (d) mutation of the asparagine at position 65 (N65); (e) mutation of the leucine at position 80 (L80); (f) mutation of the tyrosine at position 85 (Y85); and (g) mutation of the tyrosine at position 89 (Y89); and combinations thereof, wherein the mutation decreases affinity of the mutated IFNα2 polypeptide for the IFNAR1 subunit of IFNAR (e.g. a human IFNAR). Preferably, the mutated IFNα2 polypeptide is a recombinant polypeptide. More preferably, the mutated IFNα2 polypeptide exhibits IFNAR antagonist activity. Each possibility represents a separate embodiment of the present invention.

In another embodiment, a mutated IFNα2 polypeptide of the present invention further comprises an additional mutation, aside from the aforementioned mutations at residues H57, E58, Q61, N65, L80, Y85, and/or Y89. In another embodiment, the additional mutation is in the C-terminal tail. In another embodiment, the additional mutation is a mutation of a residue selected from the group consisting of (a) the glutamate at position 159 (E159), (b) the serine at position 160 (S160), (c) the leucine at position 161 (L161), (d) the serine at position 163 (S163), and (e) the glutamate at position 165 (E165) to a residue selected from lysine and arginine. In another embodiment, a negative or neutral residue among the 7 carboxy-terminal residues of the IFNα2 protein is mutated to a residue selected from lysine and arginine. In another embodiment, the additional mutation increases affinity of the mutated IFNα2 polypeptide for the IFNAR2 subunit of the IFNAR (e.g. a human INFAR). Each possibility represents a separate embodiment of the present invention.

In another embodiment, the present invention provides a mutated IFNα2 polypeptide comprising both (a) a gain-of-function mutation for IFNAR1 binding in residues H57, E58, and/or Q61; and (b) a gain-of-function tail mutation for IFNAR2 binding. As provided herein, affinity of IFN proteins for IFNAR is determined by additive contributions of IFNAR1 binding and IFNAR2 binding. Thus, the present invention shows that combination of these two mutations (a) and (b) further enhances IFNAR binding, IFNAR signaling, and biological activity, relative to mutated IFNα2 polypeptides having either (a) or (b) alone.

In another embodiment, the present invention provides a mutated IFNα2 polypeptide comprising both (a) a loss-of-function mutation for IFNAR1-binding in residues H57, E58, Q61, N65, L80, Y85, and/or Y89; and (b) a gain-of-function tail mutation for IFNAR2 binding. As provided herein, Type I interferons first bind IFNAR2, then transiently recruit IFNAR1 to the complex, forming the ternary complex which mediates signaling. Occupancy of IFNAR2 by a mutated IFNα2 polypeptide thus antagonizes IFNAR signaling by preventing binding of signaling-competent IFN to the receptor. The effect is enhanced by gain-of-function tail mutations for IFNAR2 binding, which increase occupancy of IFNAR2 by the mutated IFNα2 polypeptide. Thus, the present invention shows that combination of these two mutations (a) and (b) further enhances IFNAR antagonist activity by mutated IFNα2 polypeptides of the present invention, relative to mutated IFNα2 polypeptides having either (a) or (b) alone.

In another embodiment, a mutated IFNα2 polypeptide of methods and compositions of the present invention further comprises an additional mutation in a residue selected from (a) leucine at position 30 (L30), (b) arginine at position 33 (R33), (c) methionine at position 148 (M148), and (d) serine at position 153 (S153), and combinations thereof, wherein the additional mutation decreases affinity of the mutated IFNα2 polypeptide for the IFNAR2 subunit of the IFNAR (e.g. a human IFNAR. In another embodiment, the residue is mutated to an alanine residue. In another embodiment, the mutated IFNα2 polypeptide comprises 1 of mutations (a-d). In another embodiment, the mutated IFNα2 polypeptide comprises 2 of mutations (a-d). In another embodiment, the mutated IFNα2 polypeptide comprises more than 1 of mutations (a-d). Each possibility represents a separate embodiment of the present invention.

In another embodiment, the present invention provides a nucleotide molecule (e.g. a DNA molecule, RNA molecule, or other type of nucleotide molecule) encoding a mutated IFNα2 polypeptide of the present invention. In another embodiment, the present invention provides a pharmaceutical composition comprising a nucleotide molecule of the present invention. In another embodiment, the present invention provides a vector comprising a nucleotide molecule of the present invention. Preferably, the vector is capable of expressing a mutant IFNα2 polypeptide in a prokaryotic host cell or eukaryotic host cell. In another embodiment, the present invention provides a pharmaceutical composition comprising a vector of the present invention. In another embodiment, the present invention provides a host cell comprising a nucleotide molecule of the present invention. In another embodiment, the present invention provides a pharmaceutical composition comprising a host cell of the present invention. In another embodiment, the vector is operably linked to one or more transcription control elements. Each possibility represents a separate embodiment of the present invention.

In another embodiment, the present invention provides a pharmaceutical composition comprising as an active ingredient a mutated IFNα2 polypeptide of the present invention, and further comprising a pharmaceutically acceptable carrier.

In another embodiment, the present invention provides a method of treating or ameliorating a cancer or infectious disease in a subject in need thereof, wherein the cancer or infectious disease is known to be responsive to treatment with recombinant interferon-beta, the method comprising the step of administering to the subject a pharmaceutical composition containing an IFNAR-agonistic mutant IFNα2 polypeptide of the present invention, thereby treating or ameliorating a cancer a subject in need thereof.

In another embodiment, the present invention provides a method of treating or ameliorating an autoimmune disease in a subject in need thereof, wherein the autoimmune disease is a disease known to be responsive to treatment with recombinant interferon-beta, the method comprising the step of administering to the subject the pharmaceutical composition containing an IFNAR-agonistic mutant IFNα2 polypeptide of the present invention, thereby treating or ameliorating an autoimmune disease in a subject in need thereof a disease known to be responsive to treatment with IFNAR agonists.

In another embodiment, the present invention provides mutated interferon α2 (IFNα2) polypeptide, comprising a mutation of a residue selected from the group consisting of E159, S160, L161, S163, and E165, and combinations thereof, to a residue selected from the group consisting of lysine and arginine.

In another embodiment, the present invention provides mutated interferon α2 (IFNα2) polypeptide, comprising a substitution mutation of the 5-10 C-terminal residues of the mutated IFNα2 polypeptide to a sequence selected from the group consisting of KRLKSKE (SEQ ID NO: 43) and KRLKSK (SEQ ID NO: 44).

These and other embodiments of the present invention will become apparent in conjunction with the figures, description and claims that follow.

BRIEF DESCRIPTION OF THE FIGURES

FIG. 1A shows a binding curve for capturing IFNAR1 with immobilized mAb DB2, followed by cross-linking with mAb AA3. Vertical axis for all charts is the signal (nm). FIG. 1B shows the steady state affinity analysis. Binding of IFNα2 E58A (right set of number labels) and E96A (left set of number labels) at different concentrations between 0.25 and 4 μM, as indicated, to surface-immobilized IFNAR1. Measured signal is shift in the interference spectrum (in nm) over time. FIG. 1C shows the fitting of the equilibrium signal obtained in (b) to equation (1). $K_D$ values for E58A and E96A are, =3.2±0.1 (residual error of the fitting curve) and 0.35±0.02 μM, respectively.

FIGS. 2A and 2B: FIG. 2A shows a mutant analysis of IFNAR1 and IFNAR2 binding to IFNα2. Type I interferons are aligned relative to IFNα2. Underlined residues are those for which mutation to Ala did not change binding to either receptor. "+" and "−" signs indicate whether the mutation increased or decreased binding affinity of IFNα2 (see Table 1). Number above indicates whether change is due to IFNAR1 (1) or IFNAR2 (2) binding. C-terminal residues on IFNα8 are bolded to mark changes made in SEQ ID NO: 7. Boxed residues are those relating to SEQ ID NO: 5-13. FIG. 2B shows the binding affinity of IFNα2 mutant proteins for both IFNAR1 and IFNAR2.

FIG. 3A shows a comparison of dissociation kinetics of site-specifically fluorescently labeled wt IFN-α2 (bottom curve), IFN-β (top curve), and HEQ (middle curve) from IFNAR1-EC alone bound to the surface. The inset zooms into the first 8 s of the reaction. FIGS. 3B through 3D show the Dissociation of wt IFN-α2 (B), IFN-β (C), and HEQ (D) from the ternary complex, with both IFNAR1-EC and IFNAR2-EC bound to the surface, at IFNAR1-EC receptor surface concentrations of 4 (top curve), 2 (middle curve), and 1 (bottom curve) fmol/mm². While these three curves are sharply distinguishable for wt IFN-α2, they are close together for IFN-β and superimposable for HEQ. Dotted line depicts dissociation from IFNAR2-EC alone.

FIGS. 4A and 4B show raw traces. FIG. 4C shows a plot of observed association rate ($k_{obs}$) as determined by exponential fit of the association phase of the data versus protein concentration. Slope of the linear fit of this plot gives the association rate constant ($k_{on}$), while the intercept should approximates $k_{off}$. y=(a) 0.031655+1.0742 e+06x and (b) −0.0039104+2.4367 e+06x. FIG. 4D is similar to (c), however, $k_{obs}$ was determined in a stopped-flow apparatus by pseudo-first-order mixing of the 2 proteins (IFNα2 wt was in at least fivefold excess over IFNAR2 wt). y=4.2607+1.0274 e+07x; R=0.94435 FIG. 4E is similar to FIG. 4D, but shows second-order conditions where the concentration of both proteins was 0.5 μM. FIG. 4F shows a comparison of association curves under second-order conditions for binding of IFN proteins to wt IFNAR2.

Figure 4A:
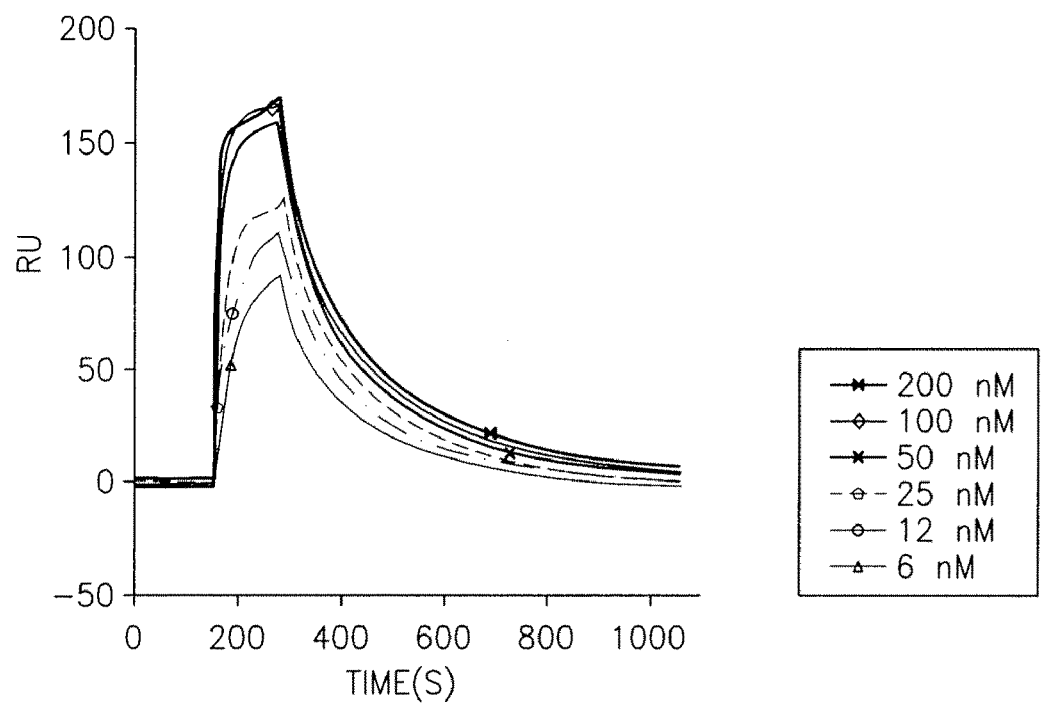
FIGS. 4A through 4F show the binding of wt IFNα2 and α8-tail to IFNAR2, as assessed on a ProteOn apparatus at 6 different protein concentrations (a)-(c) and in a stopped-flow apparatus (d)-(f).
Figure 4B:
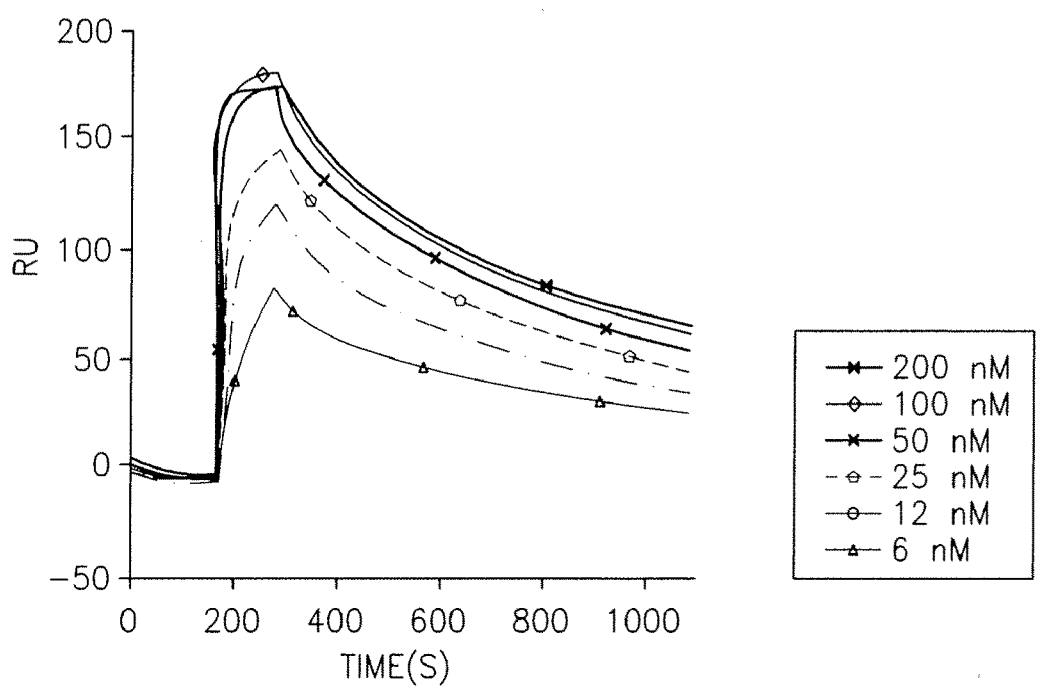
Figure 4C:
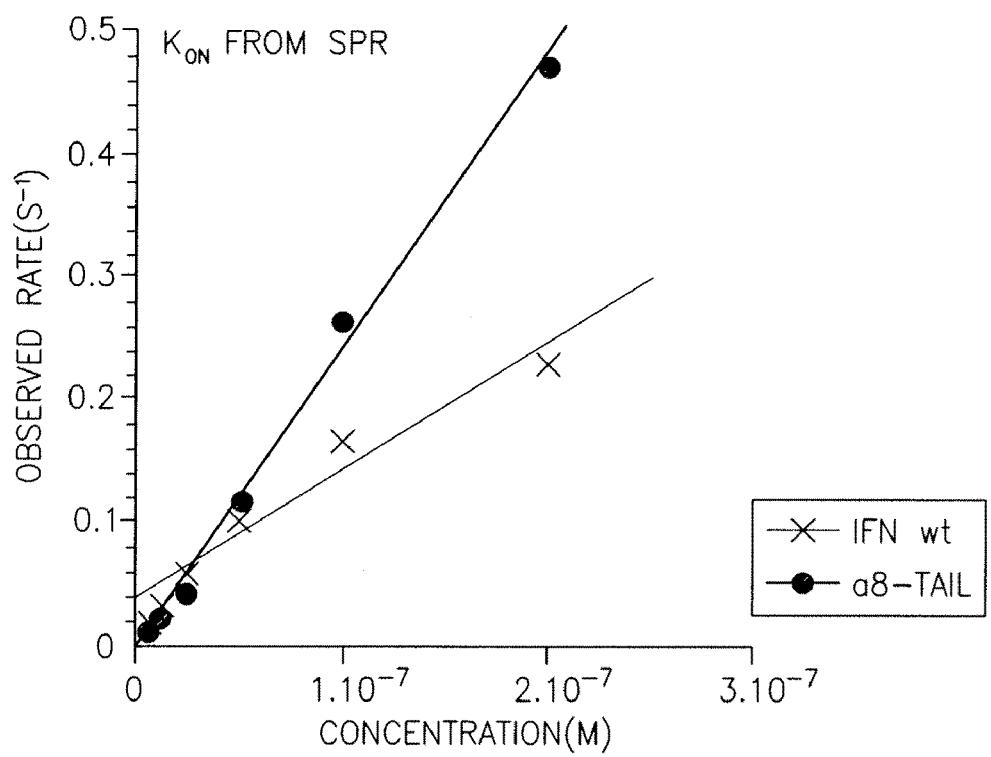
Figure 4D:
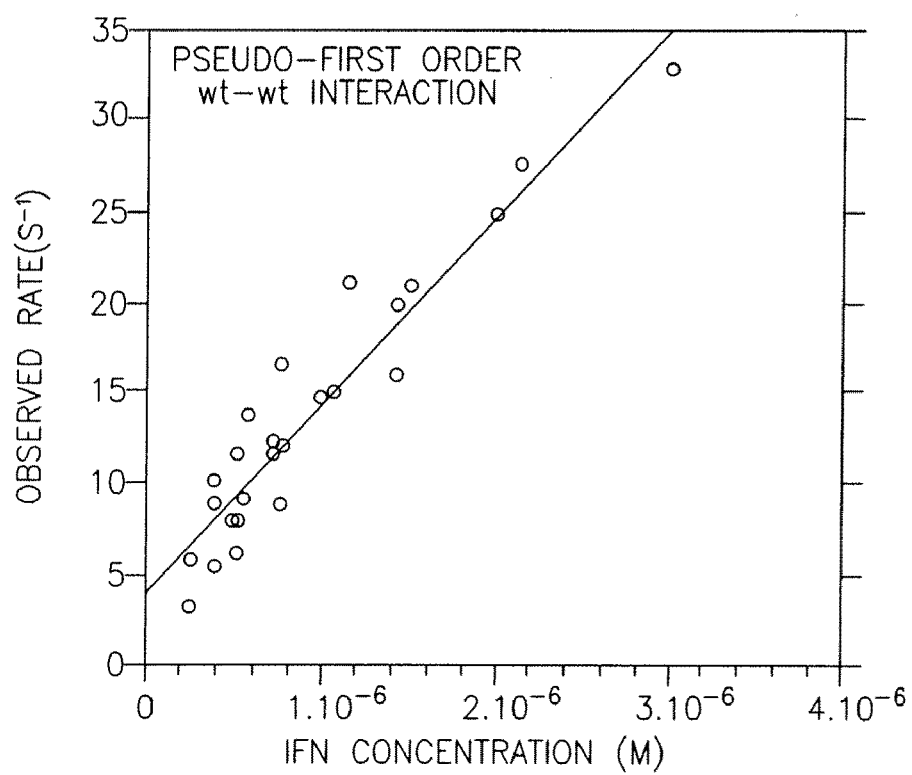
Figure 4E:
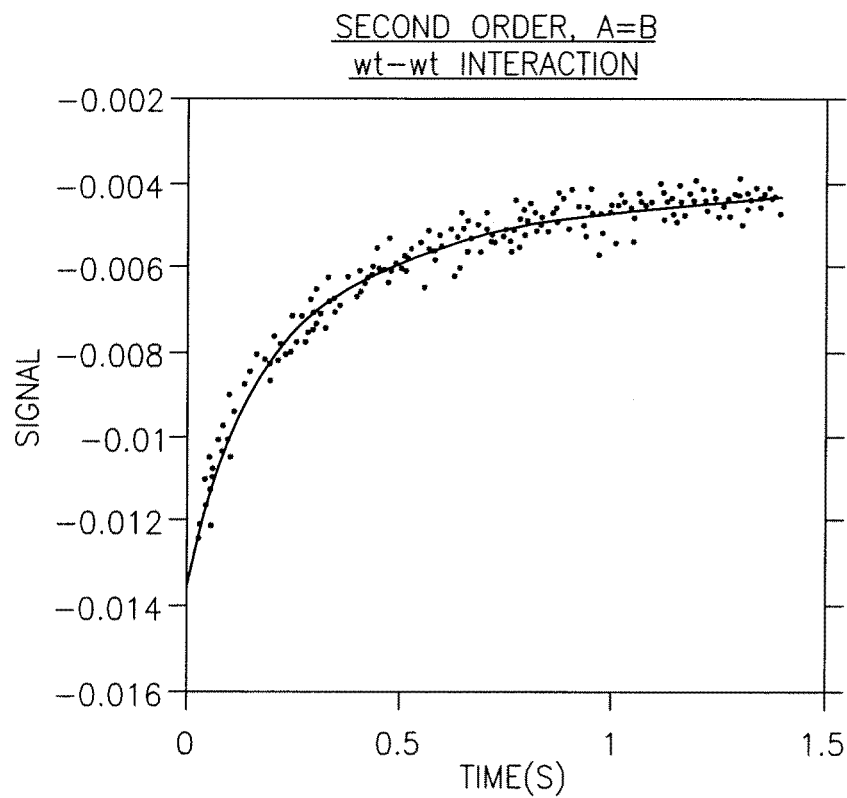
Figure 4F:
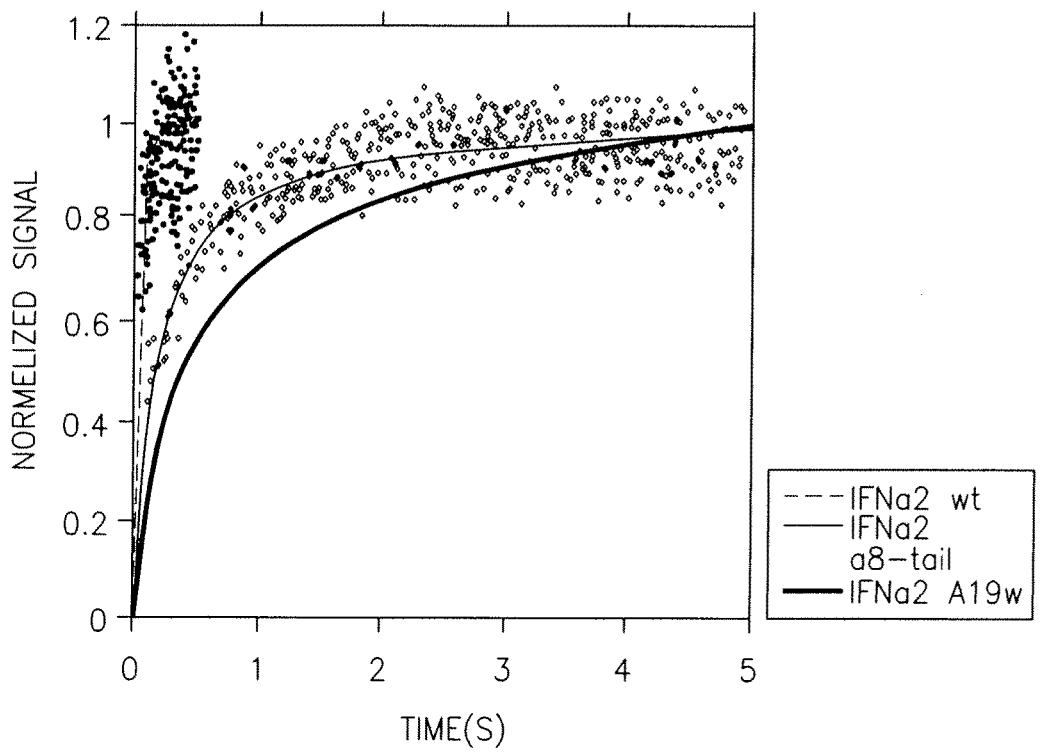

Values from FIG. 4E:

| Y = m1 + (m2*5e−7 * m3*m0)/1+ . . . | | |
|---|---|---|
| | Value | Error |
| m1 | −0.013769 | 0.0001483 |
| m2 | 0.010719 | 0.00012579 |
| m3 ($k_{on}$) | 1.1026e+07 | 4.9402e+05 |
| Chisq | 3.285e−05 | NA |
| r | 0.98573 | NA |

Figure 5A:
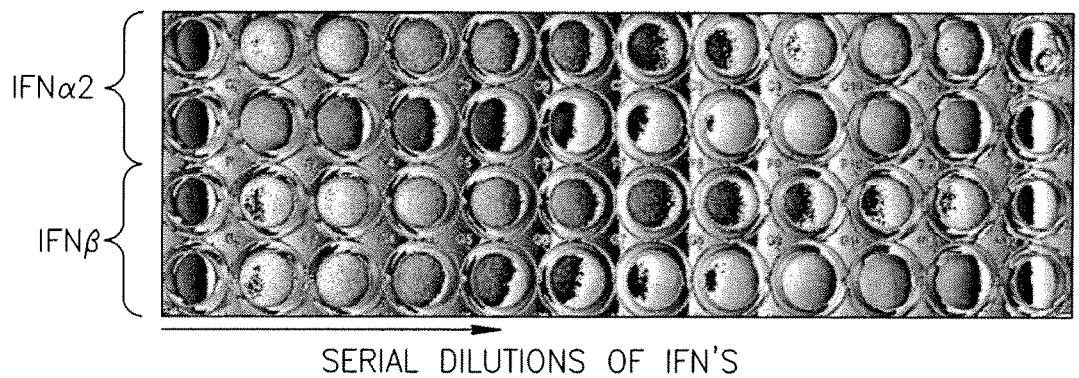
Figure 5B:
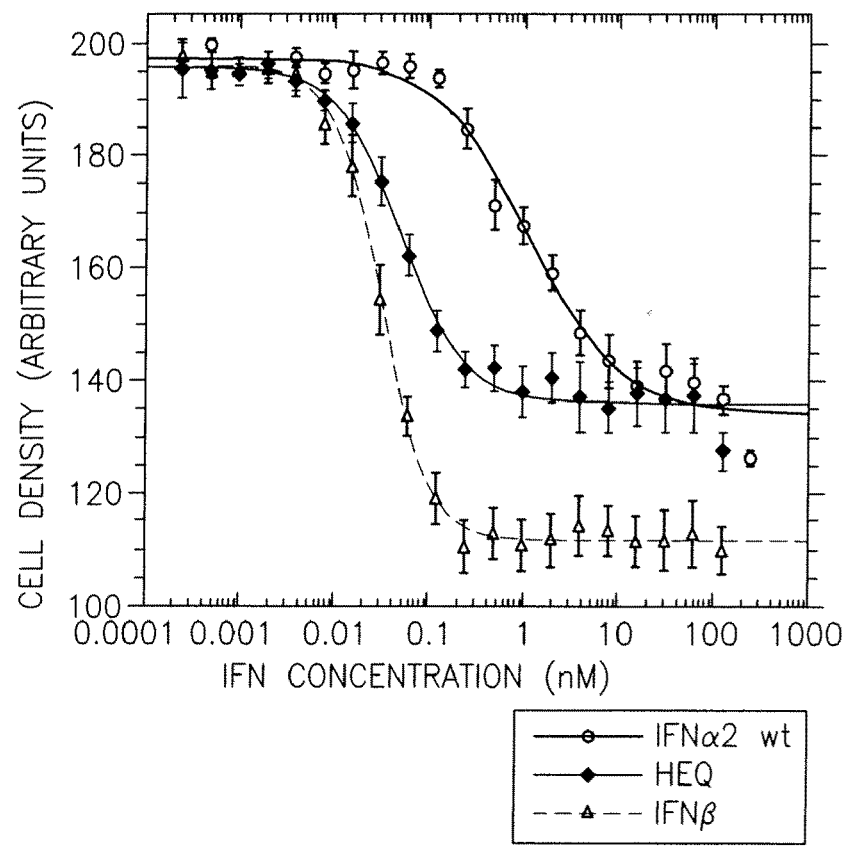
Figure 5C:
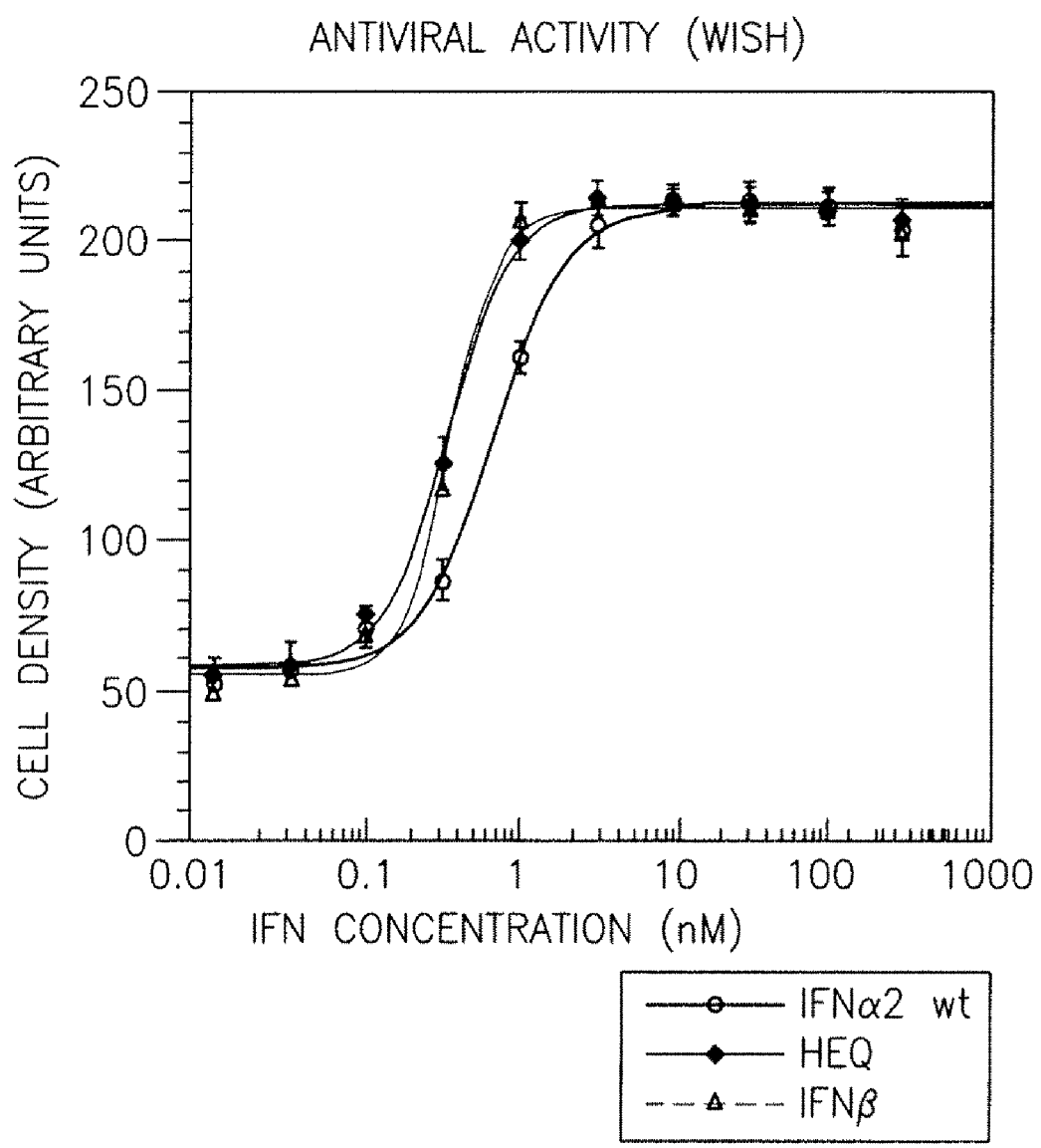

FIGS. 5A through 5C show the concentration dependence of antiviral and anti-proliferative responses of interferons on WISH cells. FIG. 5A shows the anti-proliferative response in the presence of serially diluted IFNα2 (250 nM-0.48 pM) and IFNβ (125 nM-0.24 pM). FIGS. 5B and 5C show the mean (n=6) and standard error densitometry readings for 3 independent anti-proliferative (B) and antiviral (C) experiments, including HEQ. Curves were fitted to a dose response equation and represent the best fit for the combined data.

Figure 6:
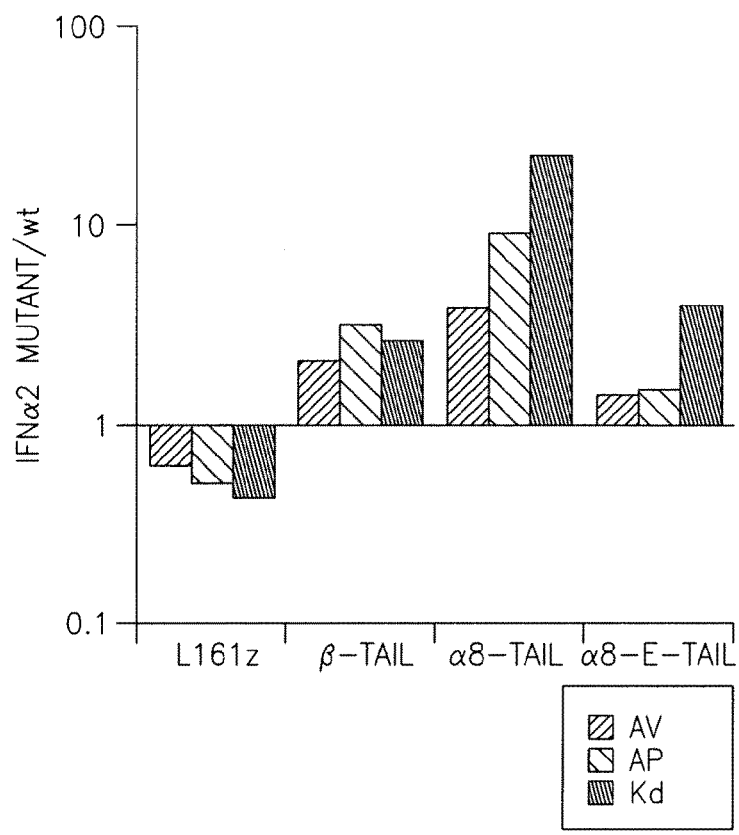

FIG. 6 shows the antiviral (AV) and anti-proliferative (AP) activities (IC$_{50}$) of IFNα2 mutants relative to wild-type in WISH cells and binding affinities for IFNAR2 (K$_D$) of the mutants.

Figure 7:
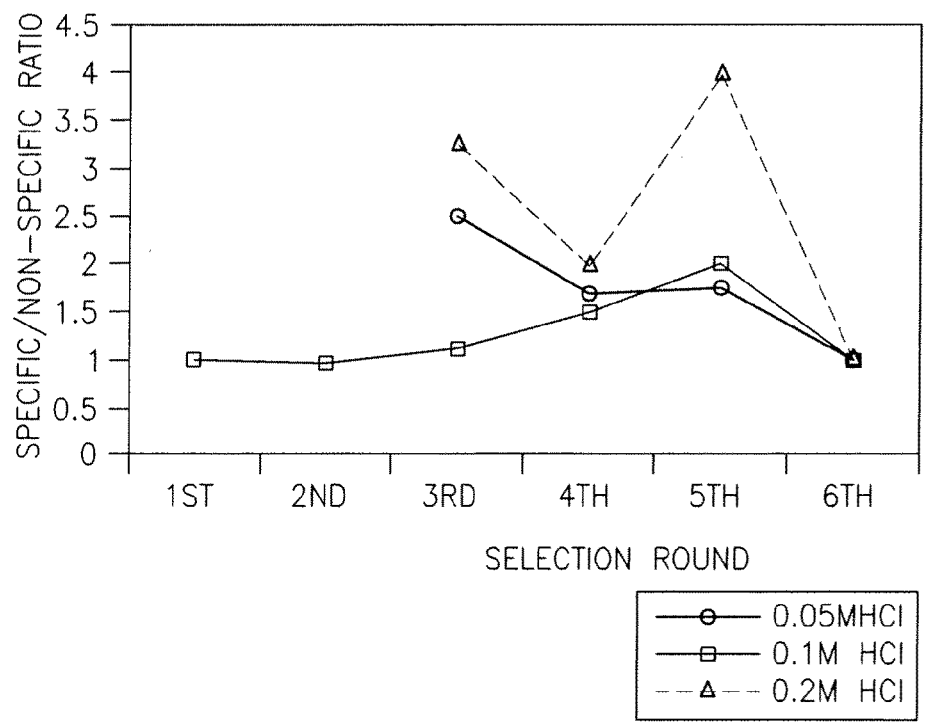

FIG. 7 shows the specific enrichment of a phage population expressing a library of mutated IFNα2. y axis: ratio between number of eluted phages from IFNAR1-coated wells and wells lacking IFNAR1, using serial dilutions. x axis: panning round. Starting from third round, phages were eluted from wells in 3 steps, using 0.05, 0.1, and 0.2 M HCl.

Figure 8:
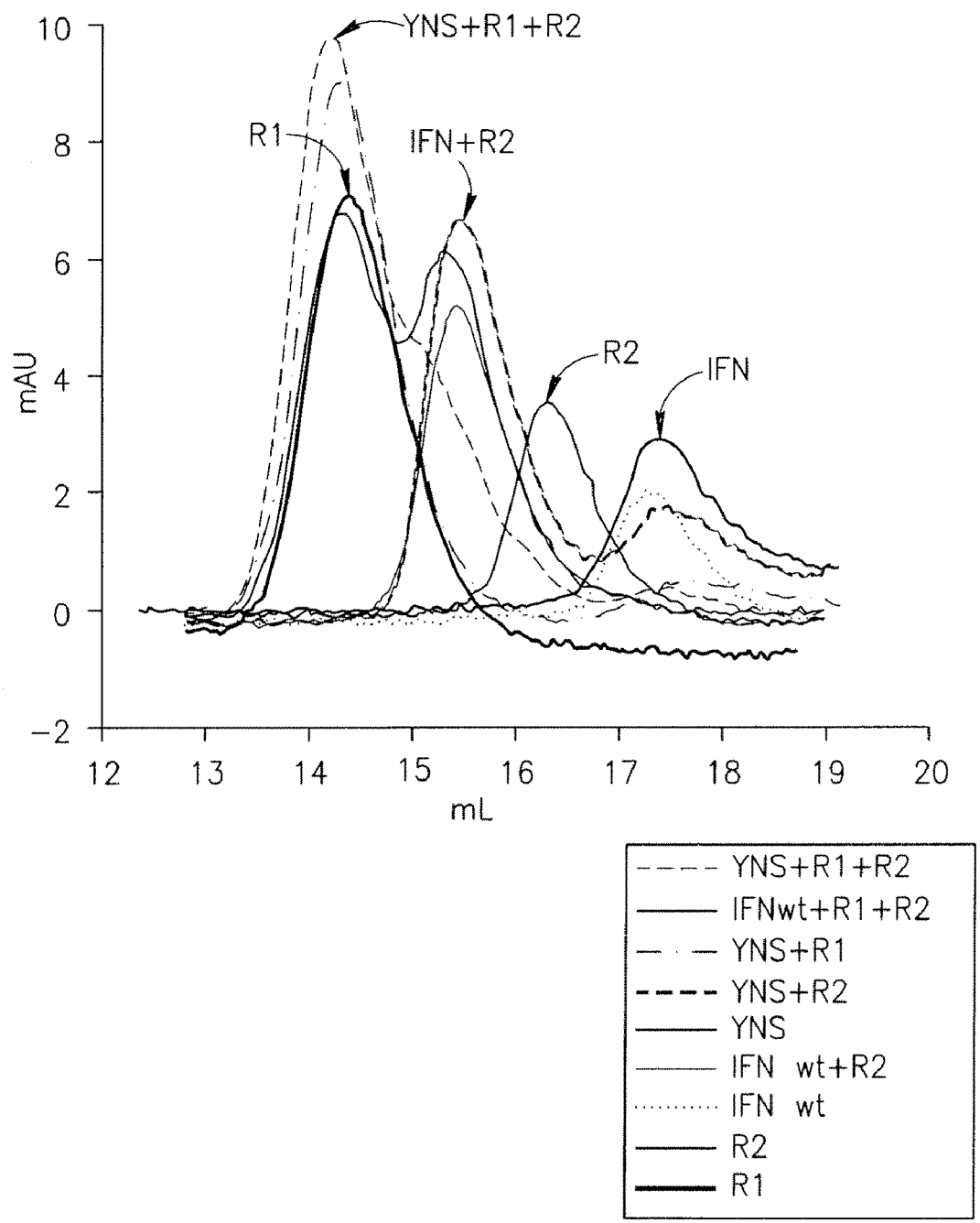

FIG. 8 shows the retention patterns of wild-type IFNα2 and YNS when injected along with IFNAR1 (R1) and/or IFNAR2 (R2) into a Sepharose 200GL analytical gel filtration column. y axis: detection of protein flow at 280 nm; x axis: retention volume. A ternary complex peak is visible with YNS (14.2 ml), but not with wild-type IFNα2 where two peaks, one of R2+IFN and the second of R1, are visible.

Figure 9:
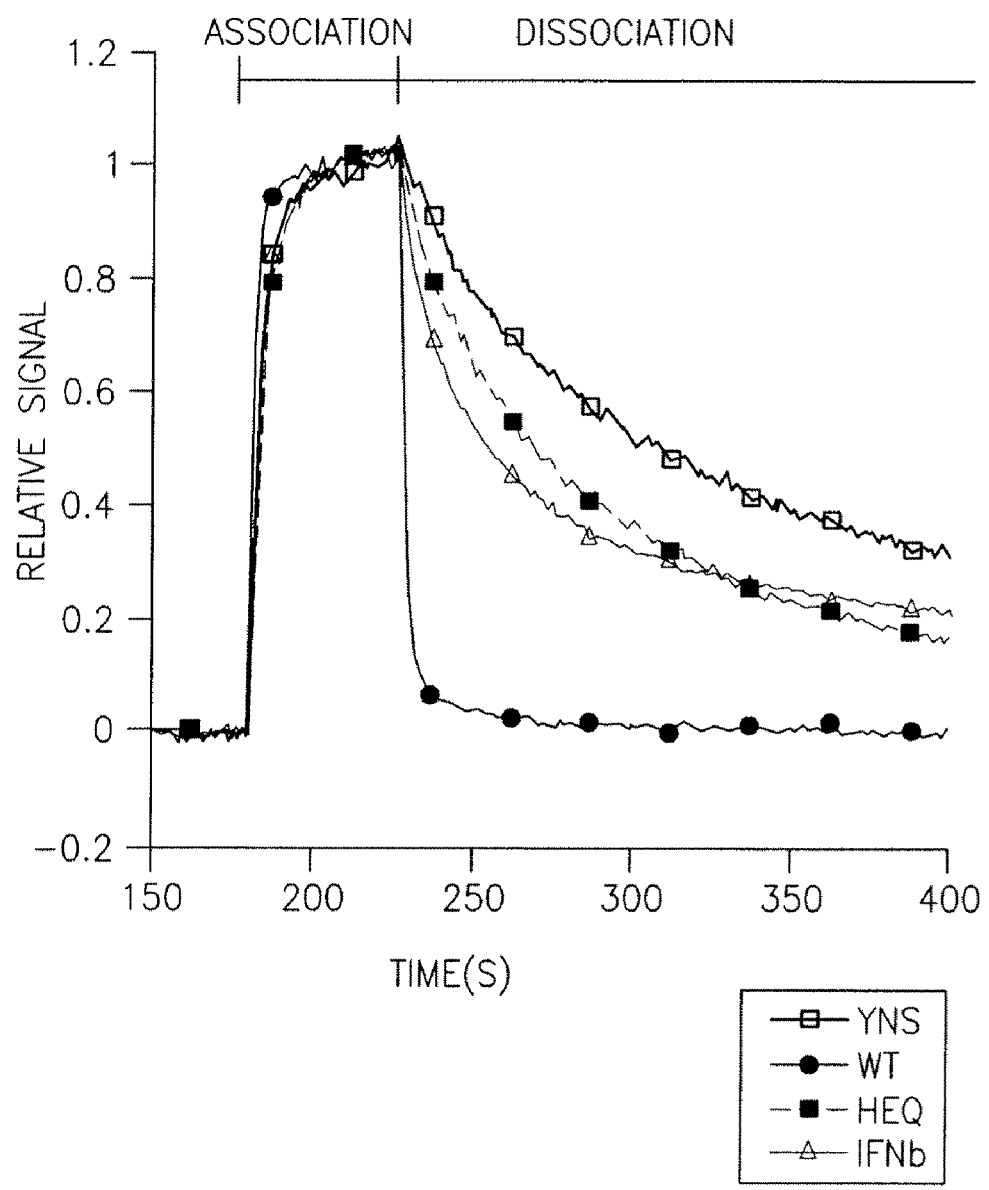

FIG. 9 shows the IFNAR1-binding signals of YNS, wt IFNα2, HEQ, and IFNβ as recorded by the ProteOn with IFNAR1 immobilized to the surface. Signals were normalized to the same relative signal (1) to show differences in dissociation rate between interferons.

Figure 10A:
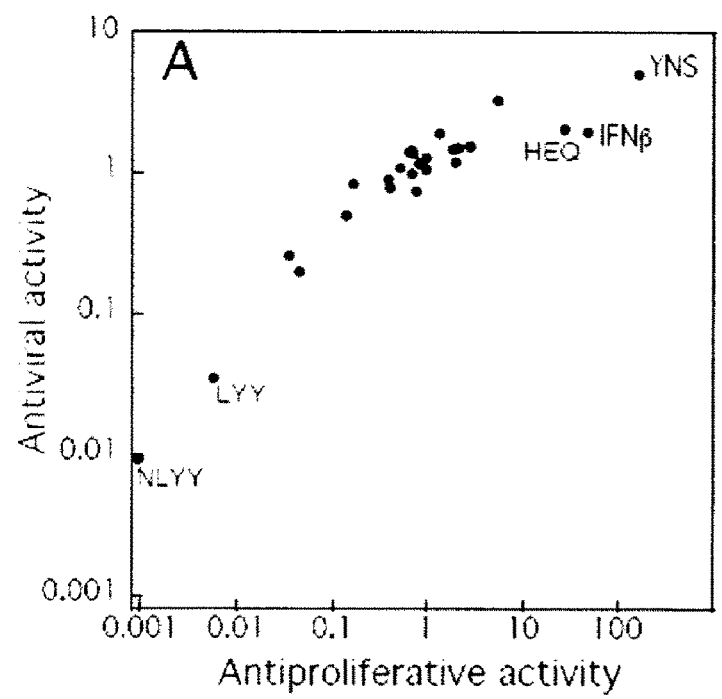
Figure 10B:
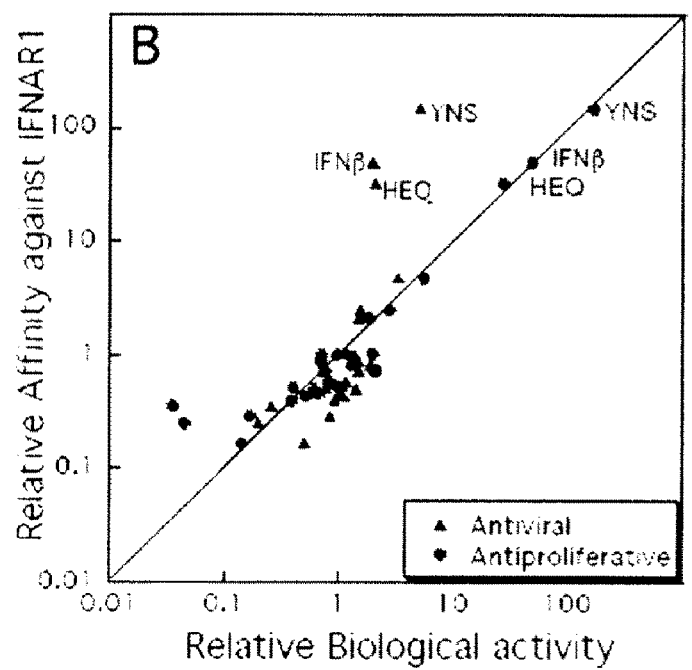

FIGS. 10A and 10B show the biological activities of interferon mutants. FIG. 10A shows the antiviral activity and anti-proliferative activity (relative to wt) of 21 IFNα2 single mutants, triple mutant H57A, E58A, Q61A, quadruple mutant N65A, L80A, Y85A, Y89A, the triple mutant H57Y, E58N, Q61S, and of IFNβ. FIG. 10B shows the relative antiviral and anti-proliferative activities of the same proteins vs. relative binding affinity for IFNAR1-EC. Data are from Tables 1-4. Line represents a theoretical relationship between biological activity and affinity. For points above the line, change in biological activity (antiviral or anti-proliferative) is weaker than change in affinity; for points below the line, the opposite is the case.

Figure 11:
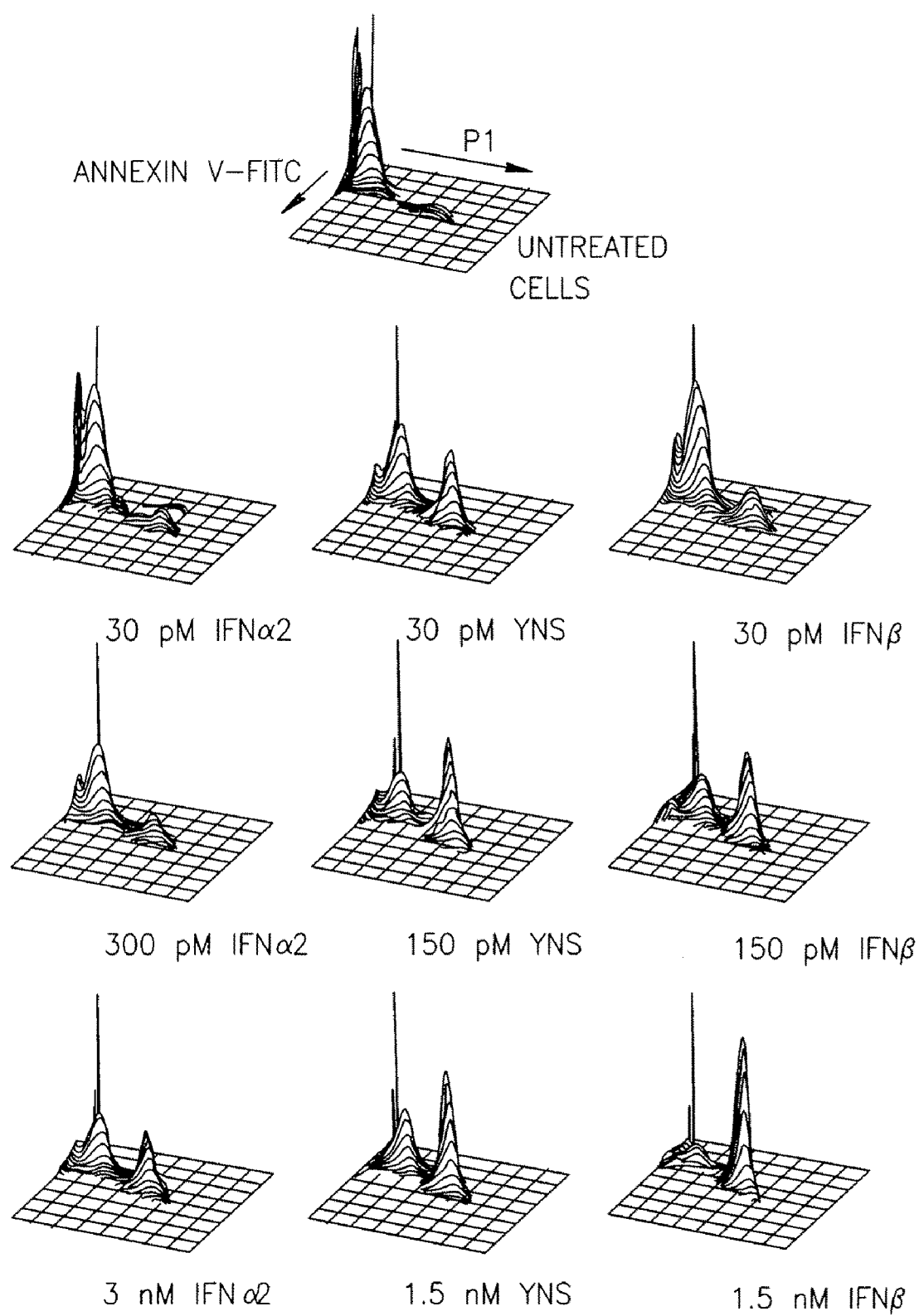

FIG. 11 shows the apoptotic activity of YNS, wt IFNα2, and IFNβ. y axis: Levels of phosphatidylserine in the outer plasma membrane leaflet, an apoptotic marker detected by annexin V; x axis levels of cell permeability (propidium iodide). Cells were incubated in IFN for 72 h. A representative experiment from 3 repetitions is depicted.

Figure 12A:
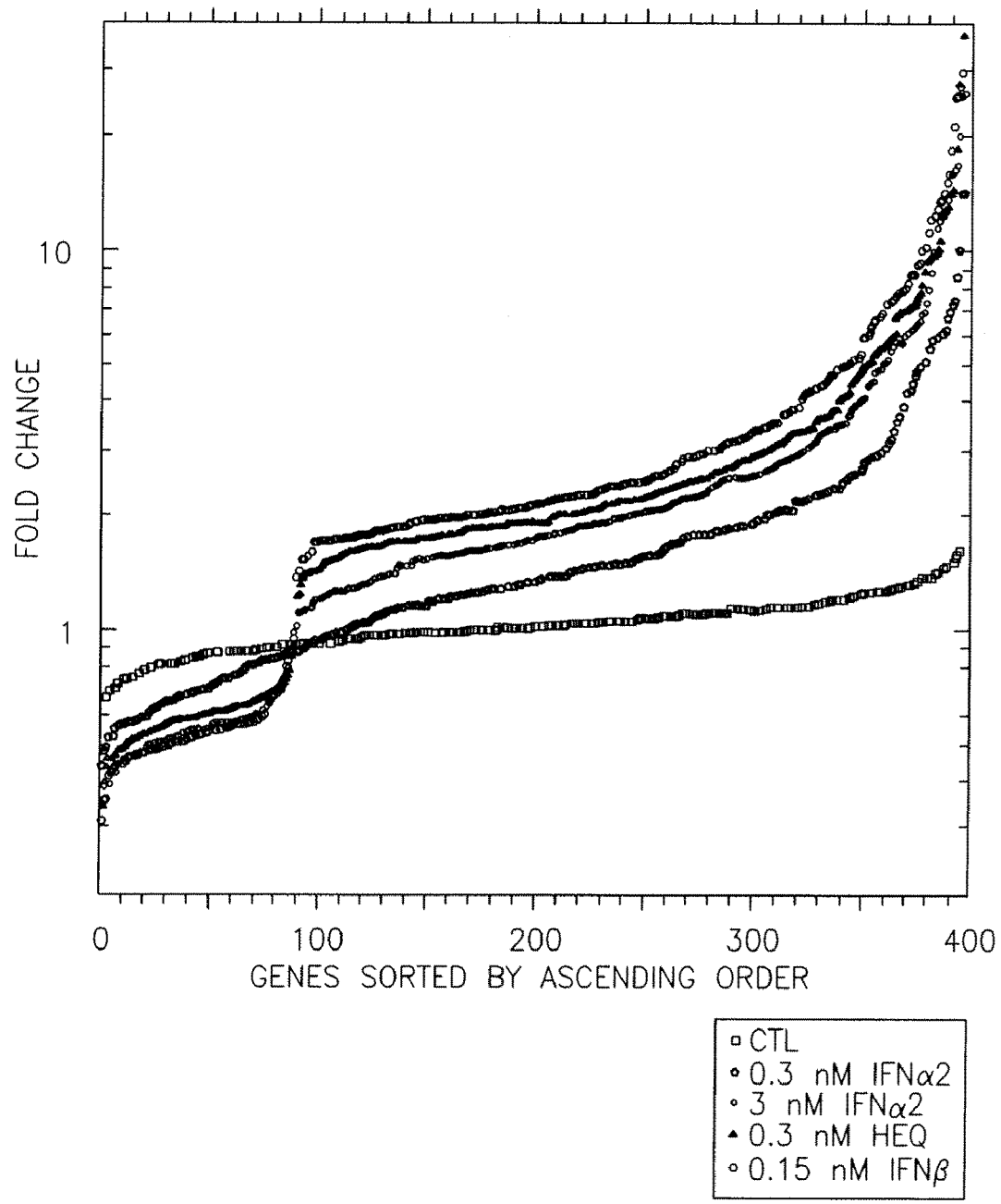
Figure 12B:
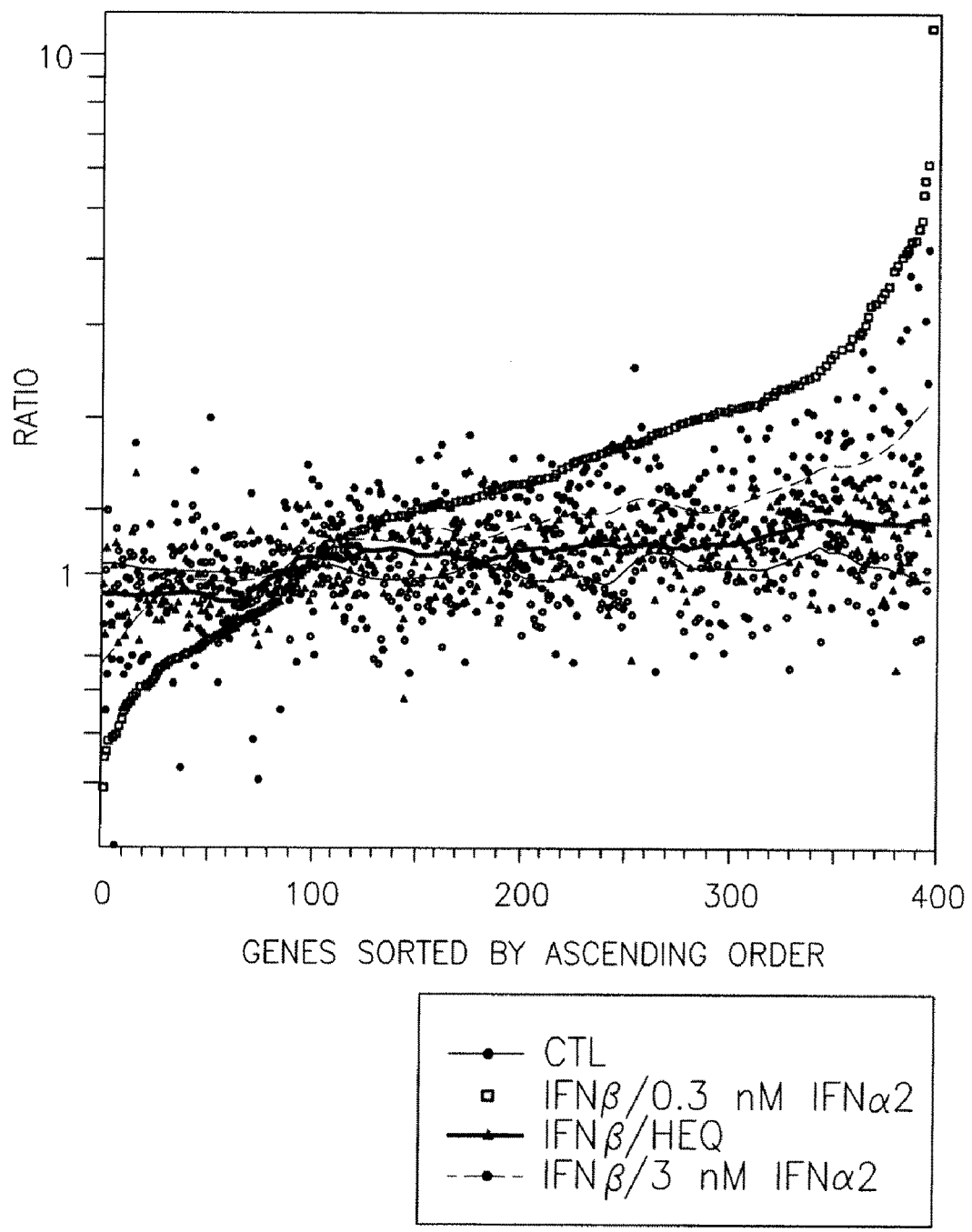
Figure 12C:
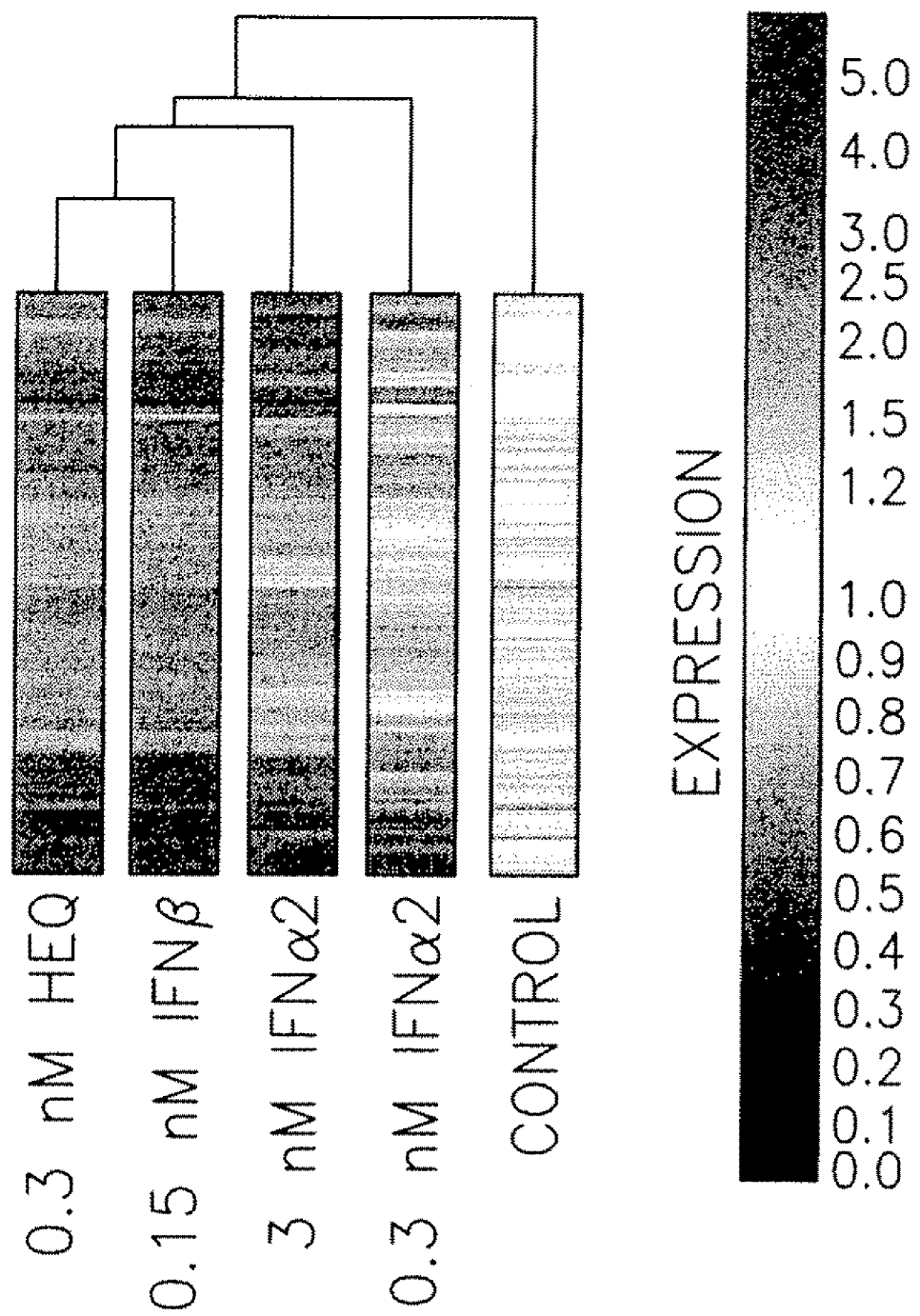

FIGS. 12A, 12B and 12C show the effects of IFN on gene expression by spotted oligonucleotide microarray. FIG. 12A shows the changes in expression levels of IFN-stimulated 395-gene subset, plotted in ascending order separately for each condition. FIG. 12B shows the expression levels relative to gene expression upon adding 0.15 nM IFN-β. Genes from the 4 groups were sorted in ascending order of IFN-β/IFN-α2 (0.3 nM) ratios. Trend lines were created with a 15% data smoothing function in Kaleidagraph™ (Synergy Software). FIG. 12C shows a cluster analysis, with distance correlation between genes and Spearman correlation between conditions.

Figure 13:
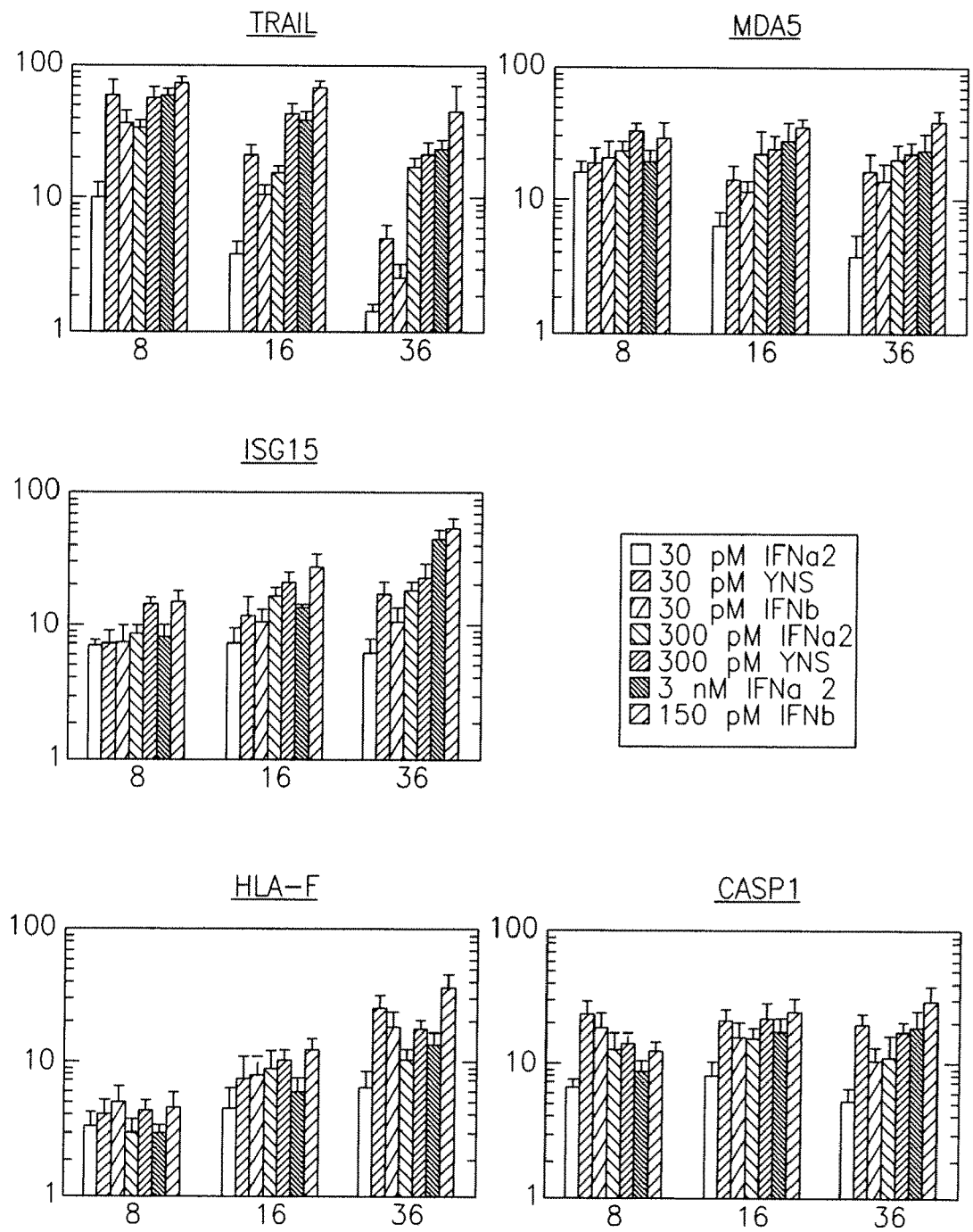

FIG. 13 shows the expression levels of selected genes upon treatment with wt IFNα2, IFNβ, or YNS at indicated time points and concentrations by real-time PCR.

Figure 14A:
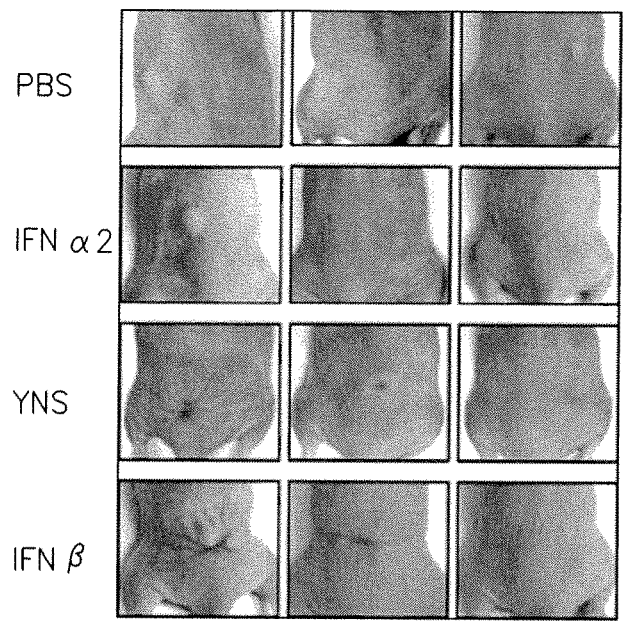
Figure 14B:
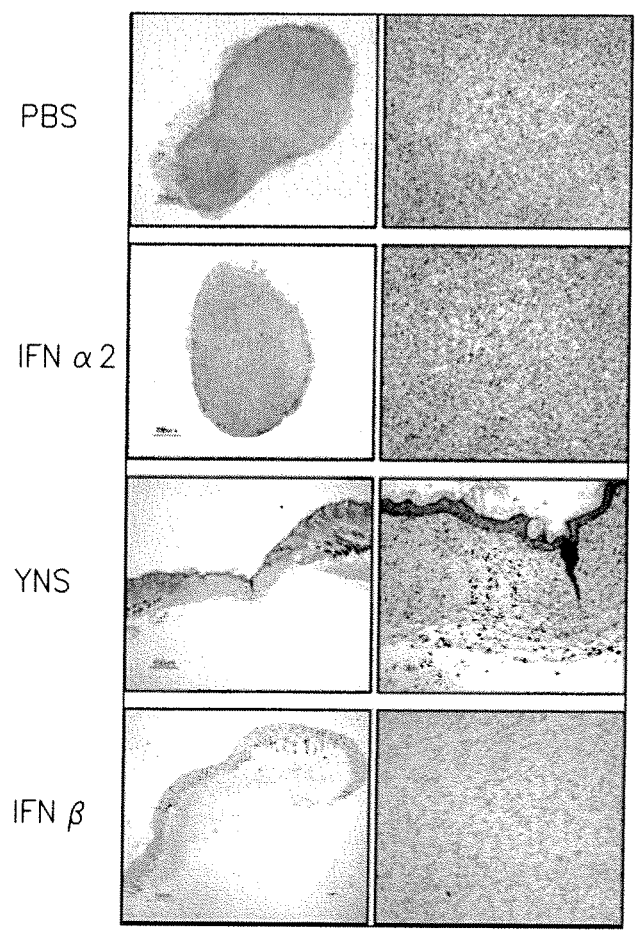

FIGS. 14A and 14B show the interferon activity in MDA231 breast cancer tumors in nude mice. FIG. 14A shows the representative images of healing of wt IFN-αα2-, YNS-, and IFNβ-treated tumors. FIG. 14B shows the histological analysis (H&E staining) of MDA231 tumors (PBS, wt IFNα2) or scars (YNS, IFNβ) from mice. Left lane, low magnification; right lane, high magnification.

Figure 15:
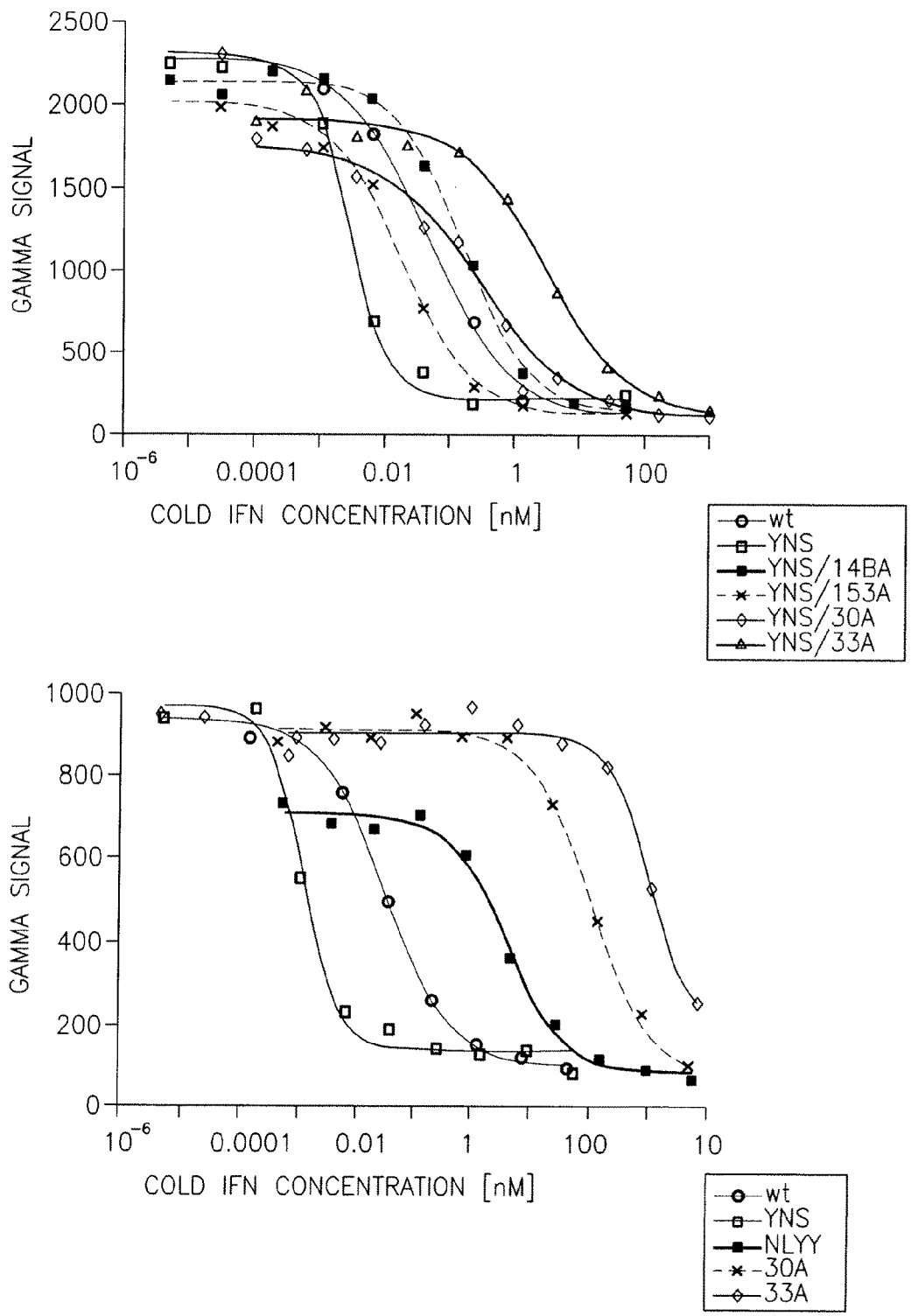

FIG. 15 shows in situ binding curves of IFN mutants. Binding by $^{125}$I-labeled wild type IFNα2 was competing with different concentrations of various interferons at. X-axis: tested IFN concentration; Y-axis: gamma signal of bound $^{125}$I-labeled wild type IFNα2. Top panel: wt & YNS vs. double mutants. Bottom panel: wt & YNS vs. single mutants.

Figure 16A:
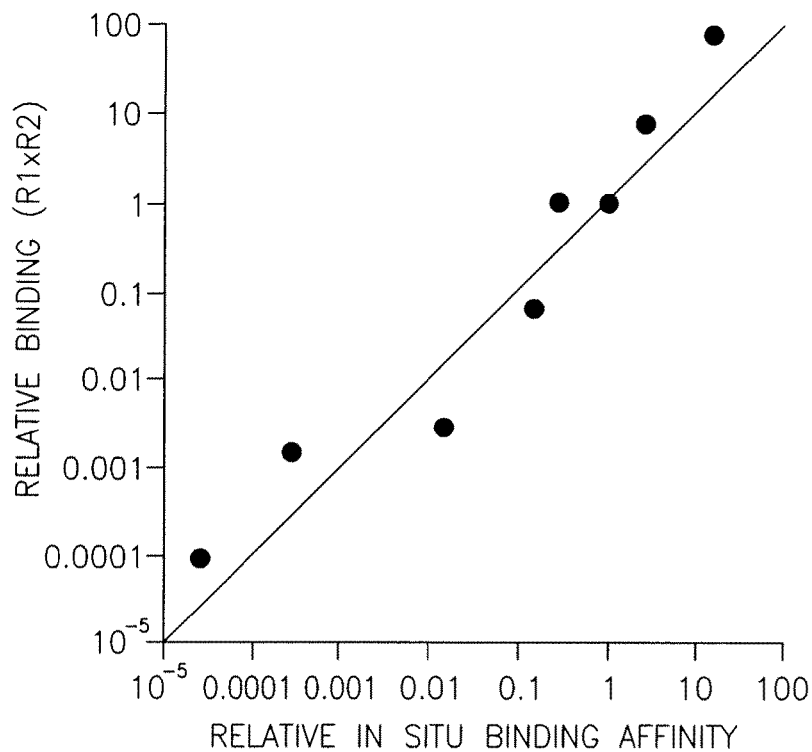
Figure 16B:
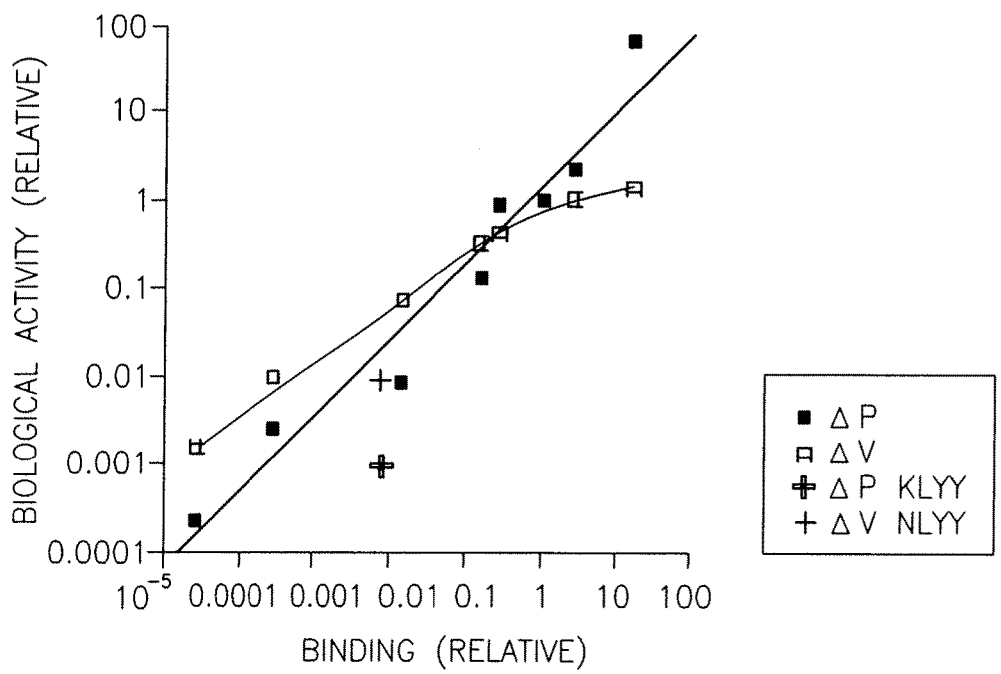

FIGS. 16A and 16B show the relationship between IFN binding and activity. FIG. 16A show theoretical vs. measured affinities of different mutants towards the receptor. X axis: Binding affinities in situ in WISH cells; Y axis: calculated affinities based on the contribution of each receptor subunit alone (R1×R2) by SPR. FIG. 16B shows the biological potency vs. in situ affinity of IFNα2 mutants. X-axis: affinity relative to wt IFNα2. Y-axis: antiproliferative ("ΔP" in legend) (■); and antiviral ("ΔV" in legend) (□) potency of combined IFNα2 mutants relative to wild type. Cross symbols: NLYY, an IFN mutation with almost no IFNAR1 binding but normal IFNAR2 binding.

Figure 17A:
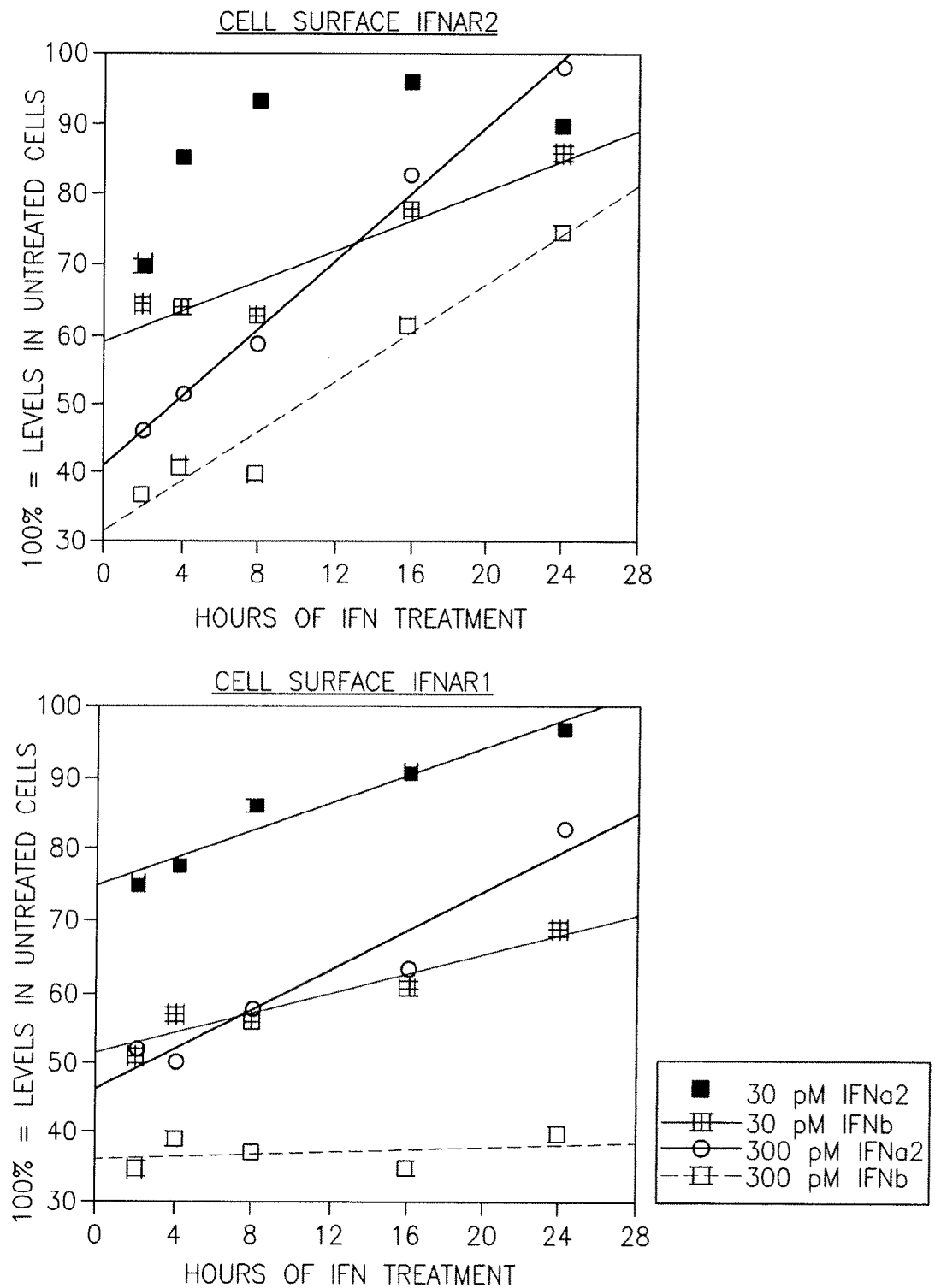
Figure 17B:
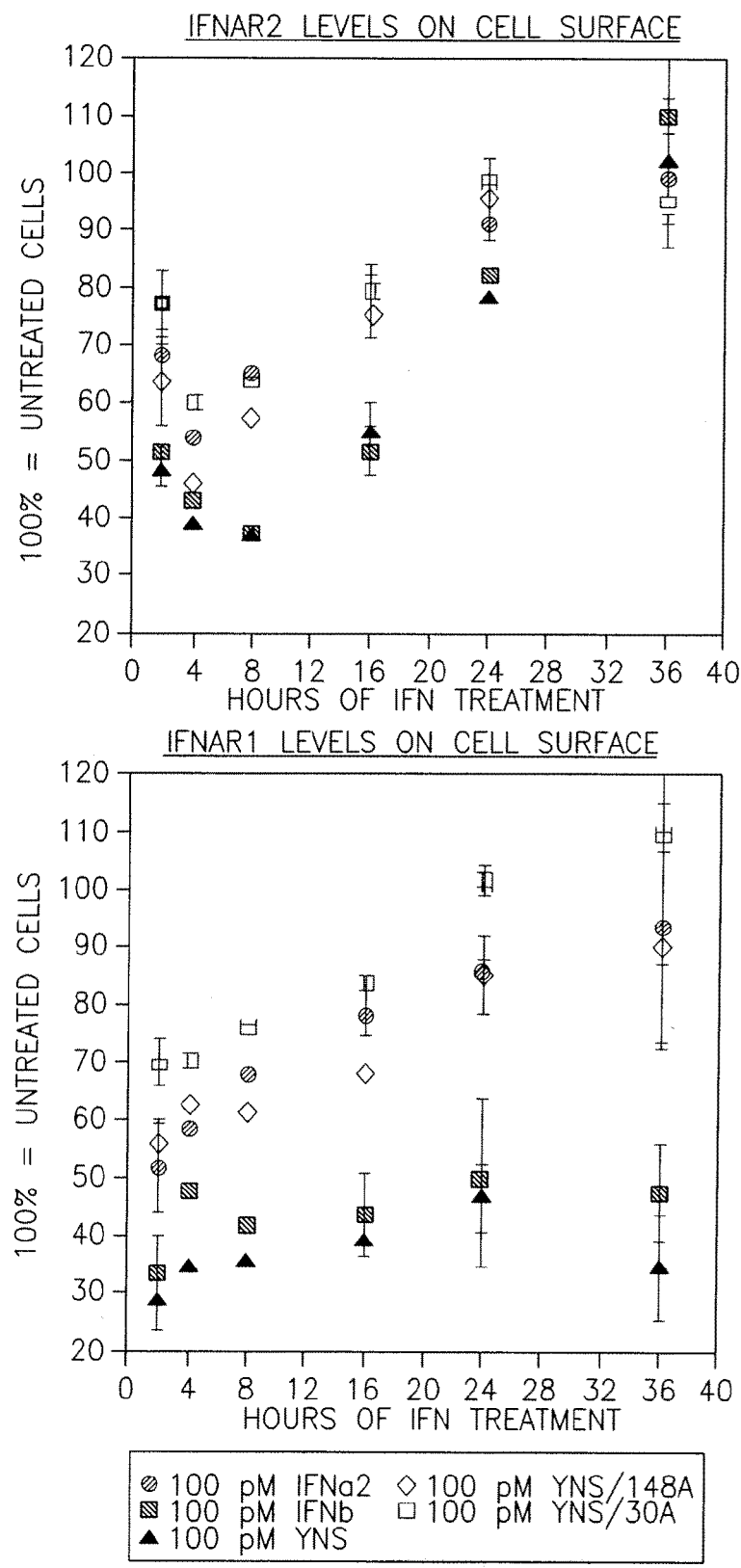

FIGS. 17A and 17B show shows the receptor downregulation following IFN treatment. FIG. 17A shows the levels of surface IFNAR2 (top panel) and IFNAR1 (bottom panel) after incubation with IFNα2 or IFNβ at 30 or 300 pM. FIG. 17B shows the same experiment done with 100 pM of wt and mutant IFNs. Top panel-IFNAR2; bottom panel-IFNAR1.

DETAILED DESCRIPTION OF THE PREFERRED EMBODIMENTS

The present invention provides IFNα2 mutants and active fragments, analogs, derivatives, and variants thereof, nucleotide molecules encoding same, pharmaceutical compositions comprising same, and methods utilizing same for treating cancer, infectious diseases, and autoimmune diseases.

In one embodiment, the present invention provides a mutated interferon α2 (IFNα2) polypeptide, comprising a mutation selected from the group consisting of (a) mutation of the histidine at position 57 (H57) to a residue selected from the group consisting of tyrosine and methionine; (b) mutation of the glutamate at position 58 (E58) to a residue selected from the group consisting of asparagine, aspartate, leucine, and alanine; and (c) mutation of the glutamine at position 61 (Q61) to a residue selected from the group consisting of serine, leucine, and aspartate; and combinations thereof. Preferably, the mutated IFNα2 polypeptide is a recombinant polypeptide. More preferably, the mutation increases affinity of the mutated IFNα2 polypeptide for the IFNAR1 subunit of the interferon receptor 1 ("IFNAR") (e.g. a human IFNAR), relative to wt IFNα2. In another embodiment, the mutated IFNα2 polypeptide exhibits improved IFNAR agonist activity, relative to wild-type IFNα2. Each possibility represents a separate embodiment of the present invention.

In another embodiment, a mutated IFNα2 polypeptide of the present invention comprises 1 of mutations (a), (b), and (c) (i.e. the mutations of H57, E58, and Q61, as described hereinabove). In another embodiment, the mutated IFNα2 polypeptide comprises at least 2 of mutations (a), (b), and (c). In another embodiment, the mutated IFNα2 polypeptide comprises 2 of mutations (a), (b), and (c). In another embodiment, the mutated IFNα2 polypeptide comprises all 3 of mutations (a), (b), and (c). Each possibility represents a separate embodiment of the present invention.

H57 is, in another embodiment of methods and compositions of the present invention, mutated to tyrosine. In another embodiment, H57 is mutated to methionine. In another embodiment, H57 is mutated to another residue that increases affinity for IFNAR1. In another embodiment, H57 is mutated to another residue that confers improved IFNAR agonist activity upon the mutated IFNα2 polypeptide. Each possibility represents a separate embodiment of the present invention.

E58 is, in another embodiment of methods and compositions of the present invention, mutated to asparagine. In another embodiment, E58 is mutated to aspartate. In another embodiment, E58 is mutated to leucine. In another embodiment, E58 is mutated to alanine. In another embodiment, E58 is mutated to another residue that increases affinity for IFNAR1. In another embodiment, E58 is mutated to another residue that confers improved IFNAR agonist activity upon the mutated IFNα2 polypeptide. Each possibility represents a separate embodiment of the present invention.

Q61 is, in another embodiment of methods and compositions of the present invention, mutated to serine. In another embodiment, Q61 is mutated to leucine. In another embodiment, Q61 is mutated to aspartate. In another embodiment, Q61 is mutated to another residue that increases affinity for IFNAR1. In another embodiment, Q61 is mutated to another residue that confers improved IFNAR agonist activity upon the mutated IFNα2 polypeptide. Each possibility represents a separate embodiment of the present invention.

In another embodiment, a mutated IFNα2 polypeptide of the present invention comprises at least 2 of the mutations H57Y, E58N, and Q61S. In another embodiment, the mutated IFNα2 polypeptide comprises both of the mutations H57Y and Q61S. In another embodiment, the mutated IFNα2 polypeptide comprises 2 mutations selected from H57Y, E58N, and Q61S. In another embodiment, the mutated IFNα2 polypeptide comprises all 3 of the mutations H57Y, E58N, and Q61S. Preferably, the mutated IFNα2 polypeptide exhibits improved IFNAR agonist activity, relative to wild-type IFNα2. An example of a mutated IFNα2 polypeptide sequence that contains all 3 of these mutations is set forth in SEQ ID NO: 11 and is encoded for by SEQ ID NO: 21. Each possibility represents a separate embodiment of the present invention.

In another embodiment, a mutated IFNα2 polypeptide of the present invention comprises at least 2 of the mutations H57M, E58D, and Q61L. In another embodiment, the mutated IFNα2 polypeptide comprises both of the mutations H57Y and Q61L. In another embodiment, the mutated IFNα2 polypeptide comprises 2 mutations selected from H57M, E58D, and Q61L. In another embodiment, the mutated IFNα2 polypeptide comprises all 3 of the mutations H57M, E58D, and Q61 L. Preferably, the mutated IFNα2 polypeptide exhibits improved IFNAR agonist activity, relative to wild-type IFNα2. An example of a mutated IFNα2 polypeptide sequence that contains all 3 of these mutations is set forth in SEQ ID NO: 10 and is encoded for by SEQ ID NO: 20. Each possibility represents a separate embodiment of the present invention.

In another embodiment, a mutated IFNα2 polypeptide of the present invention comprises at least 2 of the mutations H57Y, E58L, and Q61D. In another embodiment, the mutated IFNα2 polypeptide comprises both of the mutations H57Y and Q61D. In another embodiment, the mutated IFNα2 polypeptide comprises 2 mutations selected from H57Y, E58L, and Q61D. In another embodiment, the mutated IFNα2 polypeptide comprises all 3 of the mutations H57Y, E58L, and Q61D. Preferably, the mutated IFNα2 polypeptide exhibits improved IFNAR agonist activity, relative to wild-type IFNα2. An example of a mutated IFNα2 polypeptide sequence that contains all 3 of these mutations is set forth in SEQ ID NO: 40. Each possibility represents a separate embodiment of the present invention.

In another embodiment, a mutated IFNα2 polypeptide of the present invention comprises at least 2 of the mutations H57Y, E58A, and Q61S. In another embodiment, the mutated IFNα2 polypeptide comprises 2 mutations selected from H57Y, E58A, and Q61 S. In another embodiment, the mutated IFNα2 polypeptide comprises all 3 of the mutations H57Y, E58A, and Q61S. Preferably, the mutated IFNα2 polypeptide exhibits improved IFNAR agonist activity, relative to wild-type IFNα2. An example of a mutated IFNα2 polypeptide sequence that contains all 3 of these mutations is set forth in SEQ ID NO: 41. Each possibility represents a separate embodiment of the present invention.

Figure 3A:
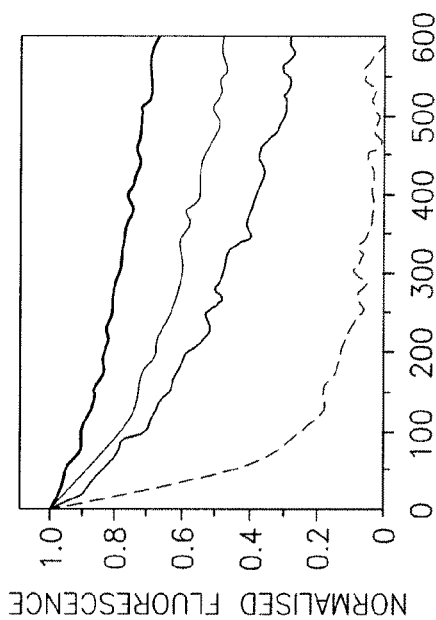
FIGS. 3A through 3D show IFN binding to IFNAR1-EC and ternary complex formation.
Figure 3B:
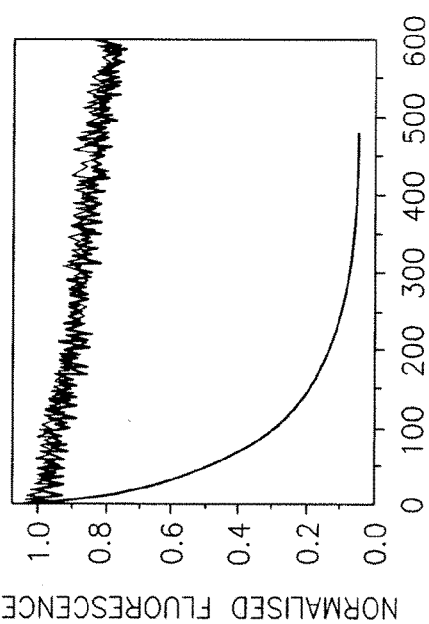
Figure 3C:
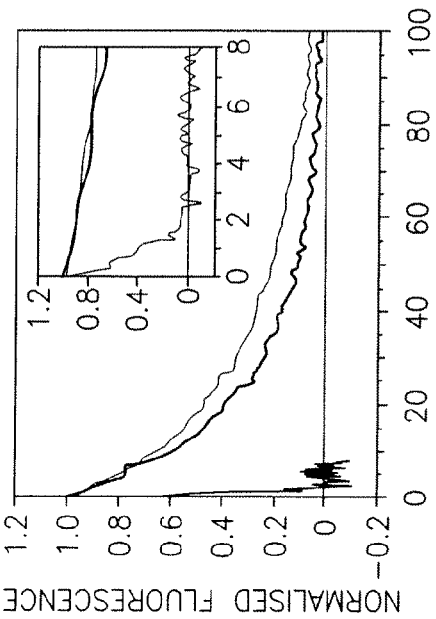
Figure 3D:
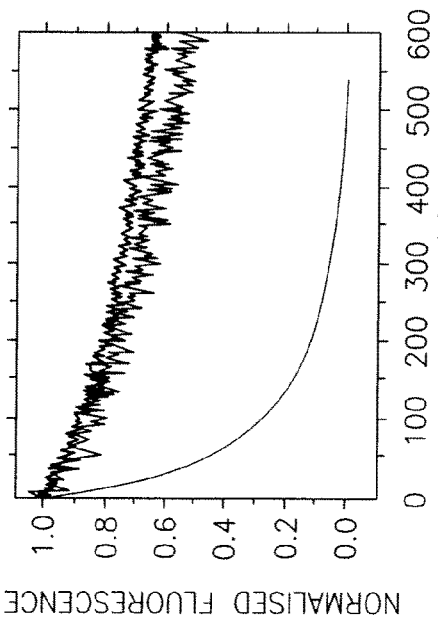

As provided herein, certain of the mutated IFNα2 polypeptides of the present invention containing gain-of-function mutations in residues 57, 58, and/or 61 exhibit an increased affinity for IFNAR1. This increased affinity results in enhanced biological activity, e.g. anti-proliferative activity, reminiscent of, and in some cases even exceeding, IFNβ. These mutated IFNα2 polypeptides thus exhibit enhanced IFNAR-mediated signaling and enhanced biological activity (e.g. anti-proliferative effect) relative to wt IFNα2 and IFNβ. For example, the effect of increased affinity of HEQ for IFNAR1 on ternary complex binding was determined by measuring dissociation of IFN-α2, HEQ, and IFN-β at different concentrations of IFNAR1-EC and IFNAR2-EC at stoichiometric ratios. While IFN-α2 dissociation kinetics were sharply faster at lower IFNAR1 surface concentration (FIG. 3B), IFN-β and HEQ exhibited slow, largely concentration-independent, dissociation curves (FIGS. 3C-D, respectively). Similar findings were seen for MDL and YNS, except in this case, the mutant bound even more tightly than IFN-β (as shown e.g. in FIG. 7B and Table 6). Thus, YNS, HEQ, and IFN-β recruited IFNAR1-EC to the ternary complex more efficiently than wt IFN-α2.

In another embodiment, the present invention provides a mutated IFNα2 polypeptide comprising a mutation selected from the group consisting of (a) mutation of H57; (b) mutation of E58; and (c) mutation of Q61; (d) mutation of the asparagine at position 65 (N65); (e) mutation of the leucine at position 80 (L80); (f) mutation of the tyrosine at position 85 (Y85); and (g) mutation of the tyrosine at position 89 (Y89); and combinations thereof, wherein the mutation decreases affinity of the mutated IFNα2 polypeptide for the IFNAR1 subunit of IFNAR (e.g. a human IFNAR). Preferably, the mutated IFNα2 polypeptide is a recombinant polypeptide. More preferably, the mutated IFNα2 polypeptide exhibits IFNAR antagonist activity. In another embodiment, H57 is mutated to a residue other than tyrosine or methionine. In another embodiment, E58 is mutated to a residue other than asparagine, aspartate, or leucine. In another embodiment, Q61 is mutated to a residue other than serine, leucine, or aspartate. Each possibility represents a separate embodiment of the present invention.

In another embodiment, a mutated IFNα2 polypeptide of the present invention comprises 1 of mutations (a)-(g) (i.e. the mutations of H57, E58, Q61, N65, L80, Y85, and Y89, as described hereinabove). In another embodiment, the mutated IFNα2 polypeptide comprises at least 2 of mutations (a)-(g). In another embodiment, the mutated IFNα2 polypeptide comprises 2 of mutations (a)-(g). In another embodiment, the mutated IFNα2 polypeptide comprises at least 3 of mutations (a)-(g). In another embodiment, the mutated IFNα2 polypeptide comprises 3 of mutations (a)-(g). In another embodiment, the mutated IFNα2 polypeptide comprises more than 3 of mutations (a)-(g). Each possibility represents a separate embodiment of the present invention.

H57 is, in another embodiment of methods and compositions of the present invention, mutated alanine. In another embodiment, H57 is mutated to another residue that decreases affinity for IFNAR1. Each possibility represents a separate embodiment of the present invention.

E58 is, in another embodiment of methods and compositions of the present invention, mutated alanine. In another embodiment, E58 is mutated to another residue that decreases affinity for IFNAR1. Each possibility represents a separate embodiment of the present invention.

Q61 is, in another embodiment of methods and compositions of the present invention, mutated alanine. In another embodiment, Q61 is mutated to another residue that decreases affinity for IFNAR1. Each possibility represents a separate embodiment of the present invention.

N65 is, in another embodiment of methods and compositions of the present invention, mutated alanine. In another embodiment, N65 is mutated to another residue that decreases affinity for IFNAR1. Each possibility represents a separate embodiment of the present invention.

L80 is, in another embodiment of methods and compositions of the present invention, mutated alanine. In another embodiment, L80 is mutated to another residue that decreases affinity for IFNAR1. Each possibility represents a separate embodiment of the present invention.

Y85 is, in another embodiment of methods and compositions of the present invention, mutated alanine. In another embodiment, Y85 is mutated to another residue that decreases affinity for IFNAR1. Each possibility represents a separate embodiment of the present invention.

Y89 is, in another embodiment of methods and compositions of the present invention, mutated alanine. In another embodiment, Y89 is mutated to another residue that decreases affinity for IFNAR1. Each possibility represents a separate embodiment of the present invention.

As provided herein, certain mutated IFNα2 proteins of the present invention exhibit reduced affinity for IFNAR1. Since the mutated IFNα2 proteins retain wild-type affinity for IFNAR2, these mutants will occupy IFNAR2 without forming the ternary complex, thus antagonizing IFNAR signaling. For example, NLYY is an IFNα2 variant that does not detectably bind IFNAR1 a detectable level, but binds IFNAR2 with an affinity similar to wt IFNα2 (Example 2).

In another embodiment, a mutated IFNα2 polypeptide of the present invention comprises at least 2 of the mutations N65A, L80A, Y85A, and Y89A. In another embodiment, the mutated IFNα2 polypeptide comprises 2 mutations selected from N65A, L80A, Y85A, and Y89A. In another embodiment, the mutated IFNα2 polypeptide comprises at least 3 of the mutations N65A, L80A, Y85A, and Y89A. In another embodiment, the mutated IFNα2 polypeptide comprises 3 mutations selected from N65A, L80A, Y85A, and Y89A. In another embodiment, the mutated IFNα2 polypeptide comprises all 3 of the mutations L80A, Y85A, and Y89A. An example of a mutated IFNα2 polypeptide sequence that contains all 3 of these mutations is set forth in SEQ ID NO: 45. In another embodiment, the mutated IFNα2 polypeptide comprises all four of the mutations N65A, L80A, Y85A, and Y89A. Preferably, the mutated IFNα2 polypeptide exhibits IFNAR antagonist activity. An example of a mutated IFNα2 polypeptide sequence that contains all 3 of these mutations is set forth in SEQ ID NO: 6 and is encoded for by SEQ ID NO: 16. Each possibility represents a separate embodiment of the present invention.

In another embodiment, a mutated IFNα2 polypeptide of the present invention comprises at least 2 of the mutations H57A, E58A, and Q61A. In another embodiment, the mutated IFNα2 polypeptide comprises all 3 of the mutations H57A, E58A, and Q61A. Preferably, the mutated IFNα2 polypeptide exhibits IFNAR antagonist activity. An example of a mutated IFNα2 polypeptide sequence that contains all 3 of these mutations is set forth in SEQ ID NO: 5 and is encoded for by SEQ ID NO: 15. Each possibility represents a separate embodiment of the present invention.

In another embodiment, a mutated IFNα2 polypeptide of the present invention further comprises an additional mutation, aside from the aforementioned mutations at residues H57, E58, Q61, N65, L80, Y85, and/or Y89. In another embodiment, the additional mutation is in the C-terminal tail. In another embodiment, the additional mutation is a mutation of a residue selected from the group consisting of (a) the glutamate at position 159 (E159), (b) the serine at position 160 (S160), (c) the leucine at position 161 (L161), (d) the serine at position 163 (S163), and (e) the glutamate at position 165 (E165) to a residue selected from lysine and arginine. In another embodiment, a negative or neutral residue among the 7 carboxy-terminal residues of the IFNα2 protein is mutated to a residue selected from lysine and arginine. In another embodiment, the additional mutation increases affinity of the mutated IFNα2 polypeptide for the IFNAR2 subunit of the IFNAR (e.g. a human INFAR). Each possibility represents a separate embodiment of the present invention.

Preferably, 2 or more of the residues selected from E159, S160, L161, S163, and E165 are mutated to a residue selected from lysine and arginine. In another embodiment, 3 or more of these residues are mutated to a residue selected from lysine and arginine. In another embodiment, more than 3 of these residues are mutated to a residue selected from lysine and arginine. Preferably, the mutated IFNα2 polypeptide exhibits improved IFNAR agonist activity, relative to wild-type IFNα2. Each possibility represents a separate embodiment of the present invention.

In another embodiment, the additional mutation in the C-terminal tail is selected from the group consisting of (a) mutation of the glutamate at position 159 to lysine; (b) mutation of the serine at position 160 to arginine; and (c) mutation of the arginine at position 162 to lysine; and combinations thereof. In another embodiment, the mutated IFNα2 polypeptide comprises 1 of mutations (a-c). In another embodiment, the mutated IFNα2 polypeptide comprises 2 or more of mutations (a-c). In another embodiment, the mutated IFNα2 polypeptide comprises all 3 of mutations (a-c). Preferably, the mutated IFNα2 polypeptide exhibits improved IFNAR agonist activity, relative to wild-type IFNα2. Each possibility represents a separate embodiment of the present invention.

As provided herein (Examples 4-5), IFNα2 mutants with increased net positive charge in the tail region exhibit enhanced affinity for IFNAR2. For example, α8-tail IFNα2 binds IFNAR2 18-fold tighter than wt IFNα2. As a result it possesses enhanced biological activity (e.g. antiviral and anti-proliferative activity) compared to wt IFNα2. The antiviral and anti-proliferative activities of α8-tail are 3-fold and the 10-fold higher than wild-type, respectively (Table 4).

In another embodiment, the present invention provides a mutated IFNα2 polypeptide comprising both (a) a gain-of-function mutation for IFNAR1 binding in residues H57, E58, and/or Q61; and (b) a gain-of-function tail mutation for IFNAR2 binding. As provided herein, affinity of IFN proteins for IFNAR is determined by additive contributions of IFNAR1 binding and IFNAR2 binding. Thus, the present invention shows that combination of these two mutations (a) and (b) further enhances IFNAR binding, IFNAR signaling, and biological activity, relative to mutated IFNα2 polypeptides having either (a) or (b) alone.

In another embodiment, the present invention provides a mutated IFNα2 polypeptide comprising both (a) the mutation H57Y; and (b) a gain-of-function tail mutation for IFNAR2 binding (e.g. the α8-tail mutation).

In another embodiment, the present invention provides a mutated IFNα2 polypeptide comprising both (a) at least 2 of the mutations H57Y, E58N, and Q61S; and (b) a gain-offunction tail mutation for IFNAR2 binding (e.g. the α8-tail mutation). In another embodiment, the IFNα2 polypeptide comprises both (a) both of the mutations H57Y and Q61 S; and (b) a gain-of-function tail mutation for IFNAR2 binding. In another embodiment, the IFNα2 polypeptide comprises both (a) all 3 of the mutations H57Y, E58N, and Q61S; and (b) a gain-of-function tail mutation for IFNAR2 binding. A non-limiting example of a mutated IFNα2 polypeptide comprising both of mutations (a) and (b) (YNS+α8-tail) is set forth in SEQ ID NO: 13 and is encoded by the nucleotide molecule set forth in SEQ ID NO: 23. Each possibility represents a separate embodiment of the present invention.

In another embodiment, the present invention provides a mutated IFNα2 polypeptide comprising both (a) at least 2 of the mutations H57M, E58D, and Q61L; and (b) a gain-of-function tail mutation for IFNAR2 binding (e.g. the α8-tail mutation). In another embodiment, the IFNα2 polypeptide comprises both (a) all 3 of the mutations H57M, E58D, and Q61L; and (b) a gain-of-function tail mutation for IFNAR2 binding. A non-limiting example of a mutated IFNα2 polypeptide comprising both of mutations (a) and (b) (MDL+α8-tail) is set forth in SEQ ID NO: 12 and is encoded by the nucleotide molecule set forth in SEQ ID NO: 22. Each possibility represents a separate embodiment of the present invention.

In another embodiment, the present invention provides a mutated IFNα2 polypeptide comprising both (a) at least 2 of the mutations H57Y, E58L, and Q61D; and (b) a gain-of-function tail mutation for IFNAR2 binding (e.g. the α8-tail mutation). In another embodiment, the IFNα2 polypeptide comprises both (a) all 3 of the mutations H57Y, E58L, and Q61 D; and (b) a gain-of-function tail mutation for IFNAR2 binding. A non-limiting example of a mutated IFNα2 polypeptide comprising both of mutations (a) and (b) (YLD+α8-tail) is set forth in SEQ ID NO: 46. Each possibility represents a separate embodiment of the present invention.

In another embodiment, the present invention provides a mutated IFNα2 polypeptide comprising both (a) at least 2 of the mutations H57Y, E58A, and Q61S; and (b) a gain-of-function tail mutation for IFNAR2 binding (e.g. the α8-tail mutation). In another embodiment, the IFNα2 polypeptide comprises both (a) all 3 of the mutations H57Y, E58A, and Q61 S; and (b) a gain-of-function tail mutation for IFNAR2 binding. A non-limiting example of a mutated IFNα2 polypeptide comprising both of mutations (a) and (b) (YAS+α8-tail) is set forth in SEQ ID NO: 47. Each possibility represents a separate embodiment of the present invention.

In another embodiment, the present invention provides a mutated IFNα2 polypeptide comprising both (a) a loss-of-function mutation for IFNAR1-binding in residues H57, E58, Q61, N65, L80, Y85, and/or Y89; and (b) a gain-of-function tail mutation for IFNAR2 binding. As provided herein, Type I interferons first bind IFNAR2, then transiently recruit IFNAR1 to the complex, forming the ternary complex which mediates signaling. Occupancy of IFNAR2 by a mutated IFNα2 polypeptide thus antagonizes IFNAR signaling by preventing binding of signaling-competent IFN to the receptor. The effect is enhanced by gain-of-function tail mutations for IFNAR2 binding, which increase occupancy of IFNAR2 by the mutated IFNα2 polypeptide. Thus, the present invention shows that combination of these two mutations (a) and (b) further enhances IFNAR antagonist activity by mutated IFNα2 polypeptides of the present invention, relative to mutated IFNα2 polypeptides having either (a) or (b) alone.

In another embodiment, the present invention provides a mutated IFNα2 polypeptide comprising both (a) at least 2 of the mutations selected from N65A, L80A, Y85A, and Y89A; and (b) a gain-of-function tail mutation for IFNAR2 binding (e.g. the α8-tail mutation). In another embodiment, the IFNα2 polypeptide comprises both (a) at least 3 mutations selected from N65A, L80A, Y85A, and Y89A; and (b) a gain-of-function tail mutation for IFNAR2 binding. Each possibility represents a separate embodiment of the present invention. In another embodiment, the IFNα2 polypeptide comprises both (a) all 3 of the mutations L80A, Y85A, and Y89A; and (b) a gain-of-function tail mutation for IFNAR2 binding. In another embodiment, the IFNα2 polypeptide comprises both (a) all four of the mutations N65A, L80A, Y85A, and Y89A; and (b) a gain-of-function tail mutation for IFNAR2 binding. Non-limiting examples of mutated IFNα2 polypeptides comprising both of mutations (a) and (b) (NLYY or LYY+α8-tail) are set forth in SEQ ID NO: 9 and 48. Each possibility represents a separate embodiment of the present invention.

In another embodiment, the present invention provides a mutated IFNα2 polypeptide comprising both (a) at least 2 of the mutations selected from H57A, E58A, and Q61A; and (b) a gain-of-function tail mutation for IFNAR2 binding (e.g. the α8-tail mutation). In another embodiment, the IFNα2 polypeptide comprises both (a) all 3 of the mutations H57A, E58A, and Q61A; and (b) a gain-of-function tail mutation for IFNAR2 binding. A non-limiting example of a mutated IFNα2 polypeptide comprising both of mutations (a) and (b) (HEQ+α8-tail) is set forth in SEQ ID NO: 8. Each possibility represents a separate embodiment of the present invention.

In another embodiment, the present invention provides mutated IFNα2 polypeptide, comprising a mutation of a residue selected from the group consisting of E159, S160, L161, S163, and E165, and combinations thereof, to a residue selected from the group consisting of lysine and arginine. An example of such a mutated IFNα2 polypeptide is set forth in SEQ ID NO: 7 and is encoded by the nucleotide molecule set forth in SEQ ID NO: 17.

In another embodiment, the present invention provides mutated IFNα2 polypeptide, comprising a substitution mutation of the 5-10 C-terminal residues of the mutated IFNα2 polypeptide to a sequence selected from the group consisting of KRLKSKE (SEQ ID NO: 43) and KRLKSK (SEQ ID NO: 44).

As provided herein, mutants of IFNα2 that increase the net positive charge of the tail region, whether or not in combination with other mutations of the present invention, exhibit enhanced affinity for IFNAR2, enhanced IFNAR signaling, and enhanced biological activity relative to wt Type I interferons, e.g. IFNα2 and IFNβ.

In another embodiment, the additional mutation in the C-terminal tail results in the 7 carboxy-terminal residues of the mutated IFNα2 polypeptide having a net positive charge. In another embodiment, the additional mutation results in these residues having a net charge of +2. In another embodiment, the net charge of these residues after mutation is +2 or higher. In another embodiment, the net charge of these residues is +3. In another embodiment, the net charge of these residues is +3 or higher. In another embodiment, the net charge of these residues is +3 or +4. In another embodiment, the net charge of these residues is +4. In another embodiment, the net charge of these residues is +4 or higher. Each possibility represents a separate embodiment of the present invention.

In another embodiment, the additional mutation in the C-terminal tail is a substitution of the 5-10 C-terminal residues of the mutated IFNα2 polypeptide to a sequence selected from KRLKSKE (SEQ ID NO: 43) and KRLKSK (SEQ ID NO: 44). In another embodiment, the sequence that is replaced is ESLRSKE (SEQ ID NO: 42). An example of such a mutated IFNα2 polypeptide is set forth in SEQ ID NO: 7 and is encoded by SEQ ID NO: 17. Each possibility represents a separate embodiment of the present invention.

In another embodiment, a mutated IFNα2 polypeptide of methods and compositions of the present invention further comprises an additional mutation in a residue selected from (a) leucine at position 30 (L30), (b) arginine at position 33 (R33), (c) methionine at position 148 (M148), and (d) serine at position 153 (S153), and combinations thereof, wherein the additional mutation decreases affinity of the mutated IFNα2 polypeptide for the IFNAR2 subunit of the IFNAR (e.g. a human IFNAR. In another embodiment, the residue is mutated to an alanine residue. In another embodiment, the mutated IFNα2 polypeptide comprises 1 of mutations (a-d). In another embodiment, the mutated IFNα2 polypeptide comprises 2 of mutations (a-d). In another embodiment, the mutated IFNα2 polypeptide comprises more than 1 of mutations (a-d). Each possibility represents a separate embodiment of the present invention.

Preferred derivatives of the present invention include improved IFNα2_polypeptides that have been fused with another compound, such as a compound to increase the half-life of the polypeptide and/or to reduce potential immunogenicity of the polypeptide (for example, polyethylene glycol, "PEG"). PEG can be used to impart water solubility, size, slow rate of kidney clearance, and reduced immunogenicity to the fusion protein. See, e.g., U.S. Pat. No. 6,214,966. In the case of PEGylations, the fusion of the improved IFNα2 polypeptide to PEG can be accomplished by any means known to one skilled in the art. For example, PEGylation can be accomplished by first introducing a cysteine residue into the improved IFNα2 polypeptide (e.g. at the C-terminus), followed by site-specific derivatization with PEG-maleimide. Preferred polyethylene-glycol-IFNα2 mutant conjugates are reversible conjugates that are slowly converted to the drugs under physiological conditions, such as according to the methods described in WO 2004/089280 (also see Tsutsumi Y et al, Proc. Natl. Acad. Sci. USA 97: 8548-8553, 2000).

Other IFNα2 mutant conjugates can be prepared by coupling an IFNα2 mutant to a water-soluble polymer. A non-limiting list of such polymers includes other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alpha-polymer conjugates are described in U.S. Pat. No. 4,766,106 and U.S. Pat. No. 4,917,888.

"Improved IFNAR agonist activity" refers, preferably, to a 2-fold improvement in IFNAR agonist activity relative to wt IFNα2 (i.e. an improved activity 2-fold greater than the wt activity). In another embodiment, the term refers to a 20% improvement. In another embodiment, the term refers to a 30% improvement. In another embodiment, the term refers to a 50% improvement. In another embodiment, the term refers to a 70% improvement. In another embodiment, the term refers to a 2.5-fold improvement. In another embodiment, the term refers to a 3-fold improvement. In another embodiment, the term refers to a 4-fold improvement. In another embodiment, the term refers to a 5-fold improvement. In another embodiment, the term refers to a 7-fold improvement. In another embodiment, the term refers to a 10-fold improvement. In another embodiment, the term refers to a greater than 10-fold improvement. Methods for measuring IFNAR agonist activity are well known in the art, and include, for example, assays for anti-proliferative activity, anti-viral activity, and anti-tumor activity (e.g. as exemplified herein), and assays for STAT phosphorylation and/or activation (e.g. as exemplified in Kalie E et al, An interferon alpha2 mutant optimized by phage display for IFNAR1 binding confers specifically enhanced antitumor activities. J Biol Chem 282 (15):11602-11, 2007). Each possibility represents a separate embodiment of the present invention.

In another embodiment, the present invention provides a nucleotide molecule (e.g. a DNA molecule, RNA molecule, or other type of nucleotide molecule) encoding a mutated IFNα2 polypeptide of the present invention. In another embodiment, the present invention provides a pharmaceutical composition comprising a nucleotide molecule of the present invention. In another embodiment, the present invention provides a vector comprising a nucleotide molecule of the present invention. Preferably, the vector is capable of expressing a mutant IFNα2 polypeptide in a prokaryotic host cell or eukaryotic host cell. In another embodiment, the present invention provides a pharmaceutical composition comprising a vector of the present invention. In another embodiment, the present invention provides a host cell comprising a nucleotide molecule of the present invention. In another embodiment, the present invention provides a pharmaceutical composition comprising a host cell of the present invention. In another embodiment, the vector is operably linked to one or more transcription control elements. Each possibility represents a separate embodiment of the present invention.

In another embodiment, the present invention provides a pharmaceutical composition comprising as an active ingredient a mutated IFNα2 polypeptide of the present invention, and further comprising a pharmaceutically acceptable carrier.

In another embodiment, the present invention provides a method of treating or ameliorating a cancer in a subject in need thereof, wherein the cancer is a cancer known to be responsive to treatment with recombinant interferon-beta, the method comprising the step of administering to the subject a pharmaceutical composition containing an IFNAR-agonistic mutant IFNα2 polypeptide of the present invention, thereby treating or ameliorating a cancer in a subject in need thereof. In another embodiment, the cancer is a cancer known to be responsive to treatment with IFNAR agonists. In another embodiment, a mutated IFNα2 polypeptide of the present invention is administered to the subject. In another embodiment, a nucleotide molecule of the present invention is administered to the subject. In another embodiment, a therapeutically effective amount of the pharmaceutical composition, polypeptide, or nucleotide molecule is administered. Each possibility represents a separate embodiment of the present invention.

The cancer that is treated by methods of a present invention is, in another embodiment, hepatocellular carcinoma. In another embodiment, the cancer is hairy cell leukemia. In another embodiment, the cancer is Kaposi's sarcoma. In another embodiment, the cancer is multiple myeloma. In another embodiment, the cancer is chronic myelogenous leukemia. In another embodiment, the cancer is non-Hodgkin's lymphoma. In another embodiment, the cancer is a melanoma. In another embodiment, the cancer is basal cell carcinoma. In another embodiment, the cancer is a bladder carcinoma. In another embodiment, the cancer is a renal cell carcinoma. In another embodiment, the cancer is any other cancer known to be responsive to treatment with recombinant interferon-beta or IFNAR agonists. Each possibility represents a separate embodiment of the present invention.

The term "cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: apudoma, choristoma, branchioma, malignant carcinoid syndrome, carcinoid heart disease, carcinoma (e.g., Walker, basosquamous, Brown-Pearce, ductal, Ehrlich tumor, non-small cell lung, oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, plasmacytoma, reticuloendotheliosis, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

In another embodiment, the present invention provides a method of treating or ameliorating an infectious disease in a subject in need thereof, wherein the infectious disease is known to be responsive to treatment with recombinant interferon-beta, the method comprising the step of administering to the subject a pharmaceutical composition containing an IFNAR-agonistic mutant IFNα2 polypeptide of the present invention, thereby treating or ameliorating an infectious disease in a subject in need thereof. In another embodiment, the infectious disease is known to be responsive to treatment with IFNAR agonists. In another embodiment, a mutated IFNα2 polypeptide of the present invention is administered to the subject. In another embodiment, a nucleotide molecule of the present invention is administered to the subject. In another embodiment, a therapeutically effective amount of the pharmaceutical composition, polypeptide, or nucleotide molecule is administered. Each possibility represents a separate embodiment of the present invention.

The infectious disease that is treated by methods of the present invention is, in another embodiment, hepatitis. In another embodiment, the disease is hepatitis A. In another embodiment, the disease is hepatitis B. In another embodiment, the disease is hepatitis C. In another embodiment, the disease is *salmonella* (e.g. *S. typhi*) infection. In another embodiment, the disease is any other infectious disease known to be responsive to treatment with recombinant interferon-beta or IFNAR agonists. Each possibility represents a separate embodiment of the present invention.

In another embodiment, the present invention provides a method of treating or ameliorating an autoimmune disease in a subject in need thereof, wherein the autoimmune disease is known to be responsive to treatment with recombinant interferon-beta, the method comprising the step of administering to the subject the pharmaceutical composition containing an IFNAR-agonistic mutant IFNα2 polypeptide of the present invention, thereby treating or ameliorating an autoimmune disease in a subject in need thereof a disease known to be responsive to treatment with IFNAR agonists. In another embodiment, a mutated IFNα2 polypeptide of the present invention is administered to the subject. In another embodiment, a nucleotide molecule of the present invention is administered to the subject. In another embodiment, a therapeutically effective amount of the pharmaceutical composition, polypeptide, or nucleotide molecule is administered. Each possibility represents a separate embodiment of the present invention.

The autoimmune disease treated by methods of the present invention is, in another embodiment, multiple sclerosis (MS). As provided herein, mutated IFNα2 proteins of the present invention upregulate many IFN-responsive genes, e.g. VIP, which has been shown to prevent multiple sclerosis in a mouse model.

In another embodiment, the MS is relapsing remitting MS. In another embodiment, the MS is secondary progressive MS. In another embodiment, the MS is primary progressive MS. In another embodiment, the MS is progressive relapsing MS. In another embodiment, the MS is the MS is selected from the group consisting of relapsing remitting MS, secondary progressive MS, primary progressive MS, and progressive relapsing MS. "Treating MS" as used herein covers the treatment of disease-state in a subject, which disease-state is characterized by symptoms associated with MS, such as weakness, numbness, tremor, loss of vision, pain, paralysis, loss of balance, bladder and bowel dysfunction, and cognitive changes (primary symptoms); repeated urinary tract infections, disuse weakness, poor postural alignment and trunk control, muscle imbalance, decreased bone density, shallow, inefficient breathing, and bedsores (secondary symptoms); and depression (tertiary symptoms), and includes: (i) inhibiting the condition, i.e., arresting its development; or (ii) relieving the condition, i.e., causing regression of the condition. Each possibility represents a separate embodiment of the present invention.

In another embodiment, the autoimmune disease is any other autoimmune disease known to be responsive to treatment with recombinant interferon-beta or IFNAR agonists. Each possibility represents a separate embodiment of the present invention.

As provided herein, certain of the mutated IFNα2 polypeptides of the present invention containing gain-of-function mutations in residues 57, 58, and/or 61 (e.g. YNS, MDL, YLD, and YAS) exhibit an increased affinity for IFNAR1. This increased affinity results in enhanced biological activity compared to wt IFNα2, e.g. anti-proliferative activity, reminiscent of, and in some cases even exceeding, IFNβ. For example, YNS exhibits extremely high anti-proliferative activity that was sufficient to completely eradicate human breast cancer cell xenographs (Example 10). These mutated IFNα2 polypeptides thus have utility in treating tumors, diseases, and disorders responsive to recombinant Type I IFN. Moreover, mutated IFNα2 polypeptides of the present invention are expected to exert fewer unwanted side effects, due to their higher potency, resulting in a lower effective dose. Further, mutated IFNα2 polypeptides of the present invention exhibit the advantage of increased bioavailability relative to Gilli F, Neutralizing antibodies against IFN-beta in multiple sclerosis: antagonization of IFN-beta mediated suppression of MMPs. Brain 127(2):259-68, 2004; Villa E et al, Alpha but not beta interferon is useful in chronic active hepatitis due to hepatitis C virus. A prospective, double-blind, randomized study. Dig Dis Sci 41(6):1241-7, 1996). As further provided herein, mutating the tail region of IFNα2 to increase its net positive charge increases in turn its affinity of IFNAR2. Since ternary complex half-life is affected in an additive fashion by affinity for both IFNAR1 and IFNAR2 (Example 12), combining a gain-of-function mutation in residues 57, 58, and/or 61 with a tail mutation will thus further enhance the potency and efficacy of mutated IFNα2 polypeptides of the present invention.

In another embodiment, the present invention provides a method of treating or ameliorating a disorder or disease associated with excessive activity or expression of a Type I IFN in a subject in need thereof, the method comprising the step of administering to the subject a pharmaceutical composition containing an IFNAR-antagonistic mutant IFNα2 polypeptide of the present invention, thereby treating or ameliorating a disorder or disease associated with excessive activity or expression of a Type I interferon in a subject in need thereof. In another embodiment, a mutated IFNα2 polypeptide of the present invention is administered to the subject. In another embodiment, a nucleotide molecule of the present invention is administered to the subject. In another embodiment, a therapeutically effective amount of the pharmaceutical composition, polypeptide, or nucleotide molecule is administered. Each possibility represents a separate embodiment of the present invention.

The disease associated with excessive Type I IFN activity or expression is, in another embodiment, insulin-dependent diabetes mellitus (IDDM). In another embodiment, a composition of the present invention is used to minimize and/or eliminate one or more symptoms in an IDDM patient. Each possibility represents a separate embodiment of the present invention.

In another embodiment, the disease is systemic lupus erythematosus (SLE). In another embodiment, a composition of the present invention is used to minimize and/or eliminate one or more symptoms in an LE patient. Each possibility represents a separate embodiment of the present invention.

In another embodiment, the disease or disorder is any other disease or disorder known to be responsive to treatment with IFNAR antagonists. Each possibility represents a separate embodiment of the present invention.

As provided herein, certain of the mutated IFNα2 polypeptides of the present invention containing loss-of-function mutations in residues H57, E58, Q61, N65, L80, Y85, and/or Y89 (e.g. H57A, E58A, Q61A, LYY, and NLYY) exhibit decreased affinity for IFNAR1. This increased affinity results in IFNAR antagonist activity. For example, YNS exhibits extremely high anti-proliferative activity that was sufficient to completely eradicate human breast cancer cell xenographs (Example 10). As further provided herein, mutating the tail region of IFNα2 to increase its net positive charge increases in turn its affinity of IFNAR2. Since ternary complex half-life is affected in an additive fashion by affinity for both IFNAR1 and IFNAR2 (Example 12), combining a gain-of-function mutation in residues 57, 58, and/or 61 with a tail mutation thus further enhances the potency and efficacy of mutated IFNα2 polypeptides of the present invention. For example, IFNα2 proteins with the NLYY mutation, either alone or in combination with the α8-tail mutation, are potent antagonists to interferon function through their tight binding to the IFNAR2 receptor, and the lack of binding to the IFNAR1 receptor, making them biologically non-active. Based on the increased level of IFN-α expression in patients with autoimmune diseases such as systemic lupus erythematosus (SLE), IFN-α has been implicated in the pathogenesis of SLE. Treatment with these proteins is therefore beneficial to SLE patients, as it decreases significantly the ability for IFN-α mediated signaling.

In another embodiment, a mutated IFNα2 polypeptide of the present invention is a mutated version of SEQ ID NO: 2:
MALTFALLVALLVLSCKSSCSVGCDLPQTHSLGSR RTLMLLAQMRRISLFSCL KDRHDFGFPQEEFGNQFQ-KAETIPVLHEMIQQIFNLFSTKDSSAAW-DETLLDKFYTEL YQQLNDLEACVIQGVGVTET-PLMKEDSILAVRKYFQRITLYLKEKKYSPCAWEVVRA EIMRSFSLSTNLQESLRSKE (SEQ ID NO: 2; GenBank Accession No: NM_000605. The signal peptide, whose residues are not included in the numbering scheme used herein, is underlined). In other words, the mutated IFNα2 polypeptide differs from SEQ ID NO: 2 by a mutation or combination of mutations of the present invention. In another embodiment, the mutated IFNα2 polypeptide is a mutated version of a variant of SEQ ID NO: 2. In another embodiment, the mutated IFNα2 polypeptide is a mutated version of a homologue of SEQ ID NO: 2. In another embodiment, the mutated IFNα2 polypeptide is a mutated version of an isomer of SEQ ID NO: 2. In another embodiment, the mutated IFNα2 polypeptide is a mutated version of a fragment of SEQ ID NO: 2. In another embodiment, the mutated IFNα2 polypeptide is a mutated version of a fragment of a variant of SEQ ID NO: 2. In another embodiment, the mutated IFNα2 polypeptide is a mutated version of a fragment of a homologue of SEQ ID NO: 2. In another embodiment, the mutated IFNα2 polypeptide is a mutated version of a fragment of an isomer of SEQ ID NO: 2.

An exemplary nucleotide molecule encoding a mutated IFNα2 polypeptide is set forth in SEQ ID NO: 49, which encodes the wt IFNα2a protein set forth in SEQ ID NO: 2:
agaacctagagcccaaggttcagagt-cacccatctcagcaagcccagaagtatctgcaatatctacgatggcctcgcccttt gcttactgatggtcctggtggtgct-cagctgcaagtcaagct-gctctctgggctgtgatctccctgagacccacagcctggataacagg aggacct-tgatgctcctggcacaaatgagcagaatctctccttcctcctgtctgatggacagac atgactttggattccccaggaggagtt tgatggcaaccagttccagaaggctc-cagccatctctgtcctccatgagct-gatccagcagatcttcaacctcttaccacaaaagattcat ctgctgcttgggatgag-gacctcctagacaaattctgcaccgaactctaccagcagctgaatgacttggaagc ctgtgtgatgcaggag gagagggtgggagaaactcccctgat-gaatgcggactccatcttggctgtgaa-gaaatacttccgaagaatcactctctatctgacaga gaagaaatacagcccttgt-gcctgggaggttgtcagagcagaaatcatgagatccctctctttatcaacaaactt gcaagaaagattaag gaggaaggaataacatctggtccaacat-gaaaacaattcttattgactcatacac-caggtcacgctttcatgaattctgtcatttcaaagact ctcacccctgctataactat-gaccatgctgataaactgatttatctatttaaatatttatttaactattcataagatttaaa ttatttttgttcatataa cgtcatgtgcaccttacactgtggt-tagtgtaataaaacatgttccttatatttactc (SEQ ID NO: 49; GenBank Accession No: NM_000605). In another embodiment, a mutated IFNα2 polypeptide of the present invention is encoded by a mutated version of SEQ ID NO: 49. In another embodiment, the mutated IFNα2 polypeptide is encoded by a mutated version of a homologue of SEQ ID NO: 49. In another embodiment, the mutated IFNα2 polypeptide is encoded by a mutated version of an isomer of SEQ ID NO: 49. In another embodiment, the mutated IFNα2 polypeptide is encoded by a mutated version of a fragment of SEQ ID NO: 49. In another embodiment, the mutated IFNα2 polypeptide is encoded by a mutated version of a fragment of a variant of SEQ ID NO: 49. In another embodiment, the mutated IFNα2 polypeptide is encoded by a mutated version of a fragment of a homologue of SEQ ID NO: 49. In another embodiment, the mutated IFNα2 polypeptide is encoded by a mutated version of a fragment of an isomer of SEQ ID NO: 49.

Representative, non-limiting examples of amino acid sequences of mutants of the present invention (not including the signal peptide) are presented below, with mutated residues underlined:

```
                                      (HEQ; SEQ ID NO: 5)
CDLPQTHSLGSRRTLMLLAQMRRISLFSCLKDRHDFGFPQEEFGNQFQKA

ETIPVLAAMIAQIFNLFSTKDSSAAWDETLLDKFYTELYQQLNDLEACVI

QGVGVTETPLMKEDSILAVRKYFQRITLYLKEKKYSPCAWEVVRAEIMRS

FSLSTNLQESLRSKE.

(NLYY; SEQ ID NO: 6)
CDLPQTHSLGSRRTLMLLAQMRRISLFSCLKDRHDFGFPQEEFGNQFQKA

ETIPVLHEMIQQIFNLFSTKDSSAAWDETALDKFATELAQQLNDLEACVI

QGVGVTETPLMKEDSILAVRKYFQRITLYLKEKKYSPCAWEVVRAEIMRS

FSLSTNLQESLRSKE (a8-tail; SEQ ID NO: 7)
CDLPQTHSLGSRRTLMLLAQMRRISLFSCLKDRHDFGFPQEEFGNQFQKA

ETIPVLHEMIQQIFNLFSTKDSSAAWDETLLDKFYTELYQQLNDLEACVI

QGVGVTETPLMKEDSILAVRKYFQRITLYLKEKKYSPCAWEVVRAEIMRS

FSLSTNLQKRLKSKE (MDL; SEQ ID NO: 10)
CDLPQTHSLGSRRTLMLLAQMRRISLFSCLKDRHDFGFPQEEFGNQFQKA

ETIPVLMDMILQIFNLFSTKDSSAAWDETLLDKFYTELYQQLNDLEACVI

QGVGVTETPLMKEDSILAVRKYFQRITLYLKEKKYSPCAWEVVRAEIMRS

FSLSTNLQESLRSKE.

(YNS; SEQ ID NO: 11)
CDLPQTHSLGSRRTLMLLAQMRRISLFSCLKDRHDFGFPQEEFGNQFQKA

ETIPVLYNMISQIFNLFSTKDSSAAWDETLLDKFYTELYQQLNDLEACVI

QGVGVTETPLMKEDSILAVRKYFQRITLYLKEKKYSPCAWEVVRAEIMRS

FSLSTNLQESLRSKE.

(YNS + α8-tail; SEQ ID NO: 13)
CDLPQTHSLGSRRTLMLLAQMRRISLFSCLKDRHDFGFPQEEFGNQFQKA

ETIPVLYNMISQIFNLFSTKDSSAAWDETLLDKFYTELYQQLNDLEACVI

QGVGVTETPLMKEDSILAVRKYFQRITLYLKEKKYSPCAWEVVRAEIMRS

FSLSTNLQKRLKSKE.
```

The numbering utilized herein does not include the residues of the signal peptide (which is MALTFALLVALLV-LSCKSSCSVG [SEQ ID NO: 50], 23 residues in length, in the case of IFNα2).

The IFNα2 utilized herein is 165 amino acids long. As mentioned hereinabove, Type I IFN variants of different lengths exist. It will be understood by one skilled in the art that the numbering of corresponding mutations in such variants must be adjusted by the shift, if any, in the positions of the corresponding residues. For example, IFNα1 (SEQ ID NO: 1) is 166 amino acids long, and the positions of H57 and all subsequent residues are shifted by +1.

In another embodiment, a mutated IFNα2 polypeptide of the present invention is a mutated version of an IFNα2b protein (e.g. SEQ ID NO: 2). In another embodiment, the mutated IFNα2 polypeptide is a mutated version of an IFNα2a protein (e.g. SEQ ID NO: 51). In another embodiment, the mutated IFNα2 polypeptide is a mutated version of an IFNα2c protein (e.g. SEQ ID NO: 52). Each possibility represents a separate embodiment of the present invention.

The terms "mutated IFNα2 polypeptide" and "IFNα2 polypeptide" refer, in another embodiment, to a full-length IFNα2 protein, e.g. a mutated protein that is the same length as the wild-type protein. In another embodiment, the term refers to an IFNα2 protein containing mutations according to the present invention, wherein the IFNα2 protein is also truncated. Preferably, a truncated IFNα2 protein retains IFN activity, e.g. detectable binding to IFNAR1 and/or IFNAR2, as desired (i.e. binding to both for IFNAR agonistic IFNα2 proteins and binding to at least IFNAR2 for IFNAR antagonistic IFNα2 proteins). In another embodiment, truncated mutant IFNAR agonistic IFNα2 proteins fall within the scope of the present invention if the truncation does not result in a significant loss of activity, relative to a full-length IFNα2 protein containing the same mutations. Each possibility represents a separate embodiment of the present invention.

The term "recombinant proteins or polypeptides" refer to proteins or polypeptides produced by recombinant DNA techniques, i.e., produced from cells, prokaryotic or eukaryotic, including e.g., microbial or mammalian, transformed by an exogenous recombinant DNA expression construct encoding the desired protein or polypeptide. Proteins or polypeptides expressed in most bacterial cultures will typically be free of glycan. Proteins or polypeptides expressed in yeast may have a glycosylation pattern different from that expressed in mammalian cells.

"IFNα agonist" refers to an agent capable of signaling via IFNAR, thereby mediating a biological activity of IFNα in vivo, at least to a degree sufficient to exert therapeutic activity (e.g. to cancer or hepatitis infection). IFNα is known to possess a plurality of biological activities. The agonists for use herein will stimulate any one or more of these activities. Ordinarily the antagonist will stimulate at least one (and preferably a plurality) of the antiviral, anti-proliferative or the immunomodulatory activity of IFNα.

"IFNα antagonist" refers to an agent capable of interfering with a biological activity of IFNα in vivo. It is not necessary that the antagonist completely neutralizes the IFNα activity, but only that it do so to a degree sufficient to exert therapeutic activity (e.g. to IDDM or SLE). IFNα is known to possess a plurality of biological activities. The antagonists for use herein will reduce, inhibit or neutralize any one or more of these activities. Ordinarily the antagonist will interfere with at least one (and preferably a plurality) of the antiviral, anti-proliferative or the immunomodulatory activity of IFNα.

An "expression vector" as used herein refers to a nucleic acid molecule capable of replication and expressing a gene of interest when transformed, transfected or transduced into a host cell. The expression vectors comprise one or more phenotypic selectable markers and an origin of replication to ensure maintenance of the vector and to, if desired, provide amplification within the host. Selectable markers include, for example, sequences conferring antibiotic resistance markers, which may be used to obtain successful transformants by selection, such as ampicillin, tetracycline and kanamycin resistance sequences, or supply critical nutrients not available from complex media. Suitable expression vectors may be plasmids derived, for example, from pBR322 or various pUC plasmids, which are commercially available. Other expression vectors may be derived from bacteriophage, phagemid, or cosmid expression vectors, all of which are described in sections 1.12-1.20 of Sambrook et al., (Molecular Cloning: A Laboratory Manual. $3^{rd}$ edn., 2001, Cold Spring Harbor Laboratory Press). Isolated plasmids and DNA fragments are cleaved, tailored, and ligated together in a specific order to generate the desired vectors, as is well known in the art (see, for example, Sambrook et al., ibid).

"Therapeutically effective amount" refers to that amount of an improved IFNα2 polypeptide of the invention which, when administered to a subject in need thereof, is sufficient to effect treatment of the condition or disorder.

Characteristics of the Improved IFNα2 Polypeptides of the Invention

Specific mutations of the IFNα2 mutants of the invention are each located at three different positions, and therefore can be combined to yield additional, or increased effects. The present invention provides variants comprising a combination of 3 point mutations, e.g. HEQ, MDL, or YNS; and the substitution of KRLKSKE (SEQ ID NO: 43) for the C terminal sequence ESLRSKE (SEQ ID NO: 42). The enhanced binding potency of such mutants is useful in overcoming the problem of IFNAR down-regulation in cancer cells.

A nucleic acid molecule can be produced using recombinant DNA technology (e.g., polymerase chain reaction (PCR) amplification, cloning) or chemical synthesis. Nucleic acid sequences include natural nucleic acid sequences and homologs thereof, comprising, but not limited to, natural allelic variants and modified nucleic acid sequences in which nucleotides have been inserted, deleted, substituted, and/or inverted in such a manner that such modifications do not substantially interfere with the nucleic acid molecule's ability to encode the recombinant IFNα2 polypeptides of the present invention.

A polynucleotide or oligonucleotide sequence can be deduced from the genetic code of a protein, however, the degeneracy of the code must be taken into account, and nucleic acid sequences of the invention also include sequences, which are degenerate as a result of the genetic code, which sequences may be readily determined by those of ordinary skill in the art.

The terms "nucleic acid" and "polynucleotide" as used herein refer to an oligonucleotide, polynucleotide or nucleotide and fragments or portions thereof, and to DNA or RNA of genomic or synthetic origin, which may be single- or double-stranded, and represent the sense or antisense strand. The term should also be understood to include, as equivalents, analogs of either RNA or DNA made from nucleotide analogs, and, as applicable to the embodiment being described.

Expression and Purification of Mutated IFNα2 Polypeptides of the Present Invention There are several methods of expressing and purifying recombinant human IFNα2 in bacteria, in particular in *E. coli*, to obtain IFNα2 polypeptides having improved agonist or antagonist activity. Known methods can be used to express the cloned genes in bacteria. To obtain high-level expression of a cloned eukaryotic gene in a prokaryotic system, it is preferable to construct expression vectors that contain a strong promoter to direct mRNA transcription.

Examples of regulatory regions suitable for this purpose are the promoter and operator region of the *E. coli* beta-glucosidase gene, the *E. coli* tryptophan biosynthetic pathway, or the leftward promoter from phage A. The inclusion of selection markers in DNA plasmids transformed in *E. Coli* is also useful. Examples of such markers include the genes specifying resistance to ampicillin, tetracycline, or chloramphenicol. Post-translational modifications, such as glycosylation, do not occur in the prokaryotic cell expression system *E. coli*. In addition, proteins with complex disulfide patterns are can be misfolded when expressed in *E. coli*. With the prokaryotic system, the expressed protein is either present in the cell cytoplasm in an insoluble form, in so-called inclusion bodies, found in the soluble fraction after the cell has lysed, or is directed into the periplasm by the addition of appropriate secretion signal sequences. If the expressed protein is in insoluble inclusion bodies, solubilization and subsequent refolding of the inclusion bodies are usually required.

Analogs, Fragments, Derivatives, and Variants of Improved IFNα2 Polypeptides

An analog, fragment, derivative, or variant of the improved IFNα2 polypeptides of the present invention may be: (i) one in which one or more of the amino acid residues are substituted with a conserved or non-conserved amino acid residue; or (ii) one in which one or more of the amino acid residues includes a substitute group; or (iii) one in which the improved IFNα2 polypeptide is fused with another compound, such as a compound to increase the half-life of the improved IFNα2 polypeptide (for example, polyethylene glycol); or (iv) one in which additional amino acids are fused to the mature, improved IFNα2 polypeptide, such as a leader or secretory sequence or a sequence which is employed for purification of the mature, improved IFNα2 polypeptide; or (v) one in which the improved IFNα2 polypeptide sequence is fused with a larger polypeptide, i.e., human albumin, an antibody or Fc, for increased duration of effect. Such analogs, fragments, derivatives, and variants are deemed to be within the scope of those skilled in the art from the teachings herein. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamin, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Non-conservative substitutions would not be made for conserved amino acid residues or for amino acid residues residing within a conserved protein domain. Fragments or biologically active portions include polypeptide fragments suitable for use as a medicament, as a research reagent, and the like. Fragments include peptides comprising amino acid sequences sufficiently similar to or derived from the amino acid sequences of an improved IFNα2 polypeptide of this invention and exhibiting at least one activity of that polypeptide, but which include fewer amino acids than the full-length polypeptides disclosed herein. Typically, biologically active portions comprise a domain or motif with at least one activity of the polypeptide. Such biologically active portions can be prepared synthetically or by recombinant techniques and can be evaluated for one or more of the functional activities of a polypeptide of this invention by means disclosed herein and/or well known in the art.

It will be understood to one of skill in the art that the present invention encompasses analogs, active fragments, derivatives, and variants of the IFNα2 polypeptides of the present invention. The terms "analog," "active fragment," "derivative," and "variant," when referring to the improved IFNα2 polypeptides of the present invention, means analogs, fragments, derivatives, and variants of such improved IFNα2 polypeptides that retain substantially similar functional activity or substantially the same biological function or activity as the improved IFNα2 polypeptides, as described herein.

An "analog" includes an improved IFNα2 polypeptide wherein at least one amino acid is substituted by another amino acid to produce an active analog of a polypeptide of the invention having increased activity, stability or longer half-life as compared to the polypeptides listed herein.

A "derivative" includes all modifications to an improved IFNα2 polypeptide of this invention that substantially preserve the functions disclosed herein and include additional structure and attendant function, e.g., PEGylated polypeptides, which have greater half-life.

A "variant" includes polypeptides having an amino acid sequence comprising a mutation of this invention that retains substantially similar functional activity or an increased functional activity as compared to the original mutant IFNα2 polypeptide. In another embodiment, variants of the IFNα2 polypeptides of the present invention include polypeptides having an amino acid sequence sufficiently similar to the amino acid sequence of the original improved IFNα2 polypeptides or combinations thereof. Variants include further amino acid sequence modification. Variants with improved activity can be identified by screening combinatorial libraries of mutants, for example truncation or point mutants, of IFNα2 polypeptides of this invention.

"Substantially similar functional activity" means that the degree of biological activity is within about 50% to 100% or more, preferably within 80% to 100% or more, and more preferably within about 90% to 100% or more, of that biological activity demonstrated by the polypeptide to which it is being compared when the biological activity of each polypeptide is determined by the same procedure or assay.

"Similarity" between two polypeptides is determined by comparing the amino acid sequence of one polypeptide to the sequence of a second polypeptide. An amino acid of one polypeptide is similar to the corresponding amino acid of a second polypeptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, P. (1989) EMBO J. 8: 779-785. For example, amino acids belonging to one of the following groups represent conservative changes or substitutions: Ala: -Pro, Gly, Gln, Asn, Ser, Thr; -Cys, Ser, Tyr, Thr; -Val, Ile, Leu, Met, Ala, Phe; -Lys, Arg, His; -Phe, Tyr, Trp, His; and -Asp, Glu.

Pharmaceutical Compositions of the Invention

The invention also provides pharmaceutical compositions that can be administered to a patient to achieve a therapeutic effect. Pharmaceutical compositions of this invention can be prepared for administration by combining an IFNα2 polypeptide of the present invention, having the desired degree of purity in a pharmaceutically effective amount, with pharmaceutically acceptable carriers.

The IFNα2 polypeptides and pharmaceutical compositions of the present invention are useful for parenteral (e.g., intravenous, intramuscular and subcutaneous), topical, oral, inhalable, or local administration.

The polypeptides of the present invention can be used in pharmaceutical compositions, for any suitable method of administration, including but not limited to intravenous, subcutaneous, intramuscular, or intrathecal administration.

Thus, the above described polypeptides preferably will be combined with an acceptable sterile pharmaceutical carrier, such as five percent dextrose, lactated Ringer's solution, normal saline, sterile water, or any other commercially prepared physiological buffer solution designed for intravenous infusion. It will be understood that the selection of the carrier solution, and the dosage and administration of the composition, will vary with the subject and the particular clinical setting, and will be governed by standard medical procedures.

In accordance with the methods of the present invention, these pharmaceutical compositions may be administered in amounts effective to inhibit or ameliorate the pathological consequences or symptoms associated with the target disease or disorder, e.g. hepatitis infection, MS, cancer, IDDM or SLE.

Administration of the improved IFNα2 polypeptides of the present invention may be by bolus intravenous injection, by constant intravenous infusion, or by a combination of both routes. Alternatively, or in addition, the improved IFNα2 polypeptides mixed with appropriate excipients may be taken into the circulation via an intramuscular site.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent a desirable oral dosage form for the pharmaceutical compositions of the present invention.

For topical administration, the improved IFNα2 polypeptides of the present invention may be formulated using bland, moisturizing bases, such as ointments or creams. Examples of suitable ointment bases are petrolatum, petrolatum plus volatile silicones, lanolin and water in oil emulsions.

For administration by inhalation, the IFNα2 polypeptides for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

The improved IFNα2 polypeptides and pharmaceutical compositions of the present invention are particularly useful for intravenous administration. The compositions for administration will commonly comprise a solution of the improved IFNα2 polypeptide dissolved in a pharmaceutical acceptable carrier, preferably in an aqueous carrier. A variety of aqueous carriers can be used, e.g., buffered saline and the like. These solutions are sterile and generally free of undesirable matter. The compositions may be sterilized by conventional, well-known sterilization techniques.

A typical pharmaceutical composition for intravenous administration can be readily determined by one of ordinary skill in the art. The amounts administered are clearly protein specific and depend on its potency and pharmacokinetic profile. Actual methods for preparing parenterally administrable compositions will be known or apparent to those skilled in the art and are described in more detail in such publications as Remington's Pharmaceutical Science, 18t ed., Mack Publishing Company, Easton, Pa., 1990.

The compositions containing the improved IFNα2 polypeptides of the invention or a cocktail thereof (i.e., with other proteins) can be administered in therapeutic treatments. In therapeutic applications, compositions are administered to a patient suffering from MS, cancer, and disorders associated with increased IFNα2 expression of IFNα2 in an amount sufficient to cure or at least partially arrest the disorder. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the improved IFNα2 polypeptides of this invention to effectively treat the patient. Generally, depending on the intended mode of administration, the pharmaceutical acceptable compositions will contain about 1% to about 99% by weight of an improved IFNα2 polypeptide of the invention, and 99% to 1% by weight of a suitable pharmaceutical excipient or carrier. Preferably, the composition will be about 5% to 75% by weight of an improved IFNα2 polypeptide (s) of the invention, with the rest being suitable pharmaceutical excipients or carriers.

The IFNα2 polypeptides of the present invention, or their pharmaceutical acceptable compositions, are administered in a therapeutically effective amount, which will vary depending upon a variety of factors including the activity of the particular improved IFNα2 polypeptide employed; the metabolic stability and length of action thereof; the age, body weight, general health, sex, and diet of the patient; the mode and time of administration; the rate of excretion; the drug combination; the severity of the particular disease-states; and the host undergoing therapy. Generally, a therapeutically effective daily dose is from about 0.1 µg to about 1000 µg/kg of body weight per administration of an improved IFNα2 polypeptide of the invention, preferably, from about 0.5 µg to about 100 µg/kg of body weight per administration. For example, for administration to a 70 kg person, the dosage range would be from about 10 µg to about 100 µg per administration of an improved IFNα2 polypeptide of the invention depending on the treatment regimen. For example, if the improved IFNα2 polypeptide of the invention or formulation containing the polypeptide is administered from one to several times a day, then a lower dose would be needed than if a formulation was administered weekly, or monthly or less frequently.

It is anticipated that IFNα2 polypeptides of the present invention are administered in proper doses. Doses are generally adjusted to at or below the maximum tolerated dose (MTD). Signs indicative of interferon toxicity are noted to be as to hematologic toxicity, anemia, thrombocytopenia, leukopenia: as to gastrointestinal toxicity, diarrhea, dyspepsia, dysphagia, N/V, abdominal pain; as to liver toxicity increases in bilirubin, alk phos and LFTs; as to kidney and bladder, microscopic hematuria, pyuria, azotemia, proteinuria, acute renal failure, nephrotic syndrome, glycosuria, albuminuria; as to pulmonary, orthopnea, dyspnea, bronchospasm, coughing, pulmonary edema, ARDS; as to cardiac toxicity syncope, MI, SVT, bradycardia, tachycardia, dizziness, hyptoension, hypertension. Neurological toxicity are confusion, tremors, numbness, paresthesia, inability to concentrate, somnolence, hallucinations, encephalopathy, seizure, coma, psychomotor retardation, memory dysfunction, dry mouth, sweating, personality disorder, agitation, neuropathy, depression, anxiety, aphasia, retinal infarction with vision loss, eye pain, hemianopsis, taste change, headache, syncope, insomnia. Dermal toxicity of skin rash, urticaria, epidermal necrosis, maculopapular rash is noted. Metabolic toxicity manifests as hyperglycemia. In addition coagulation is monitored for increase in PT/PTT. Also the presence of phyarngitis, alopecia, fatigue, malaise, anorexia, weight loss, fever, chills, myalgia, arthralgia, cyanosis are potential toxic responses to interferon.

Having now generally described the invention, it will be more readily understood through reference to the following examples, which are provided by way of illustration and are not intended to be limiting of the present invention.

EXPERIMENTAL DETAILS SECTION

Materials and Experimental Methods

Examples 1-2

Site-directed mutagenesis. Site-directed mutagenesis was carried out by PCR amplification of the expression plasmid pT72Cα2, which encoded the IFNα2 protein (SEQ ID NO: 2) with 18-21 nucleotide primers containing the mutated codon using high fidelity polymerases pwo (Boehringer Mannheim) and pfu (Stratagene) as described (Piehler, J. & Schreiber, G. 1999, *J. Mol. Biol.* 294, 223-237). After phosphorylation and ligation, mutated plasmids were transformed into *E. coli* TG1 cells. Sequences of whole expressed genes containing mutations were verified by DNA sequencing.

Protein expression and purification. For IFNAR2-EC production, *E. coli* TG1 cells containing pT72CR2 (Piehler J, Schreiber G. Biophysical analysis of the interaction of human ifnar2 expressed in *E. coli* with IFNalpha2. J Mol Biol 28; 289(1):57-67, 1999) were grown at 37° C. in 750 ml of 2×TY medium containing 100 mg/ml ampicillin in two liter flasks. At $A_{600}$=0.6, protein expression was induced by addition of 0.2 mM IPTG and infection with M13/T7 phage at an MOI of 5 plaque forming units per cell (Invitrogen, Carlsbad, Calif.). After four hours of additional growth, cells were pelleted and resuspended in lysis buffer containing 100 mM Tris (pH 8.4), 100 mM NaCl, 1 mM EDTA and lysozyme (50 mg/ml). After sonication, the insoluble fraction was separated by centrifugation and inclusion bodies were washed with lysis buffer that did not contain lysozyme and dissolved by stirring in 8 M urea for 1 hour. Denatured protein was refolded by a 20-fold dilution into 100 mM Tris (pH 8.4). Proteins were extracted by adding a cationic ion-exchange resin (Q SepharoseR Fast Flow; Pharmacia Biotech) to the solution for one hour and filtering beads on a sintered glass funnel. After intensive washing, the protein was eluted with 0.5 M NaCl. Eluted protein was diluted fourfold and directly applied to an ion-exchange column (HiTrap Q, Pharmacia) with a gradient of 0-500 mM NaCl at pH 8.4. Fractions containing major amounts of IFNAR2-EC were pooled and further purified by gel filtration on a SephadexR 75 column (16/26) in 50 mM Tris (pH 8.4) and 100 mM NaCl. All purification steps were analyzed by SDS-PAGE under reducing and non-reducing conditions.

For IFNα2 production, the gene coding for IFNα2 was cloned into the two-cistron expression vector described for IFNAR2, yielding the plasmid pT72Ca2. To improve the level of expression, codons for the first 23 amino acid residues were changed into: TGT GAT CTG CCG CAG ACT CAC TCT CTG GGT TCT CGT CGT ACT CTG ATG CTG CTG GCT CAG ATG CGT CGT (SEQ ID NO: 14). Protein expression and purification were performed as described for IFNAR2-EC, except that inclusion bodies were dissolved in 8 M urea containing 5 mM DTT. IFNα2 was refolded by a 20 fold dilution overnight. Typical yields of protein were 10 mg/l cell culture. IFNα2 migrates as a single 18 kDa band on SDS-PAGE.

IFNAR1-EC was provided by Jacob Piehler, University of Frankford.

Protein concentration determination. Protein concentrations were determined from absorbance at 280 nm with $\epsilon_{280}=18070$ cm$^{-1}$M$^{-1}$ and 26500 cm$^{-1}$M$^{-1}$ for IFNα2 and IFNAR2-EC, respectively. Protein purity was analyzed by SDS-PAGE under non-reducing conditions. Concentrations of active IFNα2 protein were determined for mutants by analytical size-exclusion chromatography with IFNAR2-EC in a Superdex™ 75 HR10/30 column (Pharmacia Biotech). Protein samples of 120 μl with a protein concentration of 1 μM were injected via a 100 μl sample loop. Stoichiometry of the complex was determined by titration with increasing IFNα2 at a constant IFNAR2-EC concentration of 1.45 μM. Area under the IFNα2 peak and the double peak of IFNAR2-EC and the complex were determined by integration. The contribution of IFNα2 to the complex was calculated from the IFNAR2-EC/complex peak by subtracting the area of the original free IFNAR2-EC peak. Resulting peak areas were corrected by extinction coefficients assuming unchanged absorption of the proteins in the complex and normalized by peak areas of free IFNAR2-EC. Relative concentration of IFNα2 in the complex peak was plotted versus relative IFNα2 concentration added in the sample.

Measurements of binding affinity. The interaction between recombinant IFNAR1-EC and IFNα2 was monitored by Reflectometric Interference Spectroscopy (RIfS) under flow-through conditions (Schmitt, H. M., et al., 1997, *Biosens. & Bioelectron.* 12, 809-816). This method detects biomolecular interaction at interfaces as a change in the apparent optical thickness of a thin silica layer. Binding to the surface is monitored as a shift in the interference spectrum. A shift of 1 pm corresponds to approximately 1 pg/mm² protein on the surface. HBS (20 mM HEPES pH 7.5, 150 mM NaCl and 0.01% Triton X100) was used as the running buffer. The non-neutralizing anti-IFNAR1-EC mAb DB2 was coupled to the amino-functionalized dextran AMD 500 surface via its exposed amino groups by amine-coupling chemistry. IFNAR1-EC was affinity captured to the surface, followed by cross-linking with a second mAb, AA3. Determination of the dissociation constant $K_D$ was obtained from the equilibrium response plotted against the protein concentration and fitted according to the law of mass action:

$$\gamma = (K_A c R_{max})/(K_A cn + 1)$$

wherein γ is the signal, $K_A$ is the affinity (in molar), c is the protein concentration, $R_{max}$ is the interference signal at maximum binding, and n is the stoichiometry of the complex, which in this case is 1.

Statistical analysis. The standard error (σ) on $K_D$ for IFNα2-IFNAR2 binding as measured on RIfS was 20% and for relative affinity (wt/mut) 30%. For IFNα2-IFNAR1, σ for $K_D$ is 35% and for relative affinity (wt/mut) 50%. Thus, a two-fold change was significant on the basis of a 2σ (95%) basic confidence level. The magnitude of the error (σ) for individual biological activity measurements (whether antiviral or anti-proliferative) was 35%; thus, a two-fold change between two measurements was significant.

Example 1

Characterization of the IFNα2-IFNAR1-EC Interaction Using an Optical Biosensor System

Figure 1A:
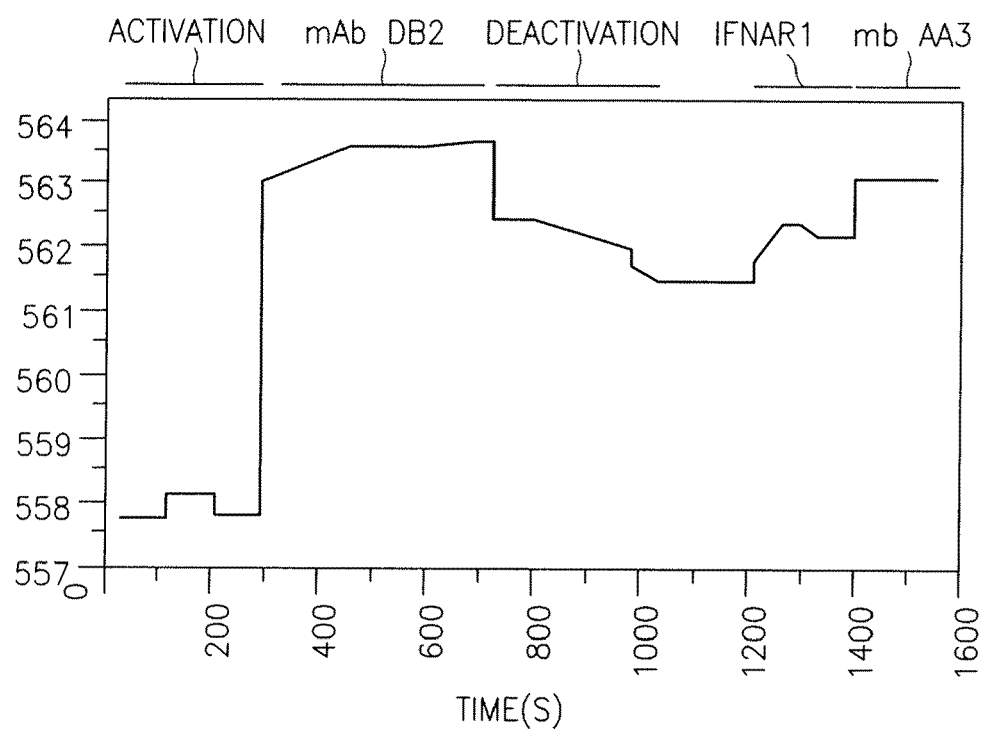
FIGS. 1A, 1B and 1C show the immobilization of type I interferon receptor 1 extracellular domain (IFNAR1-EC) by affinity capture and binding of IFNα2.

Interaction of the type I interferon receptor-extracellular domain (IFNAR1-EC) with wild-type (wt) IFNα2 was characterized in real time by label-free solid-phase detection with RIfS (FIG. 1A) as well as by a Surface Plasmon Resonance based ProteON×36. Binding activity of IFNAR1-EC bound to the RIfS or ProteON surface was determined by injecting IFNα2 protein at concentrations ranging from 0.12 to 4 μM and plotting steady-state response vs. protein concentration according to the law of mass action. Wild type IFNα2 exhibits an affinity constant of 1.5 μM (Lamken, P. et al., 2004, *J Mol Biol* 341: 303-318).

Example 2

Identification of IFNα2 Residues Important for IFNAR1 Binding

Figure 1B:
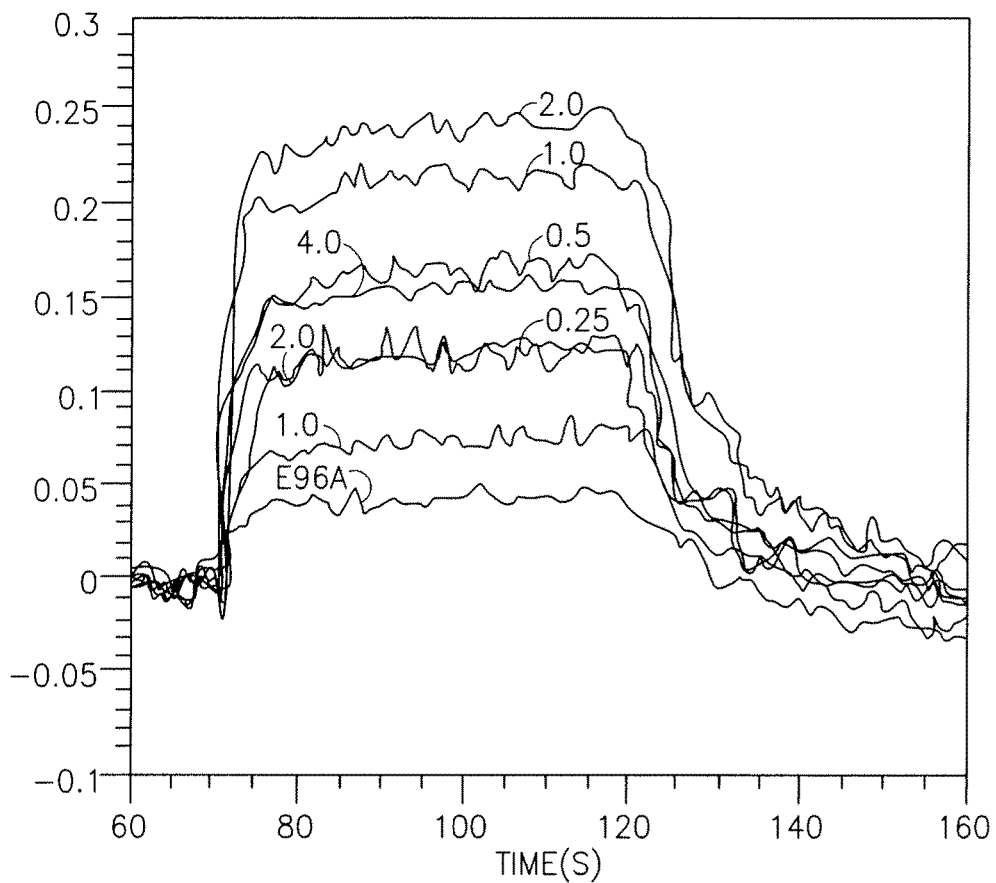
Figure 1C:
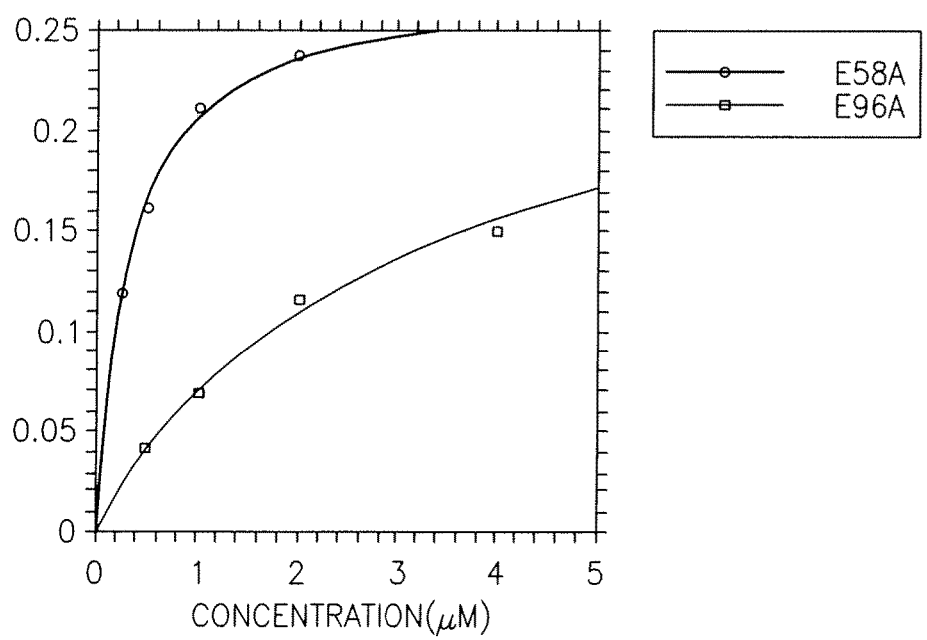
Figure 2B:
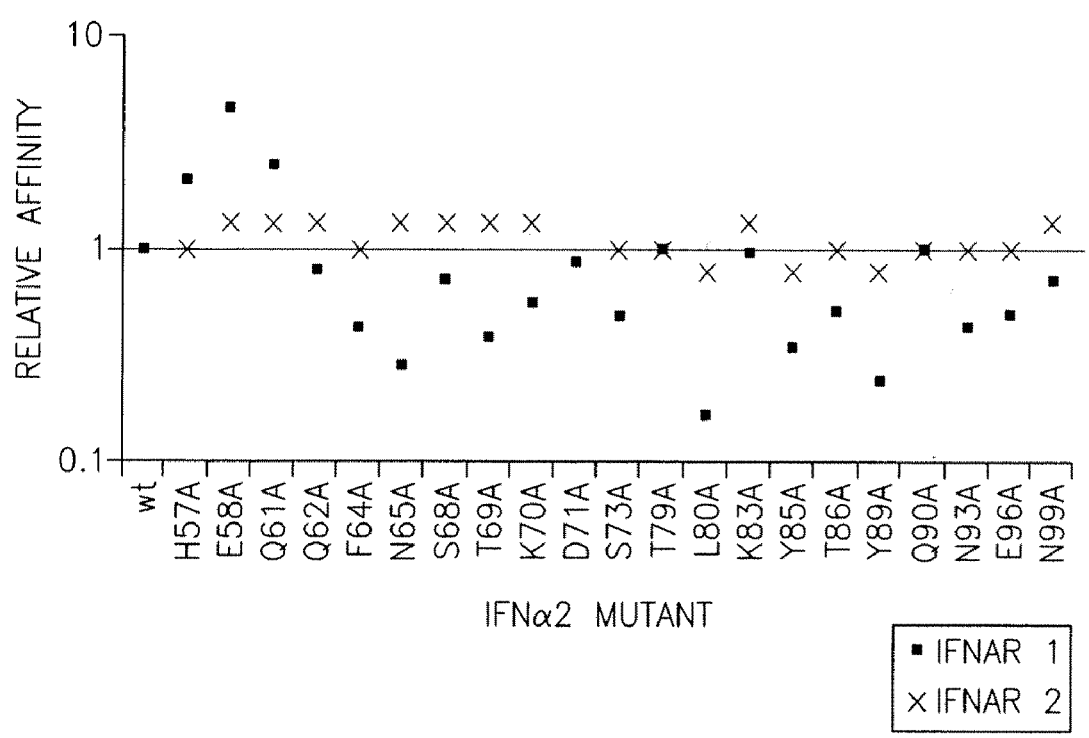

To locate residues important for binding of IFNAR1 to IFNα2, Ala scan of residues located on the B and C helices was performed (FIG. 2). 21 single point mutations were produced, and their binding affinities towards IFNAR2 and IFNAR1 were measured. Three single mutations, H57A, E58A, and Q61A, increased IFNAR1 binding; and six mutations, F64A, N65A, T69A, L80A, Y85A, Y89A, decreased IFNAR1 binding (Table 1B [shown after Example 3] and FIG. 2B). Triple- and quadruple mutants containing the single-mutations L80A, Y85A, Y89A ("LYY"; SEQ ID NO: 45) and N65A, L80A, Y85A, Y89A (SEQ ID NO: 6; "NLYY") were prepared; binding for these proteins was below the threshold of the measurement. Affinities of mutants for IFNAR2 were very similar to wild-type IFNα2, as expected for mutations located on the opposite surface of the IFNAR2 binding site on IFNα2 (Table 1A), thus validating proper folding of all mutant proteins and their active concentrations. FIG. 1B-C depicts an example of steady-state affinity analysis (of E58A and E96A).

Example 3

Combination of 3 Individual Mutations Results in a Large Increase in IFNAR Binding

Materials and Experimental Methods

Protein expression and purification. IFNAR1-EC and IFNAR2-EC carrying a C-terminal decahistidine tag were expressed and purified as described hereinabove.

Results

The H57A, E58A, and Q61A single mutations were combined into a single IFNα2 mutant protein, designated "HEQ" (SEQ ID NO: 5). Binding of HEQ to IFNAR1-EC, IFNAR2-EC, or the formation of the ternary complex including IFNAR1-EC and IFNAR2-EC (each tethered to solidly supported lipid bilayers) was studied by RIfS, SPR, and TIRFS in parallel with wild-type IFNα2 and IFNβ. The lifetime of binary IFN-IFNAR1-EC complexes ($k_d$) was 30-fold greater for HEQ and IFN-β compared to IFN-α2 (FIG. 3A and Table 2). In contrast, association rate constants ($k_a$) were very similar for all three species. From these data, an equilibrium dissociation constant ($K_D$) of 150 nM was determined for the HEQ/IFNAR1-EC complex according to the equation $K_D=k_d/k_a$, compared to 5 μM for wt IFN-α2 and 100 nM for IFN-β. Binding affinity of HEQ for IFNAR2-EC was 5 nM, similar to wt IFN-α2 and about 10-fold weaker than IFN-β (Table 2).

IFN induces biological activity by the formation of a ternary complex. The effect of increased affinity of HEQ for IFNAR1 on ternary complex binding was determined by measuring dissociation of IFN-α2, HEQ, and IFN-β at different concentrations of IFNAR1-EC and IFNAR2-EC at stoichiometric ratios. While IFN-α2 dissociation kinetics were sharply faster at receptor surface concentration (FIG. 3B), IFN-β and HEQ exhibited slow, largely concentration-independent, dissociation curves (FIGS. 3C-D, respectively). Thus, IFN-β and HEQ recruited IFNAR1-EC to the ternary complex more efficiently than wt IFN-α2.

These findings show that HEQ exhibits enhanced affinity for IFNAR1, similar to IFN-β, yet retains unchanged affinity for IFNAR2 relative to wt IFN-α2.

TABLE 1A

Thermodynamic and kinetic constants for interactions of mutant IFNα2 with IFNAR2-EC

| | $k_d$ [s$^{-1}$] | $K_D$ [nM] | $K_D$ wt/mut | [a]$\Delta G^0$ (kcal/mol) | [b]$\Delta\Delta G^0$ (kcal/mol) |
|---|---|---|---|---|---|
| wt | 0.011 | 3 | | −11.6 | 0.0 |
| H57A | 0.015 | 4 | 1.0 | −11.4 | −0.2 |
| E58A | 0.011 | 3 | 1.3 | −11.6 | 0.0 |
| Q61A | 0.012 | 3 | 1.3 | −11.6 | 0.0 |
| Q62A | 0.009 | 3 | 1.3 | −11.6 | 0.0 |
| F64A | 0.013 | 4 | 1.0 | −11.4 | −0.2 |
| N65A | 0.012 | 3 | 1.3 | −11.6 | 0.0 |
| S68A | 0.010 | 3 | 1.3 | −11.6 | 0.0 |
| T69A | 0.012 | 3 | 1.3 | −11.6 | 0.0 |
| K70A | 0.010 | 3 | 1.3 | −11.6 | 0.0 |
| S73A | 0.014 | 4 | 1.0 | −11.4 | −0.2 |
| T79A | 0.013 | 4 | 1.0 | −11.4 | −0.2 |
| L80A | 0.019 | 5 | 0.8 | −11.3 | −0.3 |
| K83A | 0.011 | 3 | 1.3 | −11.6 | 0.0 |
| Y85A | 0.019 | 5 | 0.8 | −11.3 | −0.3 |
| T86A | 0.016 | 4 | 1.0 | −11.4 | −0.2 |
| Y89A | 0.017 | 5 | 0.8 | −11.3 | −0.3 |
| Q90A | 0.013 | 4 | 1.0 | −11.4 | −0.2 |
| N93A | 0.016 | 4 | 1.0 | −11.4 | −0.2 |
| E96A | 0.013 | 4 | 1.0 | −11.4 | −0.2 |
| V99A | 0.010 | 3 | 1.3 | −11.6 | 0.0 |
| IFNβ | 0.0012 | 0.1 | | −13.6 | |

Notes:
[a]$\Delta G^0$ calculated from $\Delta G^0 = RT\ln K_D$;
[b]$\Delta\Delta G^0 = \Delta G^0_{mut} - \Delta G^0_{wt}$.

TABLE 1B

Thermodynamic and kinetic constants for interactions of mutant IFNα2 with IFNAR1-EC

| | [c]$K_D$ [μM] | $K_D$ wt/mut | [b]$\Delta G^0$ (kcal/mol) | [c]$\Delta\Delta G^0$ (kcal/mol) |
|---|---|---|---|---|
| wt IFNα2 | 1.6 | | −7.9 | |
| H57A | 0.69 | 2.1 | −8.4 | 0.5 |
| E58A | 0.31 | 4.7 | −8.8 | 0.9 |
| Q61A | 0.59 | 2.5 | −8.5 | 0.6 |
| Q62A | 1.82 | 0.8 | −7.8 | −0.1 |
| F64A | 3.33 | 0.4 | −7.4 | −0.5 |
| N65A | 5.00 | 0.3 | −7.2 | −0.7 |
| S68A | 2.00 | 0.7 | −7.8 | −0.2 |
| T69A | 3.70 | 0.4 | −7.4 | −0.6 |
| K70A | 2.56 | 0.6 | −7.6 | −0.3 |
| D71A | 1.67 | 0.9 | −7.8 | −0.1 |
| S73A | 2.94 | 0.5 | −7.5 | −0.4 |
| T79A | 1.45 | 1.0 | −7.9 | 0.0 |
| L80A | 8.70 | 0.2 | −6.9 | −1.1 |
| K83A | 1.47 | 1.0 | −7.9 | 0.0 |
| Y85A | 4.17 | 0.4 | −7.3 | −0.6 |
| T86A | 2.78 | 0.5 | −7.6 | −0.4 |
| Y89A | 5.88 | 0.3 | −7.1 | −0.8 |
| Q90A | 1.43 | 1.0 | −7.9 | 0.0 |
| N93A | 3.23 | 0.5 | −7.5 | −0.5 |
| E96A | 2.86 | 0.5 | −7.5 | −0.4 |
| V99A | 2.00 | 0.7 | −7.8 | −0.2 |
| IFNβ | 0.066 | | −9.75 | 1.85 |

[b]see Table 1A;
[c]$K_D$ was determined from equilibrium binding at the surface.

TABLE 2

Rate constants and affinities of interaction of IFN proteins with IFNAR1 and IFNAR2 as measured by SPR

| | IFNAR1-EC binding | | | IFNAR2-EC binding | | |
|---|---|---|---|---|---|---|
| | $k_a$ [M$^{-1}$s$^{-1}$] | $k_d$ [s$^{-1}$] | $K_D$ [nM] | $k_a$ [M$^{-1}$s$^{-1}$] | $k_d$ [s$^{-1}$] | $K_D$ [nM] |
| IFNα2 | 2·10$^5$ | | 1500 | 3·10$^6$ ± 1·10$^6$ | 0.007 ± 0.003 | 2 |
| IFNβ | 3·10$^5$ ± 1·10$^5$ | 0.02 ± 0.006 | 66 ± 40 | <5·10$^{6a}$ | 0.12 ± 0.001 | <0.2 |
| | | | | | 0.016 ± 0.005[a] | <3[a] |
| HEQ | 3·10$^5$ ± 1·10$^5$ | 0.025 ± 0.005 | 83 ± 50 | 3·10$^6$ ± 1·10$^6$ | 0.007 ± 0.005 | 2 |
| | | | | | 0.3 ± 0.1[a] | 100 ± 40[a] |

Notes:
[a]Interaction with IFNAR2-EC I47A mutant. This mutant was used to probe IFN-β-induced ternary complex formation to put the IFNAR2 dissociation rate constant on par with that of IFN-α2.

Example 4

Identification of IFNα2 Mutants with Enhanced Binding to IFNAR2

Materials and Experimental Methods

Binding measurements. IFNα2 and IFNAR2-EC were expressed and purified as described for Examples 1-2. Binding between IFNAR2-EC and interferons were measured using the ProteOn™ system (ProteOptics, Haifa Israel and Biorad), which utilizes surface plasmon resonance-phase imaging (SPR-PI). 20 µM IFNAR2-EC in PBS (pH 7.4) was biotinylated in a twofold excess of sulfo-NHS-LC-biotin (Pierce, #21335) for 12 h at 4° C., followed by overnight dialysis in PBS (pH 7.4). For immobilization, an activated EDC/NHS surface was covered with NeutrAvidin and blocked with ethylamine, and then 5 of 6 channels were reacted with biotinylated IFNAR2-EC (at a concentration of 2 µM, 180 µl), leaving 1 channel free as a reference. The signal upon binding was 200-400 RU. Additional amounts of IFNAR2-EC did not change the signal significantly upon binding. Binding was measured at 6 different concentrations of protein (100 nM, 50 nM, 25 nM, 12.5 nM, 6.25 nM, 3.12 nM), which were run one after another in horizontal channels, across the ligand channels. Samples were injected at a flow-rate of 30-100 µl/min. Data were analyzed in BIAeval 3.1 software using Langmuir models for fitting kinetic data. Association rate constants were determined from:

$$y = \frac{k_{on} C R_{max}}{k_{on} C + k_{off}} (1 - \exp(-(k_{on} C + k_{off})(t - t_0))) + RI$$

wherein C is the analyte concentration, $R_{max}$ is the maximal binding for the specific analyte, and RI is the change in refractive index upon binding of a specific concentration of analyte.

Dissociation rate constants were determined by fitting the data to a simple exponential equation. Dissociation constants $K_D$ were determined from the rate constants according to: $K_D = k_{off}/k_{on}$.

Stopped-flow. Association was measured using an Applied Photophysics Fluorescence Stopped-flow instrument at 25(±0.1)° C. Excitation wavelength was either 230 nm or 280 nm, dependent on the optimal signal. Emission was detected at >320 nm. Association reactions were measured in second-order conditions with equal concentration (0.5 µM) of both proteins. Data were fit to the equation:

$$F(t) = S + (ACk_{on}t)/(1 + Ck_{on}t)$$

wherein S is the offset, A is the amplitude, C is molar protein concentration and $k_{on}$ is the association rate constant ($M^{-1} s^{-1}$). This equation takes into account only a single relaxation time, while binding is reversible. This is possible when $k_{obs}$ association >> $k_{off}$, and, therefore, it can be fit as it is an irreversible reaction. For the interferon-receptor association reaction at the concentrations used this condition is valid, as τ for association and dissociation are <1 s and >50 s, respectively, for all measured mutants. Independently, $k_{on}$ was determined under pseudo-first-order conditions where IFN was at more than fivefold excess over IFNAR2. Data were fit to an exponential equation to obtain $k_{obs}$. Slope of the linear fit between protein concentration and $k_{obs}$ gives $k_{on}$ (FIG. 4C-D). Standard error of the mean (σ) for $k_{on}$ determined under second-order conditions was ±20%. Values were averaged from at least 3 measurements. For a comparison of 2 samples (for example mut/wt), combined 2σ was ±50%.

Results

To investigate the role of the tail in complex formation with IFNAR2, mutant IFNα2 proteins that mimic the tails of other IFNs with different charge loads on the tail were prepared, specifically: IFNβ (β-tail, charge +1; tail sequence GYLRN, SEQ ID NO: 36), IFNα8 (α8-tail, charge +3; tail sequence KRLKSKE, SEQ ID NO: 37), IFNα8 tail mutant without the terminal glutamic acid (α8-E-tail, charge +4; tail sequence KRLKSK, SEQ ID NO: 38), and IFNα2 lacking its 5 terminal amino acid residues (L161z, charge −1; tail sequence TNLQES, SEQ ID NO: 39) (Table 1A). The charge of the natural IFNα2 tail is zero. The α8-E-tail mutant was designed to observe the effect of a +4-charged tail. L161z is negatively charged, the lowest point in the tail net-charge scale.

FIG. 4 depicts association rate constants measured using ProteOn™ and the stopped-flow apparatus. Under pseudo-first-order conditions, a $k_{on}$ value of $1.07 \times 10^6$ M$^{-1}$s$^{-1}$ was determined with ProteOn™, while $1.03 \times 10^7$ M$^{-1}$s$^{-1}$ was determined with stopped-flow. The same value of $k_{on}$ was determined in the stopped-flow apparatus whether the reaction was monitored under pseudo-first-order- or second-order conditions (FIG. 4D-E). Accordingly, most mutant reactions were measured only under second-order conditions.

Removing the tail (L161z) increases $k_{off}$ by almost twofold with no significant effect on $k_{on}$. Replacement of the IFNα2 wt tail with either the α-tail, α8-tail or α8-E-tail slowed dissociation from IFNAR2, with the β8-tail exhibiting the largest change (Table 2). These three mutants also exhibited significant increases in $k_{on}$, ranging from 50% for the β-tail up to almost sevenfold for the α8-tail. Binding affinity of α8-tail was the tightest among those tested, about 20-fold tighter than the IFNα2 wt, and thus was comparable to IFNβ. In addition, the kinetic rate constants for α8-tail resembled IFNβ (Table 3).

Thus, substitution of the IFNa2 wt tail with tails of increased positive charge, particularly the α8-tail, confers enhanced IFNAR2 binding reminiscent of IFNβ.

TABLE 3

Binding constants for IFN mutants and IFNAR2

| IFN | $k_{off}^c$ (1/s)* | $k_{on} \times 10^{-7d}$ (1/M s)** | $K_D$ (nM) |
|---|---|---|---|
| α2 wt | 0.0066 | 1.15 | 0.58 |
| L161z | 0.014 | 1 | 1.35 |
| β-tail | 0.0041 | 1.85 | 0.22 |
| α8-tail | 0.0020 | 7.50 | 0.026 |
| α8-E tail | 0.0039 | 2.68 | 0.15 |

*measured by SPR;
**measured by stopped-flow.

Example 5

Anti-Proliferative and Antiviral Activities of IFNα2 Mutants

Materials and Experimental Methods

Binding measurements. Binding affinities of IFN toward IFNAR1-EC or IFNAR2-EC were measured using the ProteOn XPR36 Protein Interaction Array system (Bio-Rad). A solution of 0.005% Tween-20 in PBS, pH 7.4, was used as running buffer at a flow rate of 30 µl/min. For immobilization, an activated EDC/NHS surface was covered with non-neutralizing antibodies DB2 and 46.10 against IFNAR1-EC and IFNAR2-EC, respectively, and blocked with ethanolamine.

5/6 channels were reacted with IFNAR1-EC or IFNAR2-EC (180 μl at a concentration of 0.5 μM), followed by crosslinking of a second antibody, AA3 for IFNAR1-EC and 117.7 for IFNAR2-EC. IFN was then injected perpendicular to ligands, at 6 different concentrations within a range of 37-8,000 or 3.12-100 nM nM for IFNAR1 or IFNAR2 binding, respectively. $K_D$ was determined from the rate constants or from the equilibrium response at 6 different analyte concentrations, fitted to the mass-action equation (see Methods for Examples 1-2).

Antiviral protection activity assay. Antiviral activity of wild-type and mutant IFNα2 (n=6) was determined by measuring inhibition of cytopathicity of vesicular stomatitis virus (VSV) on human WISH cells (human epithelial cell line of amniotic origin; Evinger, M. et al., 1981, *Arch. Biochem. Biophys.* 210, 319-329). Relative activity of IFNα2-mutants was expressed as the concentration conferring protection of 50% of cells (antiviral $EC_{50}$) relative to the value for wild-type IFNα2.

The 50% activity point ($EC_{50}$) and rate of change in activity (slope) were deduced from an IFN dose response curve, Eq. 1.

$$y = A_0 + A/(1+(c/c_{50})^s) \quad [\text{Eq. 1}]$$

wherein y is the transmittance, which relates to the number of cells, $A_0$ is the offset, A is the amplitude, c is the concentration, $c_{50}$ is the concentration yielding 50% activity, and s is the slope.

Anti-proliferative assay. For Daudi Burkitt's lymphoma cells, 2-fold serial dilutions of IFNα2 (n=10) were prepared in flat-bottomed 96-well plates, with final concentrations of wild-type IFNα2 ranging from 0.04-82 pM. Concentration ranges for IFNα2 mutants were adjusted according to anticipated anti-proliferative activity as estimated from affinity of the mutant. 100 μl human Daudi Burkitt's lymphoma cells in RPMI 1620+10% fetal calf serum and 4 mM L-glutamine were added into each well and incubated for 60 h with IFN. The number of living cells was determined using a cell staining kit utilizing the tetrazolium salt XTT (Biological Industries Co, Israel). Incubation in the XTT reaction solution for 5 h was following by measurement of absorbance at 475 nm ($A_{475}$). Relative anti-proliferative activities were expressed as the anti-proliferative $EC_{50}$ relative to the value for wild-type IFNα2. n=17 and 7, respectively, for anti-proliferative $EC_{50}$ determinations of IFNα2 and IFNβ.

For WISH cells, interferon was added to the growth media, and cell density was monitored after 72 hr by crystal violet staining.

Results

Antiviral activity against vesicular stomatitis virus (VSV) (in WISH cells) and anti-proliferative activity (for both WISH cells and Daudi cells) of wild-type and mutant IFNα2 proteins were determined. Wild-type IFNβ was 45-fold more potent than IFNα2 in anti-proliferative activity, while the difference in antiviral activity was much larger, namely 2-fold (antiviral $EC_{50}$ were 0.43 and 0.85 pM, and anti-proliferative $EC_{50}$ were 29 and 1360 pM, respectively). Anti-proliferative $EC_{50}$ of IFNα2 was 0.5 pM in Daudi cells (Table 2), over 1000-fold lower than for WISH cells. WISH cells were used for subsequent experiments.

Antiviral $EC_{50}$ of the single mutants were not dramatically altered relative to wild-type. The only mutant exhibiting a >2-fold increase in antiviral $EC_{50}$ was E58A (FIG. 5C). Three single mutations, L80A, Y85A and Y89A, exhibited 2-6 fold decreases. By contrast, combined mutants LYY and NLYY reduced antiviral potency by 30 and 100-fold, respectively (Table 4).

Regarding anti-proliferative activity, E58A and Q61A exhibited modest but statistically significant (3-5 fold) increases. Decreases of similar magnitude were observed for N65A, T69A, L80A, Y85A and Y89A. Reductions in anti-proliferative activity of LYY and NLYY were even larger than for antiviral protection, e.g. 190- and 1100-fold, respectively (Table 4).

HEQ exhibited a larger increase in anti-proliferative activity (FIGS. 5A-B), namely ~25 fold, a value similar to IFNβ (42-fold higher than IFNα2). Antiviral potency of HEQ was increased 2-fold relative to wild-type IFNα2 (FIG. 5C). The increased anti-proliferative activities of HEQ and IFNβ paralleled their increased affinities for IFNAR1.

Thus, antiviral and anti-proliferative activities of HEQ were more similar to IFNβ than to wild-type IFNα2.

Antiviral and anti-proliferative activities of β-tail, α8-tail, and α8-Etail were 3-fold and 10-fold higher than wild-type IFNα2 (FIG. 6 and Table 4).

TABLE 4

Biological Activity of IFNα2 mutants

| IFN Mutant | Antiviral activity (WISH) | | | Anti-proliferative-WISH | | | Antiprolif-DAUDI | |
|---|---|---|---|---|---|---|---|---|
| | 50% (pM) | wt/mut | Slope$^a$ wt/mut | 50% (nM) | wt/mut | slope$^a$ wt/mut | 50% (pM) | wt/mut |
| wt | 0.85 | | | 1.36 | | | 0.5 | |
| H57A | 0.57 | 1.5 | 1.08 | 0.76 | 1.8 | 1.0 | 1.12 | 0.56 |
| E58A | 0.26 | 3.3 | 0.95 | 0.25 | 5.4 | 1.15 | 0.20 | 2.45 |
| Q61A | 0.45 | 1.9 | 1.04 | 0.49 | 2.8 | 1.65 | 0.54 | 0.92 |
| Q62A | 0.45 | 1.9 | | 1.05 | 1.3 | | 0.45 | 1.12 |
| F64A | 0.77 | 1.1 | | 2.72 | 0.5 | | 0.68 | 0.73 |
| N65A | 1.06 | 0.8 | 0.99 | 8.00 | 0.17 | 1.48 | 0.58 | 0.86 |
| S68A | 0.57 | 1.5 | | 0.68 | 2.0 | | 0.52 | 0.96 |
| T69A | 0.94 | 0.9 | | 3.40 | 0.4 | | 0.31 | 1.61 |
| K70A | 0.71 | 1.2 | | 1.70 | 0.8 | | 0.33 | 1.51 |
| D71A | 0.61 | 1.4 | | 1.94 | 0.7 | | 0.30 | 1.67 |
| S73A | 0.61 | 1.4 | | 2.27 | 0.6 | | 0.57 | 0.88 |
| T79A | 0.61 | 1.4 | | 1.94 | 0.7 | | 0.42 | 1.20 |
| L80A | 1.70 | 0.5 | | 9.71 | 0.14 | | 0.47 | 1.07 |
| K83A | 0.65 | 1.3 | | 1.36 | 1.0 | | 0.56 | 0.89 |
| Y85A | 3.27 | 0.26 | 1.0 | 39.0 | 0.035 | 1.84 | 1.52 | 0.33 |
| T86A | 0.77 | 1.1 | | 1.36 | 1.0 | 2.2 | 0.35 | 1.41 |

TABLE 4-continued

Biological Activity of IFNα2 mutants

| IFN Mutant | Antiviral activity (WISH) 50% (pM) | wt/mut | Slope$^a$ wt/mut | Anti-proliferative-WISH 50% (nM) | wt/mut | slope$^a$ wt/mut | Antiprolif-DAUDI 50% (pM) | wt/mut |
|---|---|---|---|---|---|---|---|---|
| Y89A | 4.25 | 0.20 | 1.0 | 30.0 | 0.045 |  | 3.13 | 0.16 |
| Q90A | 0.71 | 1.2 |  | 0.72 | 1.9 |  | 0.45 | 1.11 |
| N93A | 0.85 | 1.0 |  | 1.94 | 0.7 |  | 0.60 | 0.84 |
| E96A | 1.06 | 0.8 |  | 3.40 | 0.4 |  | 1.25 | 0.4 |
| V99A | 1.13 | 0.75 |  | 1.84 | 0.74 |  | 0.51 | 0.98 |
| LYY | 24.29 | 0.035 | 1.32 | 238 | 0.0057 | 4.1 |  |  |
| NLYY | 92.39 | 0.0092 |  | 1478 | 0.00092 | 3.2 |  |  |
| HEQ | 0.41 | 2.07 |  | 0.05 | 24.18 |  |  |  |
| α8-tail | 0.3 | 3 |  | 0.13 | 10 |  |  |  |
| IFNβ | 0.43 | 2 | 0.72 | 0.03 | 42.86 | 0.63 |  |  |

The 50% activity point was obtained by fitting the data to Eq. 1.
$^a$The slope is from Eq. 1.

Example 6

Identification of IFNα2 Mutants with Further Enhancement in IFNAR1 Binding

Cell Lines and Antibodies. Human epithelial WISH cells and human MDA-MB-231 breast cancer cells were provided by Daniela Novick and Lea E Results A phage-display system was utilized to isolate tighter IFNAR1-binding interferon variants out of a library of IFNα2 comprised of random mutations at positions 57, 58, and 61. Proper translation of this fusion protein was verified using anti-FLAG ELISA; positive signals were indicative of both correct translation of the entire fusion protein and sufficient level of integration within the phage capsule. Proper folding of the fused IFNα2 was verified by its ability to bind IFNAR2-EC (KD≈5 nM) by ELISA.

The resulting library contained $10^{11}$ phages/ml, ensuring a high copy representation ($10^7$ phages/ml) of each clone. The first enrichment round of the library included a relatively mild washing step prior to elution with 0.1 M HCl, with subsequent washing steps of increasing stringency. Beginning with the third round, the elution step utilized three sequential elutions using 0.05, 0.1, and 0.2 M HCl (FIG. 7). Specific binding levels peaked at the fifth selection round, from which 20 single phage clones were tested for binding to IFNAR1-EC by ELISA. Four of them produced a signal significantly (3-fold) higher than background). Residues replacing H57, E58, and Q61 in these clones were YNS, MDL, YLD, and YAS. A clear preference for Tyr was observed for position 57, as well as for the combination of Y57 and S61, and for polar over hydrophobic residues at the other 2 positions.

To characterize YNS activity, YNS was injected alone or together with IFNAR1-EC, IFNAR2-EC, or both receptor subunits into an analytical gel-filtration column (FIG. 8). The YNS peak was occluded by either receptor separately, as well as by both receptors together, while forming higher $M_r$ heterodimers and ternary complexes, respectively, whereas wt IFNα2 was not occluded by IFNAR1, indicating that YNS has higher affinity for IFNAR1-EC.

YNS binds IFNAR1 with 60-fold higher affinity than wt IFNα2. Binding affinities of IFNs for IFNAR1-EC and IFNAR2-EC were measured. Affinity of YNS for IFNAR1-EC was 60-fold higher than that of the wt IFNα2 and about 3-fold higher than IFNβ, HEQ, and MDL (FIG. 9 and Table 6). In contrast, affinity of YNS, HEQ, and MDL for IFNAR2 was about equal to that of wt IFNα2.

To verify the higher affinity of YNS for the IFNAR receptor complex within the cellular environment, a binding competition assay on WISH cells was performed. $^{125}$I-labeled wt IFNα2 was mixed with cold IFN (WT or YNS) at concentrations from 0.01 pM-100 nM, and binding of $^{125}$I to cells was measured. YNS exhibited a 20-fold lower $IC_{50}$ value compared with the wild-type protein (Table 6).

Thus, MDL and HEQ exhibit IFNAR binding affinities comparable to IFNβ. YNS exhibits an affinity even greater than IFNβ.

TABLE 6

Biological activities of IFNα2 wild-type, mutants and IFNβ

| | Anti-proliferative activity | | | | Anti-viral activity | |
|---|---|---|---|---|---|---|
| | WISH | | MDA231 | | WISH | |
| | $EC_{50}$ (nM) | Ratio vs. IFNα | $EC_{50}$ (nM) | Ratio vs. IFNα | $EC_{50}$ (pM) | Ratio vs. IFNα |
| wt IFNα | 2.0 | 1 | 0.7 | 1 | 0.6 | 1 |
| wt IFNβ | 0.04 | 50 | 0.07 | 10 | 0.3 | 2.0 |
| YNS | 0.02 | 100 | 0.01 | 70 | 0.2 | 3.0 |
| MDL | 0.085 | 24 | | | 0.6 | 1.0 |
| HEQ | 0.06 | 35 | | | 0.3 | 2.0 |
| α8-tail | 0.2 | 10 | | | 0.2 | 3.0 |

Example 7

YNS has Sharply Enhanced Anti-Proliferative and Antiviral Activity

Materials and Experimental Methods

Antiviral and Anti-proliferative Assays. Anti-proliferative assays on WISH and MDA-MB-231 cells were conducted by adding IFN to the growth medium in flat-bottomed microtiter plates and monitoring cell density after 72 h by crystal violet staining. 50% activity concentrations ($EC_{50}$) and sensitivity of cells to interferon were deduced from an IFN dose-response curve (Kaleidagraph, Synergy Software) using the equation:

$$y = A_0 + A(1 + C/EC_{50})^s$$

wherein y is the absorbance and reflects the relative number of cells, $A_0$ is the offset, A is the amplitude, c is the IFN concentration, and s is the slope (25). Antiviral activity was assayed as described for Examples 1-2. Antiviral and anti-proliferative assays were repeated at least 3 times for each protein. The experimental error (σ) for both assays was 35%. Thus, differences greater than 2-fold between interferons were statistically significant, based on a 2σ confidence level.

Annexin V/PI Assay. Apoptosis was monitored by the phosphatidylserine content on the outer leaflet of the cell membrane with the annexin V-FITC/PI assay kit (Bender MedSystems). Cells were detached with 5 mM EDTA in PBS and labeled with annexin V, then samples were analyzed with a FACSCalibur flow cytometer (BD Biosciences).

Results

Anti-proliferative and antiviral activities of YNS, MDL, and HEQ were assessed on human WISH cells. Consistent with its high affinity toward IFNAR1, YNS exhibited the highest anti-proliferative potency, about 150-fold higher than wt IFNα2, even higher than IFNβ (60-fold), while its antiviral potency was 3.5-fold higher than wt IFNα2, compared to 2-fold higher for IFNβ (Table 6). YNS and IFNβ also exhibited increased anti-proliferative potency relative to wt IFNα2 in MDA MB231 human breast cancer cells (80- and 20-fold, respectively). Antiviral activity of YNS in these cells was sharply higher (16-fold) than wt IFNα2, a number still below the increase in anti-proliferative activity. The absolute molar $EC_{50}$ values for YNS in the 2 cell lines are virtually identical (0.2 versus 0.14 pM), suggesting that the antiviral potency of wt IFNα2 is close to its theoretical limit in WISH cells but not in MDA231. HEQ and MDL also exhibited enhanced anti-proliferative and/or antiviral activity relative to wt IFNα2.

As a general trend, anti-proliferative responses were much more sensitive than antiviral responses to mutations in these regions of IFNα2. The relationship between biological activity and IFNAR1 binding affinity, for the mutants described in this Example and in Example 2, is depicted in FIG. 10; both activities generally scale with the binding affinity, with the exception of antiviral activity of HEQ, YNS, and IFNα2.

Higher anti-proliferative potency of YNS is reflected by higher apoptosis levels at low protein concentration. The anti-proliferative activity of YNS at low concentrations was more similar to IFNβ than to wt IFNα2, as described above (reflected by its lower $EC_{50}$ value), whereas the maximal activity of YNS (as measured by cell density) was more similar to wt IFNα2. Anti-proliferative activity of IFNs results from both growth arrest and apoptosis. To characterize the apoptotic activity of YNS, WISH cells were incubated for 72 h with wt IFNα2, YNS, or IFN, at different concentrations, labeled with annexin V-FITC and PI, and analyzed by flow cytometry. Annexin V is a specific apoptotic marker, whereas PI binds nucleic acids, thus detecting necrotic cells in which the cell membrane is damaged. In this type of cell culture, it is expected that the majority of apoptotic cells are already PI positive, i.e. the state of annexin V-positive/PI-negative is transient (Riss T L and Moravec R A (2004) Assay Drug Dev Technol 2: 51-62).

At low IFN (30 pM) concentrations for a 3-day incubation, YNS exhibited the highest pro-apoptotic activity (FIG. 11), in agreement with its $EC_{50}$. At much higher concentration (1.5 nM), IFNβ activity slightly surpassed that of YNS, which had already reached maximal activity at about 150 pM, consistent with the maximal anti-proliferative activity of these IFNs after 3 days of incubation. However, after longer incubation times the pro-apoptotic activity of YNS closely matched that of IFNβ.

In conclusion, YNS exhibits anti-proliferative, antiviral, and pro-apoptotic activities that are sharply enhanced relative to wt IFNα2 and even higher than IFNβ.

Example 8

Monitoring Gene Activation Using Gene-Chip Technology

Materials and Experimental Methods

Spotted oligonucletide microarray experiments. Poly-L-lysine-coated glass microarrays containing ≈19,000 different probes (Compugen's human oligonucleotide set) were purchased from CAG (Center for Applied Genomics, New Jersey). Microarrays were probed with a mixture consisting of cyanine3 (Cy3)- or Cy5-labeled cDNA representing IFN treatment versus no-treatment (control). WISH cells were treated with different IFNs for 16 hours and their RNA extracted (RNeasy™ Midi kit, Qiagen), 100 µg of which was subjected to reverse transcription (M-MLV H-point mutant RT enzyme, Promega) with aminoallyl-modified dUTP nucleotide (Ambion) mixed in the nucleotide mixture at a 4:1 aa-dUTP:dTTP ratio. The resulting cDNA was labeled with the NHS-activated Cy3 or Cy5 fluorescent probe (Amersham), which binds to the aa-dUTP. Incorporation was assessed (NanoDrop spectrophotometer), and labeled cDNA was mixed (treatment with 1 color and control with the other) at equivalent amounts of fluorescent dye (100 pmoles each), in final 2×SSC, 0.08% SDS and 6 µl of Blocking solution (Amersham), in 100 µl target volume, denatured at 95° C. for 3 minutes, chilled, and applied between a raised cover slip (LifterSlip™, Erie Scientific Company) and the array. Hybridization was performed at 55° C. for 12 hours in the dark, then slides were washed 5 min in 2×SSC, 0.5% SDS at 55° C.; 5 min in 0.5×SSC at rt, and 5 min in 0.05×SSC at rt; dried by centrifuging 3 min at 1000 rpm, and stored in the dark until scanned. In each condition, IFN-treatment versus no-treatment was performed in dye-swap microarray duplicates; 4 replicates of microarray experiments consisting of no-treatment versus no-treatment was used as additional control. Induction was expressed as the normalized ratio between the 2 colors.

Microarray image and data analysis. Scanning of hybridized microarrays was performed with a DNA microarray scanner (Agilent). Automatic spot detection, background subtraction, and intensity quantification were performed with SpotReader™ (Niles Scientific) software. Data normalization, filtering and cluster analysis were performed with Gene-Spring™ (SiliconGenetics) software. Analysis was based on the treatment:control ratio of each spot, and included data filtration by SpotReader output flags, an indication of the quality of the signal, relative to the background (noise). Each treatment (condition) was represented by two dye swap microarray replicates. A starting list of interferon-modulated genes was integrated by genes beyond a 1.7 threshold in at least 2 conditions, tolerating only 1 "absent" ("A") flag, which is indicative of a "noisy" spot, in all conditions per gene.

The list of genes was exported into an Excel worksheet, containing the mean treatment:control ratio value, replicate values, t-test p-values (an estimate of microarray technical error based on the distance between replicates), and flag codes. Genes were then screened for significance, by comparing distance between each pair of replicates and between conditions, considering also p-values and the occurrence of A flags. A mean value beyond the 1.7-threshold having one of its replicates below this threshold, or with a large inter-replicate distance relative to the mean, and with no other conditions with similar and significant levels, was considered not a bonafide modulation, but technical noise, and the gene was consequently excluded from the list. The final list consisted of 395 genes, upregulated or downregulated by interferons at 16 hours of treatment. Cluster analysis was performed on this list after importing it back to GeneSpring.

Results

Gene-chips are a technology to obtain complete information about differential gene-activation. The effect of IFNα2-wt-3 nM, HEQ, and IFNβ on gene expression was monitored by spotted oligonucletide microarray experiments. WISH cells were treated for 16 hours with 0.3 nM IFNα2; 3 nM (10,000 units) IFNα2; 0.3 nM HEQ; or 0.15 nM IFNβ (1,000 units). Concentrations were chosen to produce >90% (IFNα2-wt-3 nM, HEQ, and IFNβ) or under 10% of (IFNα2-wt-0.3 nM) anti-proliferative response in WISH cells.

Gene-chip results can be analyzed on a per-gene basis, or looking at general trends of gene-induction. An overview of the trends in the change in expression levels of 395 IFN-regulated genes, 16 hr after IFN treatment, is depicted in FIG. 12A; expression levels are plotted in ascending order according to fold-change.

Gene expression levels for IFN-β and HEQ were similar and were significantly higher than for 0.3 nM wt IFN-α2 (FIG. 12A). 3 nM wt IFN-α2 induced intermediate levels of gene expression (the same set of genes was induced by 3 nM and 0.3 nM IFN-α2). FIG. 12B depicts levels of gene induction relative to treatment with IFN-β. Genes were sorted in ascending order according to the (IFN-β-induced expression/0.3 nM IFN-α2-induced expression) ratio. Dots represent ratios between the 2 channels on the control chip, providing an estimate of random fluctuation; the low levels of random fluctuation in the control experiment (0.65- to 1.6-fold) provide a high degree of confidence in the data quality. Remarkably, expression levels of every gene analyzed a per-gene basis were not significantly different between IFN-β and HEQ (i.e. not more than the small fluctuation due to random noise), highlighting the similarity of these 2 IFN variants. Cluster analysis of gene activation profiles (FIG. 5C) shows that the profiles for IFN-β and HEQ were the closest, followed by 3 nM wt IFN-α2, with 0.3 nM wt IFN-α2 more distant.

Of the 395 induced genes, 59 upregulated and 9 downregulated genes were selected according to their differential level of activation between the treatments (Table 7) or functional impact. Functional classifications result from manual integration of gene ontology, gene functions found at the GeneCards database, and information obtained through NCBI. Expression of most known interferon-stimulated genes (ISG) was affected by all IFN treatments.

These gene expression profiling results confirm the results regarding the biological activities of these interferon variants, also demonstrating that the HEQ IFN-α2 mutant is exhibits IFN-β-like characteristics.

TABLE 7

Gene expression levels from microarray experiments

| Functional group and GenBank accession no. | HUGO[a] name | Gene induction (fold) | | | | |
|---|---|---|---|---|---|---|
| | | IFN-β | HEQ mutant | IFN-α2 (0.3 nM) | IFN-α2 (3 Nm) | Control (no IFN) |
| Innate immunity | | | | | | |
| NM_002462 | MX1 | 68.3 | 56.3 | 6.1 | 16.3 | 1.0 |
| NM_001548 | IFIT1 | 29.4 | 27.5 | 14.0 | 25.6 | 1.2 |
| NM_006820 | IFI44L | 27.1 | 27.8 | 5.8 | 16.0 | 0.7 |
| M30818 | MX2 | 25.5 | 18.5 | 7.1 | 20.2 | 0.9 |
| NM_002535 | OAS2 | 25.1 | 36.9 | 14.0 | 25.7 | 1.1 |
| NM_014314 | RIG-I | 21.1 | 14.1 | 5.1 | 12.4 | 0.9 |
| NM_016816 | OAS1 | 13.5 | 10.1 | 10.0 | 15.8 | 0.9 |
| AF026941 | RSAD2 | 9.9 | 9.5 | 2.1 | 6.2 | 1.6 |
| NM_0045510 | IFI75 | 9.2 | 7.3 | 3.8 | 6.4 | 1.0 |
| NM_003265 | TLR3 | 7.7 | 6.1 | 1.3 | 2.5 | 1.3 |
| NM_002198 | IRF1 | 4.8 | 3.6 | 1.9 | 2.6 | 1.1 |
| NM_002038 | G1P3 | 4.3 | 3.2 | 3.1 | 4.7 | 1.0 |
| NM_002468 | MYD88 | 4.2 | 3.2 | 2.0 | 3.5 | 1.0 |
| NM_001549 | IFIT4 | 3.7 | 3.3 | 5.5 | 6.0 | 1.1 |
| U72882 | IFI35 | 3.6 | 3.1 | 7.4 | 11.8 | 1.2 |
| NM_004031 | IRF7 | 3.5 | 3.8 | 1.8 | 2.5 | 0.8 |
| NM_002759 | PRKR | 3.0 | 2.9 | 2.1 | 2.8 | 1.1 |
| NM_002053 | GBP1 | 2.9 | 2.0 | 1.2 | 2.1 | 1.0 |
| Acquired immunity | | | | | | |
| NM_018950 | HLA-F | 18.5 | 12.5 | 4.2 | 16.7 | 1.0 |
| NM_000592 | C4B | 6.4 | 4.7 | 2.0 | 2.6 | 1.1 |
| NM_004048 | B2M | 4.9 | 3.7 | 1.4 | 2.6 | 1.0 |
| M14584 | IL6 | 4.7 | 3.3 | 0.9 | 3.1 | 0.8 |
| JAK-STAT pathway | | | | | | |
| NM_007315 | STAT1 | 11.1 | 9.4 | 5.5 | 9.8 | 1.1 |
| NM_005419 | STAT2 | 2.8 | 2.3 | 1.2 | 2.1 | 0.8 |
| NM_006084 | ISGF3G | 2.0 | 2.0 | 2.2 | 3.7 | 1.1 |
| Cell growth inhibition | | | | | | |
| AF095844 | MDA5 | 15.0 | 10.7 | 5.0 | 8.7 | 1.0 |
| NM_005531 | IFI16 | 9.1 | 7.6 | 5.0 | 5.4 | 1.0 |
| NM_004585 | RARRES3 | 4.7 | 3.7 | 1.9 | 3.5 | 0.8 |
| NM_002539 | ODC1 | 0.51 | 0.51 | 0.58 | 0.55 | 0.90 |
| NM_005192 | CDKN3 | 0.47 | 0.53 | 0.57 | 0.46 | 1.00 |
| NM_004616 | TM4SF3 | 0.45 | 0.53 | 0.80 | 0.56 | 0.98 |
| Apoptosis | | | | | | |
| NM_003810 | TNFSF10 | 4.3 | 3.3 | 2.5 | 4.4 | 1.5 |
| NM_001225 | CASP4 | 3.6 | 2.7 | 1.8 | 2.6 | 0.7 |
| NM_001227 | CASP7 | 3.4 | 2.5 | 1.3 | 1.8 | 1.2 |
| NM_004760 | DRAK1 | 2.5 | 2.1 | 1.3 | 2.2 | 0.8 |
| NM_001230 | CASP10 | 2.1 | 1.9 | 1.1 | 1.4 | 1.1 |
| NM_006792 | MORF4 | 0.54 | 0.58 | 0.65 | 0.48 | 0.88 |
| NM_001344 | DAD1 | 0.48 | 0.59 | 0.62 | 0.52 | 1.00 |
| ISGylation and protein degradation | | | | | | |
| NM_017414 | USP18 | 15.8 | 14.4 | 6.9 | 13.5 | 1.0 |
| NM_002800 | PSMB9 | 14.1 | 12.7 | 4.2 | 11.4 | 0.9 |
| NM_002427 | MMP13 | 13.4 | 9.4 | 2.2 | 5.7 | 0.9 |
| NM_001223 | CASP1 | 8.6 | 6.9 | 3.0 | 5.7 | 1.2 |
| NM_004159 | PSMB8 | 5.2 | 5.0 | 2.8 | 4.4 | 1.2 |
| NM_005101 | ISG15 | 5.0 | 6.9 | 5.9 | 12.3 | 0.9 |
| NM_003335 | UBE1L | 4.6 | 4.0 | 2.5 | 3.8 | 0.9 |
| NM_002818 | PSME2 | 3.4 | 3.3 | 1.9 | 2.5 | 0.9 |
| NM_002801 | PSMB10 | 3.3 | 2.8 | 1.6 | 2.7 | 1.0 |
| Protein synthesis inhibition | | | | | | |
| NM_001959 | EEF1B2 | 0.47 | 0.55 | 0.58 | 0.52 | 0.99 |
| NM_001417 | EIF4B | 0.32 | 0.35 | 0.52 | 0.47 | 0.96 |

Example 9

YNS is a More Powerful ISG Inducer than IFNβ

Materials and Experimental Methods

Quantitative PCR. ISG expression levels were measured with the ABI Prism 7300 Real-Time PCR System, using the SYBR Green PCR Master Mix (Applied Biosystems) and cDNA samples were produced with Superscript II (Invitrogen) from 1 μg of total RNA and extracted using RNeasy™ (Qiagen). Primer sequences were designed with Primer Express™ software (Applied Biosystems). Standard curves were generated per primer pair using serial dilutions of an IFN treatment sample, to ensure reaction efficiencies of 100±5%: only primers that yielded a −3.3 slope (±0.3), corresponding to an amplification efficiency of 2 (efficiency= $10^{-1}$/slope) were used. Primer and template concentrations were optimized. Quantitative PCR was performed using 1.25 ng of cDNA for HLA-F, ISG15, and MDA5, and 2.5 ng for TRAIL and CASP1 transcript levels, in a total volume of 20 μl, in triplicate per sample. Relative expression levels were calculated by the δ-δ cycle threshold (Ct) relative quantification (RQ) method (ddCt, $RQ=2^{-ddCt}$), using the untreated cell control as the calibrator sample and glyceraldehyde-3-phosphate dehydrogenase as the endogenous control detector (reference gene levels measured on the same sample), at least in triplicate for each sample. Standard error of ddCt, calculated per sample, was calculated as the square root of the sum of squares of four S.E. & mean Ct; S.E. of tested gene in treatment sample; S.E. of tested gene in control sample; S.E. of reference gene in treatment sample; and S.E. of reference gene in control sample.

Results

To compare the abilities of YNS and IFNβ to induce ISG expression, human WISH cells were treated with different concentrations of IFNα2 WT, IFNβ, or YNS, for varying time periods (8, 16, or 36 h), and ISG expression levels were measured. FIG. 13 depicts expression patterns of 5 genes selected from the up-regulated genes in the microarray experiments (previous Example). YNS and IFNβ exhibited very similar induction patterns, characterized by significantly higher expression levels than wt IFNα2. This was particularly true at the longer time points, wherein YNS was slightly more potent than IFNβ at the lower 30 pM concentration, whereas IFNβ exhibited a stronger effect at the higher concentrations, in striking correlation with the anti-proliferative activities of these interferons. Expression levels of TRAIL, which mediates induction of apoptosis primarily by IFNb and less so by IFNa (Chawla-Sarkar M et al, Preferential induction of apoptosis by interferon (IFN)-beta compared with IFN-alpha2: correlation with TRAIL/Apo2L induction in melanoma cell lines. Clin Cancer Res; 7(6):1821-31, 2001), paralleled apoptosis levels seen hereinabove (Example 7).

In another study with a longer induction period (36 hours of continuous treatment), YNS and IFNβ, but not wt IFNα2, upregulated vasoactive intestinal peptide (VIP) gene production by 10-fold. VIP has been shown to prevent multiple sclerosis in a mouse model by downregulating both inflammatory and autoimmune components of the disease (Fernandez-Martin A et al, VIP prevents experimental multiple sclerosis by downregulating both inflammatory and autoimmune components of the disease. Ann N Y Acad Sci 1070:276-81, 2006).

These results further confirm the above findings that YNS exhibits characteristics of IFNβ but is even more potent than IFNβ in anti-proliferative activity.

Example 10

YNS Confers Enhanced Tumor Protection

Materials and Experimental Methods

Nude mice (n=23, 8-week-old) were injected subcutaneously with MDA-MB-231 human breast cancer cells ($10^7$ in 0.2 ml PBS). Mice were divided randomly into 4 treatment groups (IFNα2, YNS, control, and IFNβ). 20 μg IFN in 0.2 ml of PBS or vehicle alone (control mice) was injected intraperitoneally, twice a week, after evaluating numbers and size of tumors, from day 3 to day 35, and mice were sacrificed. Tumor remainders and suspected scar tissue were surgically removed, fixed in 4% formaldehyde, and embedded in paraffin blocks. Sections were stained with hematoxylin-eosin (H&E) for histological analysis (Wagner T C et al, Interferon receptor expression regulates the anti-proliferative effects of interferons on cancer cells and solid tumors. Int J Cancer; 111(1):32-42, 2004).

Results

To determine the biological potency of YNS for tumor inhibition in vivo, MDA MB231 cell breast cancer xenografts were subcutaneously injected into nude mice. Animals were divided into 4 treatment groups: YNS (n=6), wt IFNα2 (n=6), IFNβ (n=5), and vehicle (PBS, n=6). One week following MDA231 cell injection, all mice developed tumors. Within 26 days of the first IFN injection, all tumors in YNS-treated mice were cleared, whereas 5/6 mice in the wt IFNα2 group exhibited visible tumors. All mice in the mock-treated group exhibited visible tumors, which were larger than in the wt IFNα2 mice (Table 8 and FIG. 14A). IFNβ-treated mice were free of tumors 22 days after the first injection, with the exception of a single lump. Tumors of 4/6 mice in the YNS-treated group went through a necrotic process, as was the case for 5/5 tumors in the IFNβ group; a phenomenon absent in the wt IFNα2 and control groups. Remaining tumors and scars were subjected to histological analysis (FIG. 14B). All sections from the YNS- and IFNβ-treated group were clean of tumor cells and contained healthy scar tissue. The single visible lump in the IFNβ group turned out to be an inflammatory response, which may have been due to bacterial infection, and was clean of cancerous cells. Of the 5 visible tumors in the wt IFNα2 group, 3 exhibited clear tumor morphology, and 2 contained mainly fat cells.

These results show that YNS exhibits significantly enhanced anti-tumor activity relative to wt IFNα2, further confirming the findings presented in the above Examples regarding the enhanced potency and biological activity of this mutant.

TABLE 8

Size of MDA231 breast cancer tumors

| Days | PBS | | | | IFNα2 | | | | IFNβ | | | | YNS | | | |
|---|---|---|---|---|---|---|---|---|---|---|---|---|---|---|---|---|
| | L | M | S | N | L | M | S | N | L | M | S | N | L | M | S | N |
| 1  | 1 | 0 | 0 | 5 |   |   | 4 | 2 |   | 4 |   |   | 1 | 0 | 0 | 6 | 0 |
| 5  | 1 | 0 | 4 | 0 | 1 | 0 | 5 | 0 | 5 |   |   |   | 3 | 0 | 3 | 0 |
| 8  | 1 | 2 | 2 | 0 | 1 | 0 | 5 | 0 | 3 | 2 |   |   | 3 | 2 | 1 | 0 |
| 12 | 1 | 2 | 3 | 0 | 0 | 0 | 5 | 1 | 3 | 2 |   |   | 3 | 1 | 2 | 0 |
| 15 | 3 | 2 | 3 | 0 | 0 | 0 | 5 | 1 | 3 | 2 |   |   | 1 | 3 | 0 | 2 |
| 18 | 3 | 0 | 3 | 0 | 0 | 0 | 4 | 2 | 1 | 1 |   |   | 3 | 1 | 3 | 0 | 2 |
| 22 | 3 | 1 | 2 | 0 | 0 | 0 | 4 | 2 | 1 |   |   |   | 4 | 1 | 0 | 0 | 3 |
| 26 | 3 | 2 | 1 | 0 | 0 | 1 | 4 | 1 | 1 |   |   |   | 4 | 0 | 0 | 0 | 6 |
| 29 | 3 | 2 | 1 | 0 | 0 | 1 | 3 | 2 | 1 |   |   |   | 4 | 0 | 0 | 0 | 6 |
| 33 | 3 | 2 | 1 | 0 | 0 | 2 | 3 | 1 | 1 |   |   |   | 4 | 0 | 0 | 0 | 6 |
| 34 | 3 | 2 | 1 | 0 | 1 | 2 | 2 | 1 | 1 |   |   |   | 4 | 0 | 0 | 0 | 6 |

Example 11

Combined IFNAR1/2 Binding Mutations

On the background of the YNS mutant, a series of additional mutations was constructed, on the IFNAR2 binding interface of IFNα2. The following four residues on IFNα2 were mutated to Ala: Ser153, Met148, Leu30, and Arg33. Binding affinities of these mutants, both alone and on an YNS background, for IFNAR1 or IFNAR2 were determined using the ProteOn™ XPR36 Protein Interaction Array. The alanine mutations reduced affinity for IFNAR2 to the same extent whether or not on the YNS background, while the YNS mutation increased the affinity for IFNAR1 by 50-60 fold for all mutants (Table 9).

TABLE 9

Binding of mutants to IFNAR1 and IFNAR2.

| | IFNAR1 | | IFNAR2 | | Combined | R2/R1 |
|---|---|---|---|---|---|---|
| | KD (μM) | Relative (to wt) | KD (μM) | Relative (to wt) | R1*R2 Affinity | affinity ratio |
| Wt | 1.6 | 1 | 0.002 | 1 | 1 | 790 |
| YNS | 0.03 | 53 | 0.0014 | 1.4 | 75.2 | 21 |
| YNS/153A | 0.023 | 70 | 0.019 | 0.11 | 7.68 | 1.2 |
| YNS/148A | 0.037 | 43 | 0.087 | 0.023 | 1 | 0.43 |
| YNS/30A | 0.03 | 53 | 1.7 | 0.0012 | 0.064 | 0.018 |
| YNS/33A | 0.04 | 40 | 29 | 0.00007 | 0.0028 | 0.0017 |
| 30A | | 1 | 1.7 | 0.0012 | | |
| 33A | | 1 | 29 | 0.00007 | | |
| NLYY | | | | 1 | | |

Next, measurements of binding of the 4 combined IFN mutants (i.e. YNS together with the 4 additional mutations described above) and L30A, R33A, and NLYY to native cell surface receptors in situ were performed as described above for Example 6. Positive correlation was found between $EC_{50}$ values and combined affinities of IFNs to both receptors (R1×R2, FIGS. 15-16 and Table 10), suggesting that the combined affinity in the context of the ternary complex is a function of the additive value of the individual contributions. For example, the weakest IFNAR2 binding mutant tested was R33A, reducing binding to IFNAR2 to 29 μM. The in situ $EC_{50}$ value of 1.1 μM and 3 nM for this mutant in the absence and presence of the YNS mutations represents the synergistic binding to both receptors.

TABLE 10

Binding in situ.

| | EC50 [nM] | Error | Relative (to wt) | Combined affinity (R1*R2) |
|---|---|---|---|---|
| wt | 0.044 | 0.0060 | 1 | 1 |
| YNS | 0.0029 | 0.00031 | 16 | 75.2 |
| YNS/153A | 0.017 | 0.0045 | 2.6 | 7.68 |
| YNS/148A | 0.16 | 0.022 | 0.28 | 1 |
| YNS/30A | 0.28 | 0.058 | 0.16 | 0.064 |
| YNS/33A | 2.9 | 0.89 | 0.015 | 0.0028 |
| 30A | 110 | 22 | 0.00028 | 0.0012 |
| 33A | 1100 | 371 | 0.000027 | 0.00007 |
| NLYY | 4.00 | 0.74 | 0.0075 | ND |

Example 12

YNS Downregulates Surface IFN Receptor with High Potency, Comparable to IFNβ

IFN surface receptor downregulation is a means of signal attenuation following an IFN stimulus that contributes to full and fast transduction of the IFN signal. To compare ability of the different IFN variants to induce IFNAR1 downregulation, WISH cells were treated with IFN, and surface receptor numbers were quantified by flow cytometry. During the course of IFN treatment at low concentrations (30 pM), levels of both IFNAR subunit levels were initially downregulated, followed by a linear recovery over time, as expected (FIG. 17A). At 300 pM, however, IFNβ (but not IFNα2) was able to downregulate IFNAR1 for the entire length of the experiment (24 hrs), while surface expression levels of IFNAR2 returned to normal. Next, cells were incubated with YNS and the combined mutants at 100 pM. At this concentration, a maximal antiproliferative response was induced with IFNβ and YNS, but not with IFNα2 or the combined mutants. The YNS/L30A mutant promoted the weakest IFNAR1 downregulation, in agreement with its weak combined affinity.

These results show that a high affinity to IFNAR1 is not sufficient to induce its continuous downregulation, and confirm a correlation between this differential receptor downregulation and the antiproliferative signal. Thus, differential receptor downregulation is dictated by the integral life time of the ternary receptor-IFN complex, which is a function of the binding affinity of the IFN for the receptors and the concentration of the IFN. These findings further confirm the previous results showing that YNS exhibits characteristics of IFNβ.

Example 13

Experimental Autoimmune Encephalomyelitis (EAE)

Experimental Autoimmune Encephalomyelitis (EAE), also known as Experimental Allergic Encephalomyelitis, is an animal model of multiple sclerosis (MS). Various EAE models are known in the art, depending on the method of induction, the strain of the animal and the antigen employed to induce the disease. EAE is an acute or chronic-relapsing, acquired, inflammatory and demyelinating autoimmune disease. Different forms of EAE resemble very closely various forms and stages of MS.

In the present study, EAE is induced by injection of Myelin Basic Protein (MBP), a method known to model the acute phase of MS. In this model the onset of the disease is observed by the appearance of clinical symptoms about 10 days after induction. The disease progresses and the clinical score increases and peaks around day 15 and spontaneous recovery is observed around day 23 after induction of the disease.

Female Lewis rats (average body weight 130-180 g) are injected s.c. into the hind paws with 25 µg of purified guinea pig myelin basic protein (MBP, Sigma) emulsified in 0.1 ml of Complete Freund's Adjuvant (Difco). Animals are maintained on a 12-hour light/12-hour dark regimen, at a constant temperature of 22° C., with food and water ad libitum. Starting from day 8 following induction, animals are followed up on a daily basis. The results are recorded as clinical score; score of 0 indicates a normal animal with no clinical signs, 0.5 indicates a loss of tonicity in the distal part of the tail, 1 indicates whole tail paralysis, 1.5 indicates weakness in one hind leg, 2 indicates weakness in both hind legs, 2.5 indicates in one fore leg, 3 indicates paralysis of all four legs, 4 indicates complete body paralysis and moribund state and 5 indicates death. The clinical score of the animals is recorded for ~15 days following onset of disease until the end of the study 25 days following induction and the area under the curve (AUC) is calculated over this period of time.

Animals that exhibit symptom of the disease, which could be clinically scored between 0.5 and 1, are treated with compositions of HEQ, YNS, wt IFNα2, IFNβ, or vehicle control for 3 consecutive days starting from the onset of the disease (~ at day 9-11 following disease induction). Several routes of administration are assessed, for example, intravenously (in vehicle) or orally by gavage (in vehicle) at volume dose of 5 ml/kg. On the last day of study (about day 25) animals are euthanized with sodium pentobarbitone 100 mg/kg i.p.

Results are expressed as mean±SEM and the differences between the treatment groups were analyzed by analysis of variance (ANOVA) followed by Tukey's post hoc test. A value of $p<0.05$ is considered to be statistically significant and is indicated on the figure by an asterisk over the relevant treatment group.

Methylprednisolone is used as a positive control. When the steroid is administered daily for 5 consecutive days i.v. at 30 mg/kg starting from day of disease induction by MBP injection, a significant reduction in AUC is observed.

Example 14

An Animal Model of Systemic Lupus Erythematosus (SLE)

Female $(NZB \times NZW)_{F1}$ hybrid mice (referred to hereafter as "NZB/W mice") spontaneously develop a lupus-like disease characterized by the presence of serum autoantibodies to double-stranded DNA (dsDNA). These mice, which eventually experience total kidney failure, are often used as a model for experimentation directed at better understanding and treating lupus in humans. Over time, this condition in NZB/W mice progresses to kidney malfunction as manifested by the appearance of proteinuria.

Female NZB/W mice 32 weeks of age are used in an experiment to test the ability of NLYY to delay the development of lupus-like disease. Mice are divided into 2 groups, and each group is treated every 2 days with either NLYY (n=10) or rat IgG as a control (n=10), administered by intraperitoneal injection. Treatments are continued for five weeks, and the mice are assessed weekly for the presence of proteinuria.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A mutated human interferon α2 (IFNα2) polypeptide comprising at least two mutations in SEQ ID NO: 2, with the mutations selected from the group consisting of (a) mutation of the histidine at position 57 to a residue selected from the group consisting of tyrosine and methionine; (b) mutation of the glutamate at position 58 to a residue selected from the group consisting of asparagine, aspartate, leucine, and alanine; and (c) mutation of the glutamine at position 61 to a residue selected from the group consisting of serine, leucine, and aspartate; and combinations thereof of mutations (a), (b), and (c), wherein the mutation increases the affinity of the mutated human IFNa2 polypeptide for the IFNAR1 subunit of the interferon receptor (IFNAR) relative to wild-type IFN-α2.

2. The mutated human IFNα2 polypeptide of claim 1, wherein the mutated human IFNα2 polypeptide comprises all three of mutations (a), (b), and (c).

3. The mutated human IFNα2 polypeptide of claim 1, wherein the histidine at position 57 is mutated to tyrosine.

4. The mutated human IFNα2 polypeptide of claim 1, wherein the mutated human IFNα2 polypeptide comprises the mutations H57Y and Q61S.

5. The mutated human IFNα2 polypeptide of claim 1, wherein the mutated human IFNα2 polypeptide comprises the mutations H57Y, E58N, and Q61S.

6. The mutated human IFNα2 polypeptide of claim 1, wherein the mutated human IFNα2 polypeptide comprises the mutations H57M, E58D, and Q61L.

7. The mutated human IFNα2 polypeptide of claim 1, wherein the mutated human IFNα2 polypeptide comprises the mutations H57Y, E58L, and Q61D.

8. The mutated human IFNα2 polypeptide of claim 1, wherein the mutated human IFNα2 polypeptide comprises the mutations H57Y, E58A, and Q61S.

9. The mutated human IFNα2 polypeptide of claim 1, wherein the mutated human IFNα2 polypeptide further comprises an additional mutation, the additional mutation being a mutation of a residue selected from the group consisting of E159, S160, L161, S163, and E165, and combinations thereof, to a residue selected from the group consisting of lysine and arginine.

10. The mutated human IFNα2 polypeptide of claim 9, wherein two or more of the residues selected from the group consisting of E159, S160, L161, S163, and E165 are mutated to a residue selected from the group consisting of lysine and arginine.

11. The mutated human IFNα2 polypeptide of claim 9, wherein three or more of the residues selected from the group consisting of E159, S160, L161, S163, and E165 are mutated to a residue selected from the group consisting of lysine and arginine.

12. The mutated human IFNα2 polypeptide of claim 9, wherein the additional mutation is selected from the group consisting of (a) mutation of the E159 to lysine; and (b) mutation of the S160 to arginine; and a combination thereof.

13. The mutated human IFNα2 polypeptide of claim 9, wherein the additional mutation results in the 7 carboxy-terminal residues of the mutated human IFNα2 polypeptide having a net charge of +3 or higher.

14. The mutated human IFNα2 polypeptide of claim 9, wherein the additional mutation results in the 7 carboxy-terminal residues of the mutated human IFNα2 polypeptide having a net charge of +4 or higher.

15. The mutated human IFNα2 polypeptide of claim 1, wherein the mutated human IFNα2 polypeptide further comprises an additional mutation, the additional mutation being a substitution of the 5-10 C-terminal residues of the mutated human IFNα2 polypeptide to a sequence selected from the group consisting of KRLKSKE (SEQ ID NO: 43) and KRLKSK (SEQ ID NO: 44).

16. The mutated human IFNα2 polypeptide of claim 1, wherein the mutated human IFNα2 polypeptide further comprises an additional mutation selected from the group consisting of a mutation to alanine of a residue selected from the group consisting of (a) leucine at position 30, (b) arginine at position 33, (c) methionine at position 148, and (d) serine at position 153, and combinations thereof, wherein the additional mutation decreases affinity of the mutated human IFNα2 polypeptide for the IFNAR2 subunit of the interferon receptor 1 (IFNAR) relative to wild-type IFN-α2.

17. The mutated human IFNα2 polypeptide of claim 1, wherein the mutated human IFNα2 polypeptide is further conjugated to polyethylene glycol (PEG).

18. A pharmaceutical composition comprising as an active ingredient the mutated human IFNα2 polypeptide of claim 1, and further comprising a pharmaceutically acceptable carrier.

19. A method of treating or ameliorating a cancer or infectious disease in a subject in need thereof, wherein the cancer or infectious disease is responsive to treatment with recombinant interferon-beta, the method comprising the step of administering to the subject the pharmaceutical composition of claim 18, thereby treating or ameliorating the cancer or infectious disease.

20. The method of claim 19, for treating or ameliorating a cancer selected from the group consisting of hepatocellular carcinoma, hairy cell leukemia, Kaposi's sarcoma, multiple myeloma, chronic myelogenous leukemia, non-Hodgkins's lymphoma and melanoma.

21. The method of claim 19, for treating or ameliorating an infectious disease selected from the group consisting of hepatitis A, hepatitis B, hepatitis C, and salmonella infection.

22. A method of treating or ameliorating an autoimmune disease in a subject in need thereof, wherein the autoimmune disease is responsive to treatment with recombinant interferon-beta, the method comprising the step of administering to the subject the pharmaceutical composition of claim 18, thereby treating or ameliorating the autoimmune disease.

23. The method of claim 22, wherein the autoimmune disease is multiple sclerosis (MS).

24. A mutated human interferon α2 (IFNα2) polypeptide comprising mutating to alanine at least three residues of SEQ ID NO: 2 selected from the group consisting of (a) mutation of the histidine at position 57; (b) mutation of the glutamate at position 58; (c) mutation of the glutamine at position 61; (d) mutation of the asparagine at position 65; (e) mutation of the leucine at position 80; (f) mutation of the tyrosine at position 85; and (g) mutation of the tyrosine at position 89; wherein at least one of the mutations to alanine is selected from (c), (e), and (f), and wherein the mutation decreases affinity of the mutated human IFNα2 polypeptide for the IFNAR1 subunit of the interferon receptor 1 (IFNAR) relative to wild-type IFN-α2.

25. The mutated human IFNα2 polypeptide of claim 24, wherein the mutated human IFNα2 polypeptide comprises mutations (a), (b), and (c).

26. The mutated IFNα2 polypeptide of claim 24, wherein the polypeptide comprises at least three mutations selected from N65A, L80A, Y85A, and Y89A.

27. The mutated human interferon a2 (IFNa2) polypeptide according to claim 26 comprising the three mutations L80A, Y85A, and Y89A.

28. The human interferon a2 (IFNa2) polypeptide according to claim 26 comprising the four mutations N65A, L80A, Y85A, and Y89A.

29. The mutated IFNα2 polypeptide of claim 24, wherein the polypeptide comprises the three mutations H57A, E58A, and Q61A.

30. The mutated human IFNα2 polypeptide of claim 24, wherein the mutated human IFNα2 polypeptide further comprises an additional mutation, the additional mutation being a mutation of a residue selected from the group consisting of E159, S160, L161, S163, and E165, and combinations thereof, to a residue selected from the group consisting of lysine and arginine.

31. The mutated human IFNα2 polypeptide of claim 30, wherein two or more of the residues selected from the group consisting of E159, S160, L161, S163, and E165 are mutated to a residue selected from the group consisting of lysine and arginine.

32. The mutated human IFNα2 polypeptide of claim 30, wherein three or more of the residues selected from the group consisting of E159, S160, L161, S163, and E165 are mutated to a residue selected from the group consisting of lysine and arginine.

33. The mutated human IFNα2 polypeptide of claim 30, wherein the additional mutation is selected from the group consisting of (a) mutation of the E159 to lysine; and (b) mutation of the S160 to arginine; and a combination thereof.

34. The mutated human IFNα2 polypeptide of claim 30, wherein the additional mutation results in the 7 carboxy-terminal residues of the mutated human IFNα2 polypeptide having a net charge of +3 or higher.

35. The mutated human IFNα2 polypeptide of claim 30, wherein the additional mutation results in the 7 carboxy-terminal residues of the mutated human IFNα2 polypeptide having a net charge of +4 or higher.

36. The mutated human IFNα2 polypeptide of claim 24, wherein the mutated human IFNα2 polypeptide further comprises an additional mutation, the additional mutation being a substitution of the 5-10 C-terminal residues of the mutated human IFNα2 polypeptide to a sequence selected from the group consisting of KRLKSKE (SEQ ID NO: 43) and KRLKSK (SEQ ID NO: 44).

37. The mutated human IFNα2 polypeptide of claim 24, wherein the mutated human IFNα2 polypeptide is further conjugated to polyethylene glycol (PEG).

38. A pharmaceutical composition comprising as an active ingredient the mutated human IFNα2 polypeptide of claim 24, and further comprising a pharmaceutically acceptable carrier.

39. A method of treating or ameliorating a disorder or disease associated with excessive activity or expression of a Type I interferon in a subject in need thereof, the method comprising the step of administering to the subject the pharmaceutical composition of claim 38, thereby treating or ameliorating a disorder or disease associated with excessive activity or expression of a Type I interferon in a subject in need thereof.

40. The method of claim 38, wherein the disorder is insulin-dependent diabetes mellitus (IDDM) or systemic lupus erythematosus (SLE).

41. A mutated human interferon α2 (IFNα2) polypeptide comprising a mutation in SEQ ID NO: 2 of a residue selected from the group consisting of E159, S160, L161, S163, and E165, and combinations thereof, to a residue selected from the group consisting of lysine and arginine.

42. The mutated human IFNα2 polypeptide of claim 41, wherein two or more of the residues selected from the group consisting of E159, S160, L161, S163, and E165 are mutated to a residue selected from the group consisting of lysine and arginine.

43. The mutated human IFNα2 polypeptide of claim 41, wherein three or more of the residues selected from the group consisting of E159, S160, L161, S163, and E165 are mutated to a residue selected from the group consisting of lysine and arginine.

44. The mutated human IFNα2 polypeptide of claim 41, wherein the mutation is selected from the group consisting of (a) mutation of the E159 to lysine; and (b) mutation of the S160 to arginine; and a combination thereof.

45. The mutated human IFNα2 polypeptide of claim 41, wherein the mutation results in the 7 carboxy-terminal residues of the mutated human IFNα2 polypeptide having a net charge of +3 or higher.

46. The mutated human IFNα2 polypeptide of claim 41, wherein the mutation results in the 7 carboxy-terminal residues of the mutated human IFNα2 polypeptide having a net charge of +4 or higher.

47. The mutated human IFNα2 polypeptide of claim 41, wherein the mutated human IFNα2 polypeptide is further conjugated to polyethylene glycol (PEG).

48. A pharmaceutical composition comprising as an active ingredient the mutated human IFNα2 polypeptide of claim 41, and further comprising a pharmaceutically acceptable carrier.

49. A method of treating or ameliorating a cancer or infectious disease in a subject in need thereof, wherein the cancer or infectious disease is responsive to treatment with recombinant interferon-beta, the method comprising the step of administering to the subject the pharmaceutical composition of claim 48, thereby treating or ameliorating the cancer or infectious disease.

50. The method of claim 49, for treating or ameliorating a cancer selected from the group consisting of hepatocellular carcinoma, hairy cell leukemia, Kaposi's sarcoma, multiple myeloma, chronic myelogenous leukemia, non-Hodgkins's lymphoma and melanoma.

51. The method of claim 49, for treating or ameliorating an infectious disease selected from the group consisting of hepatitis A, hepatitis B, hepatitis C, and salmonella infection.

52. A method of treating or ameliorating an autoimmune disease in a subject in need thereof, wherein the autoimmune disease is responsive to treatment with recombinant interferon-beta, the method comprising the step of administering to the subject the pharmaceutical composition of claim 48, thereby treating or ameliorating the autoimmune disease.

53. The method of claim 52, wherein the autoimmune disease is multiple sclerosis (MS).

54. A mutated human interferon α2 (IFNα2) polypeptide comprising a substitution mutation in SEQ ID NO: 2 of the 5-10 C-terminal residues of the polypeptide to a sequence selected from the group consisting of KRLKSKE (SEQ ID NO: 43) and KRLKSK (SEQ ID NO: 44).

55. The mutated human IFNα2 polypeptide of claim 54, wherein the mutated human IFNα2 polypeptide is further conjugated to polyethylene glycol (PEG).

56. A pharmaceutical composition comprising as an active ingredient the mutated human IFNα2 polypeptide of claim 54, and further comprising a pharmaceutically acceptable carrier.

57. A method of treating or ameliorating a cancer or infectious disease in a subject in need thereof, wherein the cancer or infectious disease is responsive to treatment with recombinant interferon-beta, the method comprising the step of administering to the subject the pharmaceutical composition of claim 56, thereby treating or ameliorating the cancer or infectious disease.

58. The method of claim 57, for treating or ameliorating a cancer selected from the group consisting of hepatocellular carcinoma, hairy cell leukemia, Kaposi's sarcoma, multiple myeloma, chronic myelogenous leukemia, non-Hodgkins's lymphoma and melanoma.

59. The method of claim 57, for treating or ameliorating an infectious disease selected from the group consisting of hepatitis A, hepatitis B, hepatitis C, and salmonella infection.

60. A method of treating or ameliorating an autoimmune disease in a subject in need thereof, wherein the autoimmune disease is responsive to treatment with recombinant interferon-beta, the method comprising the step of administering to the subject the pharmaceutical composition of claim 56, thereby treating or ameliorating an ameliorating the autoimmune disease.

61. The method of claim 60, wherein the autoimmune disease is multiple sclerosis (MS).

* * * * *

UNITED STATES PATENT AND TRADEMARK OFFICE
CERTIFICATE OF CORRECTION

PATENT NO. : 7,919,078 B2  
APPLICATION NO. : 11/969319  
DATED : April 5, 2011  
INVENTOR(S) : Schreiber et al.

Page 1 of 1

It is certified that error appears in the above-identified patent and that said Letters Patent is hereby corrected as shown below:

Title Page:  
Item (56) References Cited, OTHER PUBLICATIONS, add the following reference:  
-- International Search Report corresponding to PCT/IL06/00754, filed 6/28/2006* --.

In the Claims:  
Column 101:  
Line 48 (claim 1, line 12), change "IFNa2" to -- IFNα2 --.

Column 104:  
Line 1 (claim 27, line 1), change "a2 (IFNa2)" to -- α2 (IFNα2) --.  
Line 4 (claim 28, line 1), change "a2 (IFNa2)" to -- α2 (IFNα2) --.

Column 106:  
Line 41 (claim 60, line 6), after "ameliorating" delete "an ameliorating".

Signed and Sealed this  
Sixteenth Day of April, 2013

Teresa Stanek Rea  
*Acting Director of the United States Patent and Trademark Office*